(12) United States Patent
Mizoshita et al.

(10) Patent No.: US 8,053,588 B2
(45) Date of Patent: Nov. 8, 2011

(54) ORGANOSILANE COMPOUND AND ORGANOSILICA OBTAINED THEREFROM

(75) Inventors: Norihiro Mizoshita, Nagoya (JP); Yasutomo Goto, Owariasahi (JP); Shinji Inagaki, Nagoya (JP); Toyoshi Shimada, Soraku-gun (JP)

(73) Assignees: Kabushiki Kaisha Toyota Chuo Kenkyusho, Aichi-gun (JP); Toyoshi Shimada, Kyoto (JP)

( * ) Notice: Subject to any disclaimer, the term of this patent is extended or adjusted under 35 U.S.C. 154(b) by 724 days.

(21) Appl. No.: 12/073,339

(22) Filed: Mar. 4, 2008

(65) Prior Publication Data

US 2008/0227939 A1  Sep. 18, 2008

(30) Foreign Application Priority Data

Mar. 7, 2007  (JP) .................................. 2007-057353
Jan. 11, 2008  (JP) .................................. 2008-004876

(51) Int. Cl.
*C07F 7/04* (2006.01)
(52) U.S. Cl. .................. 556/482; 556/463; 526/279
(58) Field of Classification Search ........................ None
See application file for complete search history.

(56) References Cited

FOREIGN PATENT DOCUMENTS
JP    A-2006-89588    4/2006

OTHER PUBLICATIONS

Maegawa et al, Tetrahedron, 2007, 63, 11467-11474.*

(Continued)

*Primary Examiner* — Sudhakar Katakam
(74) *Attorney, Agent, or Firm* — Oliff & Berridge, PLC

(57) ABSTRACT

Provided is an organosilane compound expressed by any one of the following general formulae (1) to (7):

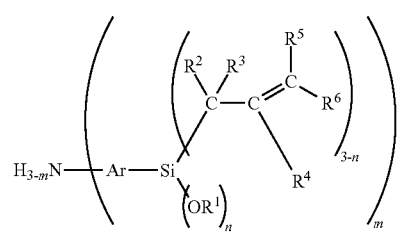

(1)

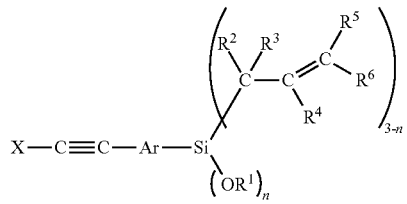

(2)

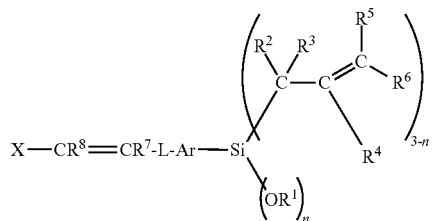

(3)

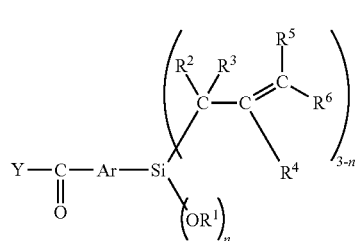

(4)

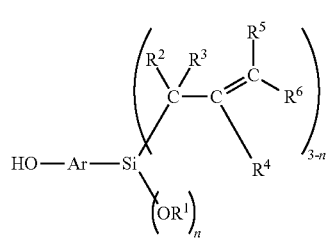

(5)

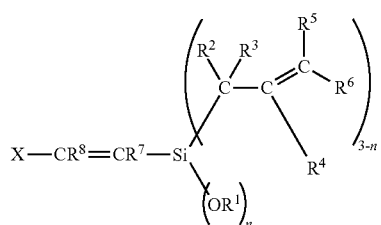

(6)

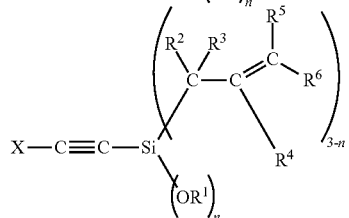

(7)

(wherein: Ar represents a phenylene group or the like; $R^1$ represents a hydrogen atom or the like; $R^2$ to $R^8$ each represent a methyl group or the like; n represents an integer in a range from 0 to 2; m represents an integer of 1 or 2; L represents a single bond or the like; X represents a hydrogen atom or the like; and Y represents a hydrogen atom or the like).

7 Claims, 7 Drawing Sheets

OTHER PUBLICATIONS

Deng et al., "An Efficient Convergent Synthesis of Novel Anisotropic Adsorbates Based on Nanometer-Sized and Tripod-Shaped Oligophenylenes End-Capped with Triallylsilyl Groups," *Journal of Organic Chemistry,* 2002, vol. 67, pp. 5279-5283.

Kapoor et al., "An Alternate Route for the Synthesis of Hybrid Mesoporous Organosilica with Crystal-Like Pore Walls from Allylorganosilane Precursors," *J. Am. Chem. Soc.,* 2005, vol. 127, pp. 8174-8178.

Kapoor et al., "Self-assembly of cubic phenylene bridged mesoporous hybrids from allylorganosilane precursors," *J. Mater Chem.,* 2006, vol. 16, pp. 3305-3311.

* cited by examiner

ORGANOSILANE COMPOUND AND ORGANOSILICA OBTAINED THEREFROM

BACKGROUND OF THE INVENTION

1. Field of the Invention

The present invention relates to an organosilane compound and an organosilica obtained from the organosilane compound.

2. Related Background Art

Studies have been conducted on various organosilane compounds and organosilicas obtained from the organosilane compounds. For example, the Journal of Organic Chemistry, Vol. 67, pp. 5279 to 5283, 2002 (document 1) discloses an oligophenylene-based organosilane as an organosilane which can be utilized as a surface-treating agent. This document 1 also discloses a triallylsilylbenzene derivative having a halogen substituent or a boranyl substituent, as an organosilane compound for producing an oligophenylene-based organosilane.

Additionally, Japanese Unexamined Patent Application Publication No. 2006-89588 (document 2) discloses an organosilica obtained by hydrolysis and polycondensation of a certain organosilane compound, including an organosilane compound having an allylsilyl group, in a solvent.

However, it is difficult to use the organosilane compounds of the above-mentioned documents as a raw-material compound for producing an organosilica having various functions, such as a refractive-index controlling function, a light absorbing function, a light emitting function, and a charge transferring function.

SUMMARY OF THE INVENTION

The present invention has been made in consideration of the problems in the related art. An object of the present invention is to provide an organosilane compound which is useful for a synthesis of an organosilica having a function, such as a refractive-index controlling function, a light absorbing function, a light emitting function, and a charge transferring function. Another object is to provide an organosilica obtained from the organosilane compound.

The present inventors have devoted themselves to studies so as to achieve the above object. As a result, the present inventors have discovered an organosilane compound with a certain organic group being contained as its skeleton organic group. The above-mentioned organic group includes a phenylene group, a biphenylylene group, a naphthylene group, a pyridylene group, a vinylene group, or an ethynylene group. Then, the present inventors have also discovered that use of such an organosilane compound facilitates the synthesis of an organosilica having various functions, such as a refractive-index controlling function, a light absorbing function, a light emitting function, and a charge transferring function. The synthesis of the organosilica with use of the organosilane compound can be accomplished through a commonly-used organic synthetic reaction, for example, a coupling reaction including Suzuki, Sonogashira, Negishi, Kumada-Tamao, Kosugi-Migita-Stille, Hiyama, and amination reactions. These discoveries have led the inventors to complete the present invention.

To be more specific, a first aspect of the present invention provides an organosilane compound (a first organosilane compound) expressed by any one of the following general formulae (1) to (7):

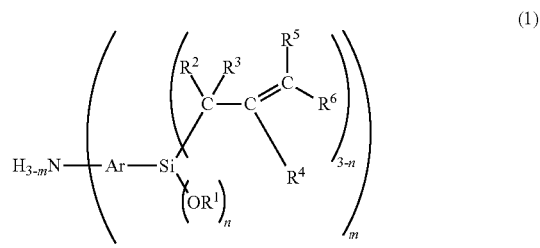
(1)

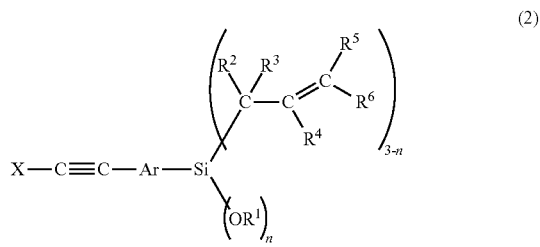
(2)

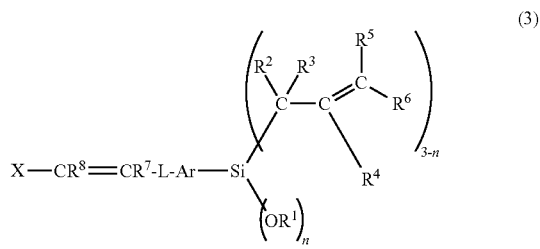
(3)

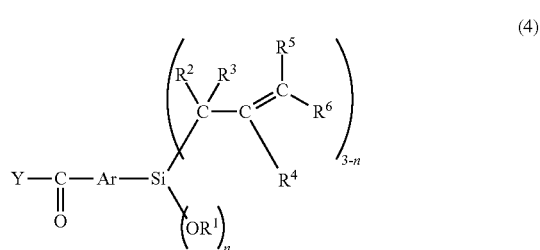
(4)

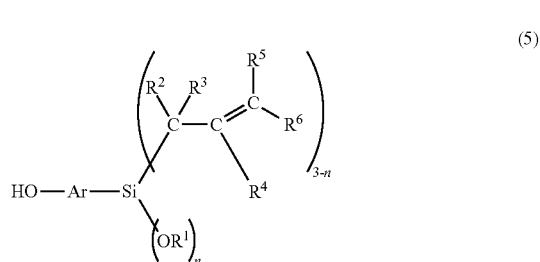
(5)

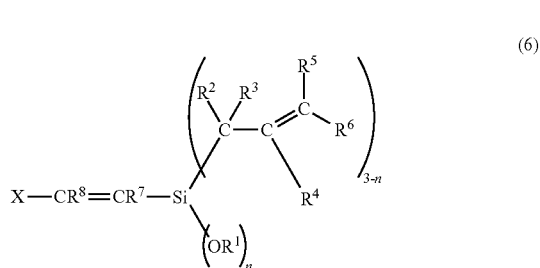
(6)

-continued

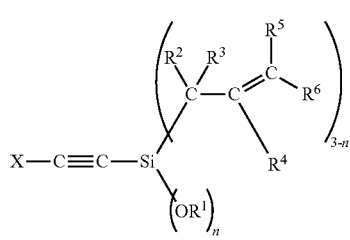
(7)

(wherein: Ar represents any one divalent aromatic organic group selected from the group consisting of a phenylene group, a biphenylylene group, a naphthylene group, and a pyridylene group; $R^1$ represents any one of a hydrogen atom and alkyl groups having 1 to 4 carbon atoms; $R^2$ to $R^8$, which may be either identical to or different from each other, each represent any one of a hydrogen atom, a methyl group, an ethyl group, a propyl group, a butyl group, an isopropyl group, a pentyl group, a hexyl group, and a cyclohexyl group; n represents an integer in a range from 0 to 2; m represents an integer in a range from 1 to 2; L represents any one of a single bond and a divalent organic group selected from the group consisting of an ether group, an ester group, and an amide group; X represents any one of a hydrogen atom, a halogen atom, and a trialkylsilyl group; and Y represents any one of a hydrogen atom, a hydroxy group, an alkyl group having 1 to 10 carbon atoms, and a univalent aromatic organic group).

In the first organosilane compound of the present invention, $R^1$ in the general formulae (1) to (7) preferably represents any one of a methyl group and an ethyl group.

In addition, in the first organosilane compound of the present invention, each of $R^7$ and $R^8$ in the general formulae (3) and (6) preferably represents any one of the hydrogen atom and the methyl group.

Moreover, in the first organosilane compound of the present invention, L in the general formula (3) preferably represents any one of the single bond and the amide group.

Furthermore, in the first organosilane compound of the present invention, X in the general formulae (2), (3), (6), and (7) preferably represents any one of the hydrogen atom and the halogen atom.

Still furthermore, in the first organosilane compound of the present invention, Y in the general formula (4) preferably represents any one of the hydrogen atom, the hydroxy group, and a pyridyl group.

Another aspect of the present invention provides an organosilane compound (a second organosilane compound) expressed by any one of the following general formulae (8) to (12):

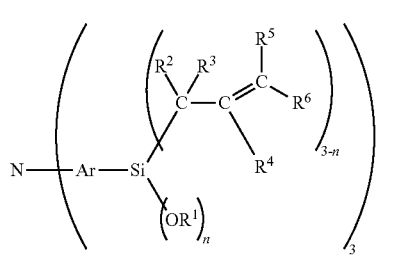
(8)

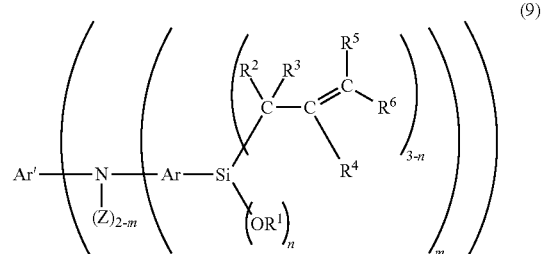
(9)

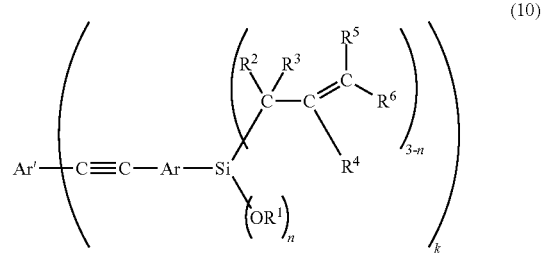
(10)

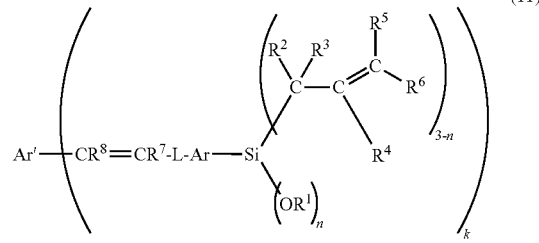
(11)

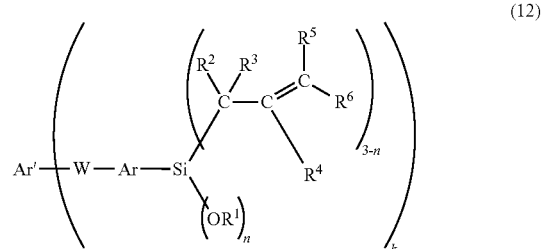
(12)

(wherein: Ar represents any one divalent aromatic organic group selected form the group consisting of a phenylene group, a biphenylylene group, a naphthylene group, and a pyridylene group; $R^1$ represents any one of a hydrogen atom and alkyl groups having 1 to 4 carbon atoms; $R^2$ to $R^8$, which may be either identical to or different from each other, each represent any one of a hydrogen atom, a methyl group, an ethyl group, a propyl group, a butyl group, an isopropyl group, a pentyl group, a hexyl group, and a cyclohexyl group; n represents an integer in a range from 0 to 2; m represents an integer in a range from 1 to 2; L represents any one of a single bond and a divalent organic group selected from the group consisting of an ether group, an ester group, and an amide group; k represents an integer in a range from 1 to 6; Ar' represents an aromatic organic group having a valency of k and containing at least one aromatic ring selected from the group consisting of a benzene ring, a naphthalene ring, an anthracene ring, a pyridine ring, a carbazole ring, and a fluorene ring; Z represents any one of a hydrogen atom, a hydroxy group, an alkyl group, and a univalent aromatic organic group; and W represents a divalent organic group containing any one of an ether group and a carbonyl group).

In the second organosilane compound of the present invention, Ar' in the general formulae (8) to (12) preferably represents an organic group expressed by any one of the following general formulae (13) to (23):

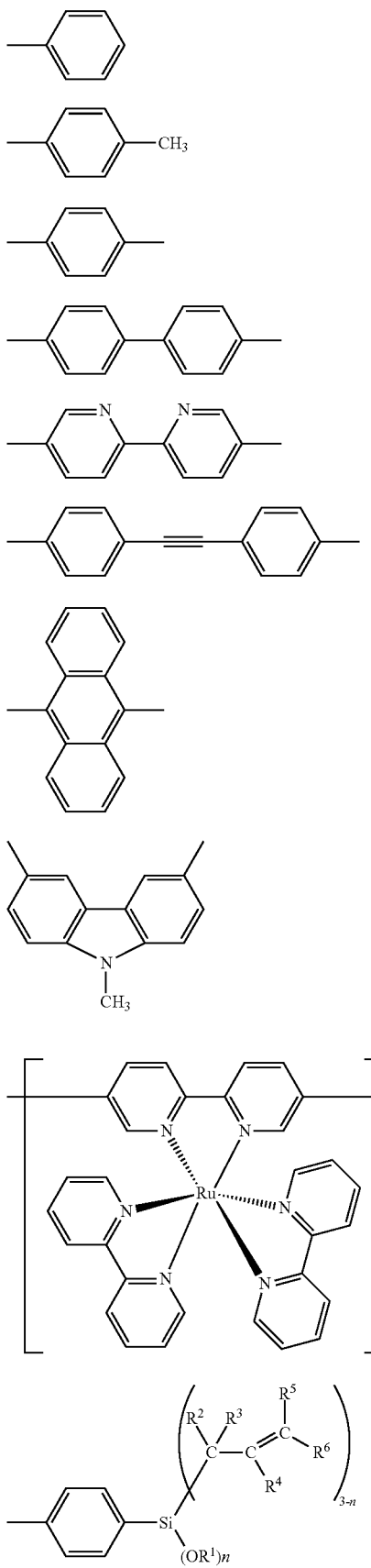

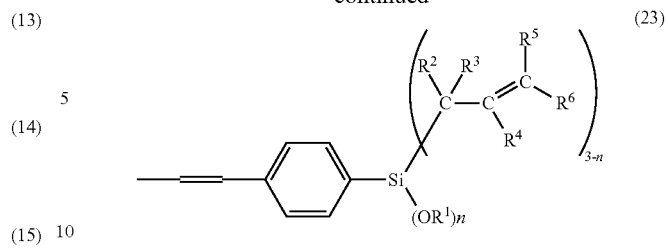

(wherein: A⁻ in the formula (21) represents a counter anion; $R^1$ to $R^6$ and n in the formulae (22) and (23) are identical respectively to $R^1$ to $R^6$ and n in the general formulae (8) to (12)).

In addition, in the second organosilane compound of the present invention, $R^1$ in the general formulae (8) to (12) preferably represents any one of a methyl group and an ethyl group.

Moreover, in the second organosilane compound of the present invention, Z in the general formula (9) preferably represents any one of a methyl group, an ethyl group, a propyl group, an isopropyl group, a phenyl group, and a biphenyl group.

Furthermore, in the second organosilane compound of the present invention, $R^7$ and $R^8$ in the general formula (11) each preferably represent anyone of the hydrogen atom and the methyl group.

Still furthermore, in the second organosilane compound of the present invention, L in the general formula (11) preferably represents any one of the single bond and the amide group.

Still even furthermore, in the second organosilane compound of the present invention, W in the general formula (12) preferably represents any one of the ether group and a ketone group.

Another aspect of the present invention provides an organosilica (a first organosilica) obtained by polymerizing at least one kind of the first organosilane compounds of the present invention.

Another aspect of the present invention provides an organosilica (a second organosilica) obtained by polymerizing at least one kind of the second organosilane compounds of the present invention.

According to the present invention, it is possible to provide an organosilane compound which is useful for a synthesis of an organosilica having a function, such as a refractive-index controlling function, a light absorbing function, a light emitting function, and a charge transferring function. Additionally, it is possible to provide an organosilica obtained from the organosilane compound.

DETAILED DESCRIPTION OF THE PREFERRED EMBODIMENTS

Figure 1:
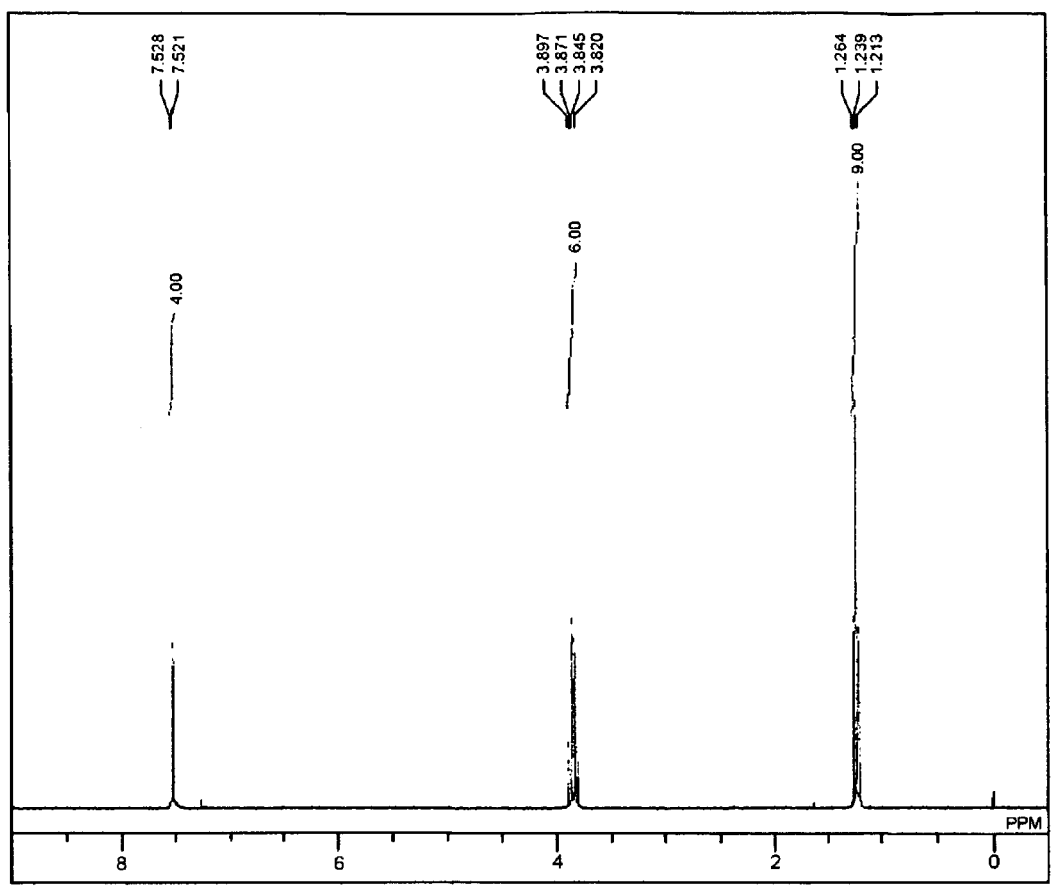
FIG. 1 is a graph showing a ¹H NMR of a compound obtained in Synthesis example 8 (4-bromo-triethoxysilylbenzene).

Hereinafter, the present invention will be specifically described in line with preferred embodiments thereof.

[First Organosilane Compound]

A first organosilane compound of the present invention is expressed by any one of the following general formulae (1) to (7):

(General Formulae (1) to (7))

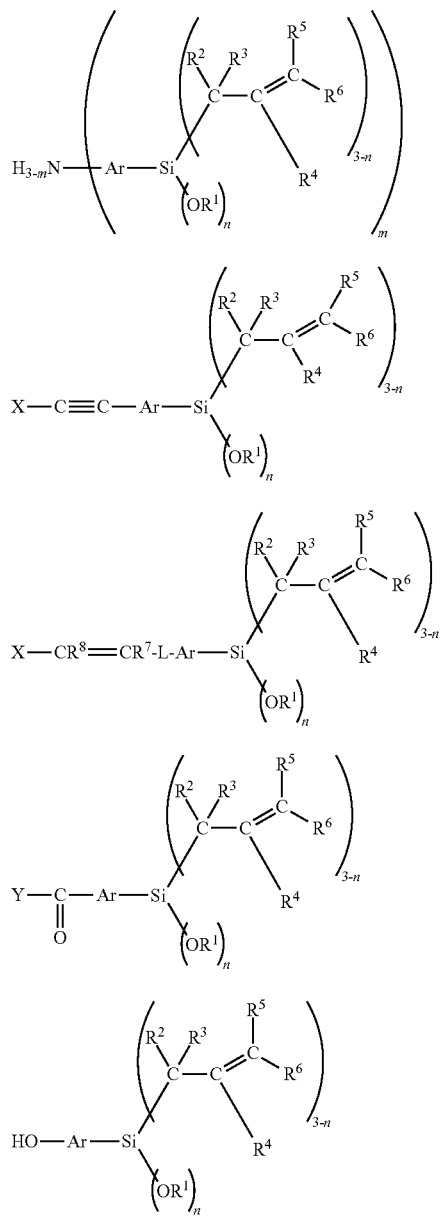

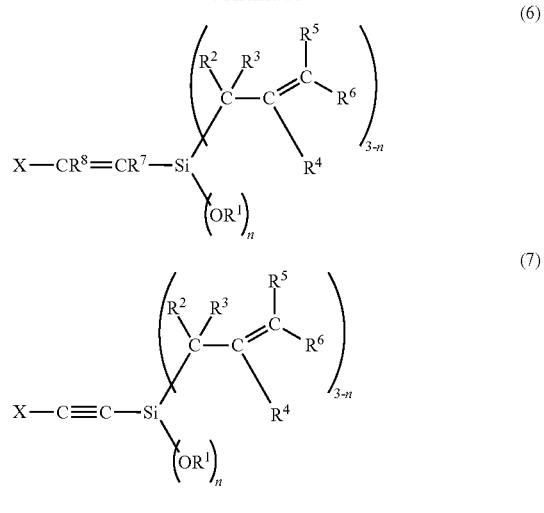

In the general formulae (1) to (5), Ar represents any one divalent aromatic organic group selected from the group consisting of a phenylene group, a biphenylylene group, a naphthylene group, and a pyridylene group. Such a divalent aromatic organic group represented by Ar is preferably the phenylene group, the biphenylylene group, and the naphthylene group from the viewpoint of optical application, and preferably the pyridylene group from the viewpoints of the charge transfer, the catalysis, and the incorporation with a metal.

In the general formulae (1) to (7), $R^1$ represents any one of a hydrogen atom and alkyl groups having 1 to 4 carbon atoms. Such an alkyl group having 1 to 4 carbon atoms selected as $R^1$ includes a methyl group, an ethyl group, a propyl group, an isopropyl group, a butyl group, a sec-butyl group, and a tert-butyl group. From the viewpoint of an efficient synthesis of an organosilica through hydrolysis and polycondensation reaction, the methyl group or the ethyl group are preferable.

In the general formulae (1) to (7), n represents an integer in a range from 0 to 2. Accordingly, in the above general formulae (1) to (7), the number of groups which are bound to the silicon atom (Si) and which are represented by —$OR^1$ is in a range from 0 to 2. The value of n is preferably an integer in a range from 1 to 2 from the viewpoint that the organosilane compound with the number n being an integer in a range from 1 to 2 enhances the reactivity during the production of organosilica. Moreover, it is more preferable that n=1 in view of the compatibility between the stability of the compound when it is stored and the reactivity when the organosilica is produced.

In the general formulae (1) to (7), the substituents represented by $R^2$ to $R^8$, which may be identical to or different from each other, each represent a hydrogen atom, a methyl group, an ethyl group, a propyl group, a butyl group, an isopropyl group, a pentyl group, a hexyl group, or a cyclohexyl group. In the case where $R^2$ to $R^6$ are substituents other than the above-mentioned substituents, it is difficult for an allyl group having the substituent represented by $R^2$ to $R^6$ to be detached from the silica skeleton during the synthesis of an organosilica. As a result, it tends to be difficult to form a stable siloxane binding (Si—O—Si) at a sufficient level. In addition, when the substituents represented by $R^7$ and $R^8$ in the general formulae (3) and (6) are substituents other than the above-mentioned ones, organic synthetic reaction utilizing the end group X tends to be difficult. It is preferable that the substituents represented by $R^7$ and $R^8$ be any one of the hydrogen atom and the methyl group in view of the securing of high reactivity for the end group X.

In the general formulae (2), (3), (6), and (7), X represents any one of a hydrogen atom, a halogen atom, and trialkylsilyl group. Any one of the hydrogen atom and the halogen atom is preferable for the X in view of the versatility as a raw material for organic synthesis.

In the general formula (4), Y represents any one of a hydrogen atom, a hydroxy group, alkyl groups having 1 to 10 carbon atoms, and a univalent aromatic organic group. The alkyl group is selectable here as Y has to have 1 to 10 carbon atoms (more preferably, 1 to 4 carbon atoms). The alkyl group may have either a straight-chain structure or a branched-chain structure. The alkyl group with 1 to 10 carbon atoms is preferably any one of a methyl group, an ethyl group, a propyl group, and a butyl group from the viewpoint of application to various organic synthetic reactions. The univalent aromatic organic group that is selectable as Y is preferably a phenyl group, a naphthyl group, a pyridyl group, an anthryl group, a carbazolyl group, an imidazolyl group, or the like. The especially preferable Y is any one of the hydrogen atom, the hydroxy group, and the pyridyl group from the viewpoint of a synthesis of a functional molecule through unsaturated bonding and introduction of a heteroatom.

In the general formula (3), L represents any one of a single bond and a divalent organic group selected from a group consisting of an ether group, an ester group, and an amide group. The preferable L is any one of the single bond and the amide group from the view point of synthesis of a conjugated organic molecule.

In the general formula (1), m represents an integer of 1 or 2. The preferable m is 1 from the viewpoint of the versatility of a raw material for organic synthesis.

Next, a description will be given of preferred methods of producing the first organosilane compound of the present invention.

Firstly, a description will be given of a preferred method of producing the organosilane compound expressed by the general formula (1). An example of the preferred method of producing the organosilane compound expressed by the general formula (1) is as follows. A raw-material compound expressed by the following general formula (24):

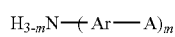  (24)

(where: Ar represents any one of divalent aromatic organic group selected from the group consisting of a phenylene group, a biphenylylene group, a naphthylene group, and a pyridylene group; A is a halogen atom; and m represent an integer of either 0 or 1) is caused to react with a silane compound expressed by the following general formula (25)

  (25)

(where $R^1$ represents any one of a hydrogen atom and alkyl groups having 1 to 4 carbon atoms). Thus, the substituent denoted by -A in the general formula (24) is substituted for the substituent denoted by —Si(OR$^1$)$_3$ in the general formula (25) so as to produce a precursor compound. Then, the precursor compound thus obtained is allylated, so that an organosilane compound is obtained.

Ar and m in the general formula (24) are identical to the respective ones described in the general formula (1). In the general formula (24), A represents a halogen atom, and preferably is either a bromine atom or an iodine atom since these elements are more reactive. $R^1$ in the general formula (25) is identical to the one described in the general formula (1). More preferable $R^1$ is either a methyl group or an ethyl group from the viewpoint of easiness in handling the compound.

The way of producing the raw-material compound expressed by the general formula (24) is not limited to a particular method, and a known method can be employed appropriately for the purpose. In addition, the way of causing the reaction between the raw-material compound expressed by the general formula (24) and the silane compound expressed by the general formula (25) is not limited to a particular method. Any known method can be appropriately employed as long as the method to be employed is capable of substituting the substitute denoted by -A in the general formula (24) for the substitute denoted by —Si (OR$^1$)$_3$ in the general formula (25).

Next, a description will be given of a preferred method to be employed as a step of obtaining the precursor compound. An example of such a method as the step is as follows. Firstly, the raw-material compound expressed by the general formula (24) is mixed with a [Rh(CH$_3$CN)$_2$(cod)]BF$_4$ complex and Bu$_4$NI under a nitrogen atmosphere at the room temperature, and the resultant mixture is then added with a solvent to produce a mixed liquid. The resultant mixed liquid is added with triethylamine and DMF to make a mixed solution. Subsequently, the silane compound expressed by the general formula (25) is added dropwise to the mixed solution at 0° C., and the resultant solution is then stirred thoroughly at 80° C. for approximately 1 hour to 2 hours, to produce a crude product. Thereafter, the precursor compound is obtained by removing the solvent from the crude product.

The solvent mixed with the raw-material compound expressed by the general formula (24) includes dimethylformamide (DMF), acetonitrile, N-methyl-2-pyrrolidone (NMP), and dioxane.

The way of allylating the precursor compound is not limited to a particular method, and a known method can be employed appropriately for the purpose. For example, the following method can be employed. Firstly, after the precursor compound is obtained as described above, the precursor compound is added with an allylating agent, such as allylmagnesium bromide [CH$_2$=CH—CH$_2$MgBr], under a nitrogen atmosphere at a temperature in a range from approximately −10° C. to 0° C. to produce a mixture. Then, the mixture thus obtained is stirred thoroughly at room temperature (approximately at 25° C.) for approximately 5 hours to 20 hours. The mixture thus stirred is then cooled down at approximately −10° C. to 0° C. After that, an organic layer is separated from the mixture. Then, the organic layer thus obtained is then washed with a washing solution (for example, NaHCO$_3$, NaCl), and dried. In this way, the precursor compound is allylated.

Next, a description will be given of a preferred method of producing the organosilane compound expressed by the general formulae (2) to (5). What follows is an example of the preferred method of producing the organosilane compound expressed by the general formulae (2) to (5). Firstly, a raw-material compound expressed by the following general formula (26):

  (26)

(where: Ar represents any one divalent aromatic organic group selected from the group consisting of a phenylene group, a biphenylylene group, a naphthylene group, and a pyridylene group; the two As, which may be either identical to or different from each other, each represent halogen atom) is caused to react with a compound expressed by the above general formula (25) to produce a precursor compound expressed by the following general formula (27):

 (27)

(where: Ar represents any one divalent aromatic organic group selected from the group consisting of a phenylene group, a biphenylylene group, a naphthylene group, and a pyridylene group; A represents a halogen atom; and $R^1$ represents any one of a hydrogen atom and an alkyl group having 1 to 4 carbon atoms). The resultant compound expressed by the general formula (27) is then allylated. After that, by a known method, such as the Grignard reaction, the substituent denoted by -A is substituted for a substituent expressed by the following general formulae (28) to (31):

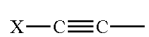 (28)

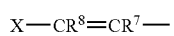 (29)

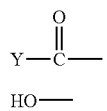 (30)

(31)

(where: $R^7$ and $R^8$ may be either identical to or different from each other; and each of $R^7$ and $R^8$ represents any one of a hydrogen atom, a methyl group, an ethyl group, a propyl group, a butyl group, an isopropyl group, a pentyl group, a hexyl group, and a cyclohexyl group; X represents any one of a hydrogen atom, a halogen atom, and a trialkylsilyl group; Y represents any one of a hydrogen atom, a hydroxy group, alkyl groups having 1 to 4 carbon atoms, and a univalent aromatic organic group selected from the group consisting of a phenyl group, a naphthyl group, a pyridyl group, an anthryl group, a carbazolyl group, and an imidazolyl group).

$R^7$, $R^8$, X, and Y in the general formulae (26) to (31) are identical to the respective ones in the general formulae (1) to (7). The A in the general formulae (26) and (27) is identical to the one in the general formula (24). The way of allylating the precursor compound in the preferred method of producing the organosilane compound expressed by the general formulae (2) to (5) is not particularly limited, and a known method can be employed appropriately. For example, a method that is similar to the method of allylating described in the method of producing the organosilane compound expressed by the general formula (1) can be employed.

The way of substituting the substituent denoted by -A in the general formula (27) for the substituent expressed by the general formulae (28) to (31) is not particularly limited, and a known method can be employed appropriately for the purpose. As an example of the substituting method, a case where the substituent denoted by -A in the general formula (27) is substituted for a substituent expressed by the general formula (30) will be described. In the method, a compound containing magnesium (for example, i-PrMgA, t-BuMgA: where A is a halogen) is added dropwise to a THF solution of a compound expressed by the general formula (27) so as to produce a Grignard solution. Then, DMF is added dropwise to the Grignard solution at −30° C., and the mixture thus obtained is stirred under a nitrogen atmosphere at room temperature for approximately 5 hours to 20 hours. After that, an organic layer is separated from the mixture. The organic layer thus obtained is then washed with a washing solution (for example, $NaHCO_3$, NaCl), and dried. The substitution is accomplished in this way.

Next, a description will be given of another preferred method of producing the organosilane compound expressed by the general formula (2). The example of this preferred method of producing the organosilane compound expressed by the general formula (2) is as follows. Firstly, the compound expressed by the general formula (27) is obtained, and is then allylated. The compound thus allylated is caused to react with a compound expressed by the following general formula (32):

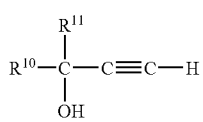 (32)

(where $R^{10}$ and $R^{11}$ represent alkyl groups) to synthesize a compound expressed by the following general formula (33):

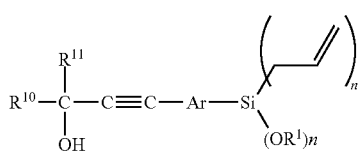 (33)

(where: $R^1$ represents any one of a hydrogen atom and alkyl groups having 1 to 4 carbon atoms; $R^{10}$ and $R^{11\prime\prime\prime}$ represent alkyl groups; and n represents an integer in a range from 0 to 2). The compound thus synthesized is then hydrolyzed to produce an organosilane compound expressed by the general formula (2).

$R^{10}$ and $R^{11}$ in the general formulae (32) and (33) represent alkyl groups. Each of the alkyl groups is not limited to a particular kind of alkyl groups, but is preferably a lower alkyl group having 1 to 4 carbon atoms from the viewpoint of easiness in synthesis. In addition, the way of causing the compound expressed by the general formula (32) to react with the compound expressed by the general formula (27) that has been allylated beforehand is not particularly limited. A known method can be appropriately employed as long as these compounds can be reacted with each other by the method to be employed. In addition, the way of the hydrolysis is not particularly limited, and a known method can be appropriately employed.

Next, a description will be given of another preferred method of producing the organosilane compound expressed by the general formula (3). An example of this preferred method of producing the organosilane compound expressed by the general formula (3) is as follows. Firstly, the organosilane compound expressed by the general formula (1) is obtained. The organosilane compound thus obtained is caused to react with a compound expressed by the following general formula (34):

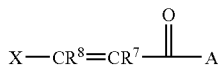 (34)

(where: $R^7$ and $R^8$ may be either identical to or different from each other; and each of $R^7$ and $R^8$ represents any one of a hydrogen atom, a methyl group, an ethyl group, a propyl group, a butyl group, an isopropyl group, a pentyl group, a hexyl group, and a cyclohexyl group; X represents any one of a hydrogen atom, a halogen atom, and a trialkylsilyl group; and A represents a hydrogen atom) to produce an organosilane compound expressed by the general formula (3) with the L being an amide. The n, $R^7$, $R^8$, and X in the general formula (34) are identical to the respective ones described in the general formulae (1) to (7). The $R^{10}$ and $R^{11}$ in the general formula (34) are identical to the respective ones described in the general formulae (32) and (33). The A in the general formula (34) is identical to the one described in the general formula (24). The way of causing reaction between the organosilane compound expressed by the general formula (1) and the compound expressed by the general formula (34) is not particularly limited. A known method that is capable of causing the reaction between these compounds can be appropriately employed.

Next, a description will be given of a preferred method of producing the organosilane compound expressed by the general formulae (6) and (7). An example of the preferred method of producing organosilane compound expressed by the general formulae (6) and (7) is as follows. An organic metal compound having either an alkynyl group or an alkenyl group—commonly the Grignard reagent or an organolithium reagent—is made to react with alkoxysilane. Then, an allylating treatment is carried out by using allylmagnesium bromide or the like. After that, an organic layer is separated. Then, the organic layer is dried. Thus, the organosilane compound expressed by the general formulae (6) and (7) is obtained.

Descriptions have been given thus far of preferred methods of producing the organosilane compounds expressed by the general formulae (1) to (7), but a method of producing the organosilane compounds expressed by the general formulae (1) to (7) is not limited to these methods described above. Any method can be appropriately employed as long as the organosilane compounds expressed by the general formulae (1) to (7) can be produced by the method.

[Second Organosilane Compound]

A second organosilane compound according to the present invention is expressed by any one of the following general formulae (8) to (12):

(General Formulae (8) to (12))

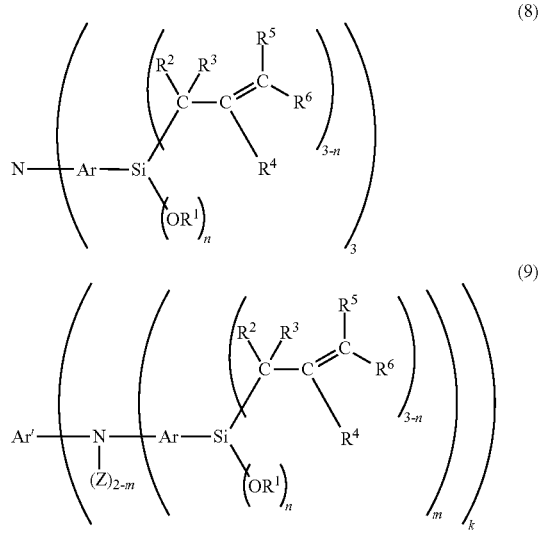

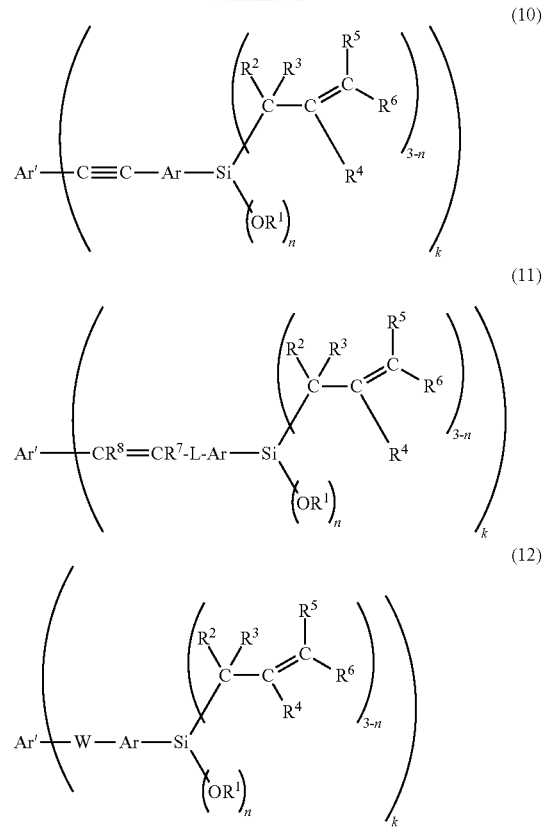

Ar, $R^1$ to $R^8$, L, n, and m in the general formulae (8) to (12) are identical to the respective ones described in the first organosilane compound of the present invention.

In the general formulae (9) to (12), k represents an integer in a range from 1 to 6. The value of k is preferably in a range from 2 to 6 from the viewpoint of the synthesizing of an organosilica composite material having been adequately bridged.

In the general formulae (8) to (12), Ar' represents an aromatic organic group having a valency of k and containing at least one aromatic ring selected from the group consisting of a benzene ring, a naphthalene ring, an anthracene ring, a pyridine ring, a carbazole ring, and a fluorene ring. The aromatic organic group having a valency of k represented by Ar' is not limited to a particular group, as long as the aromatic organic group contains at least one aromatic ring selected from the group consisting of a benzene ring, a naphthalene ring, an anthracene ring, a pyridine ring, a carbazole ring, and a fluorene ring. Examples of such aromatic organic groups having a valency of k are a phenyl group, a biphenyl group, an anthryl group, a pyridyl group, a carbazole group, a fluorene group, a phenylene group, a biphenylene group, a terphenyl group, a triphenylene group, a triphenylamine group, a triphenylbenzene group, a tetraphenylpyrene group, and a hexaphenylbenzene group. Each of such aromatic organic groups having a valency of k may include a substituent. Meanwhile, examples of the substituent that the aromatic organic group may include are a methyl group, an ethyl group, a methoxy group, an ethoxy group, a nitro group, a halogen group, a cyano group, a hydroxy group, an alkenylene group having 2 to 18 carbon atoms, an alkoxydiallylsilyl group, dialkoxyallylsilyl group, and the like. In addition, the aromatic organic group having a valency of k may form a complex. In such a complex, for example, a coordinate covalent bond is formed between a metal atom and the nitrogen atom on a pyridine ring in the case where the aromatic ring is the pyridine ring. In a case where the aromatic organic group having a valency of k forms a complex, a metal atom that is capable of being the metal center of the complex is any one of: rare metal elements such as ruthenium, rhenium, and iridium; first transition metal elements, such as iron, cobalt, and nickel; and lanthanoid elements, such as europium and terbium. Preferable ones are ruthenium, rhenium, iridium, osmium, iron, cobalt, nickel, copper, zinc, rhodium, palladium, silver, and platinum. A ligand that forms a coordinate covalent bond with the metal center are not only the aromatic groups that have been mentioned above but also bipyridine, terpyridine, phenanthroline, phenylpyridine, acetylacetone, dibenzylideneacetone, phosphine, and halogen. Preferable ones are bipyridine, phenylpyridine, and phosphine. In addition, examples of the counter anion to form such a complex are a $PF_6$ ion, $CF_3CF_2CF_2COO$ ion, a $SbF_6$ ion, a $BF_4$ ion, a triflate ion, a halogen ion, and the like.

Among the aromatic organic groups having a valency of k denoted by Ar', what is more preferable from the viewpoint of high-efficient light emission and charge transfer is any one of the organic groups expressed by the following general formulae (13) to (23):

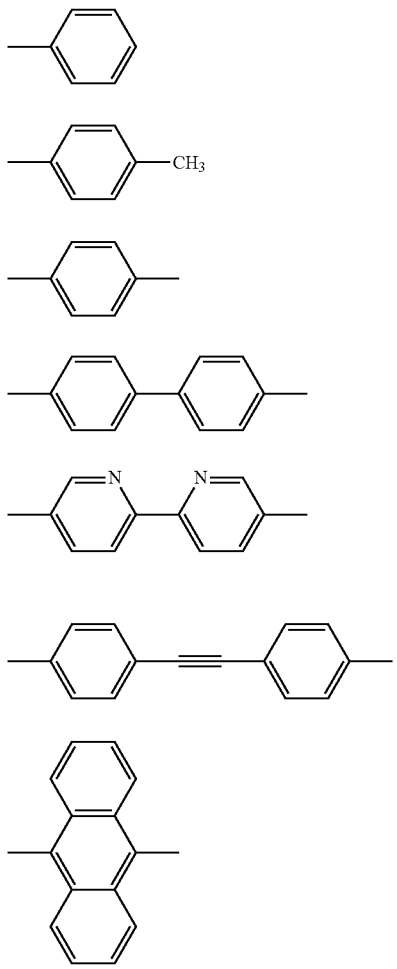

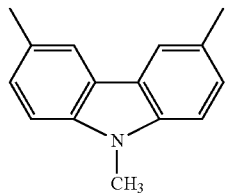

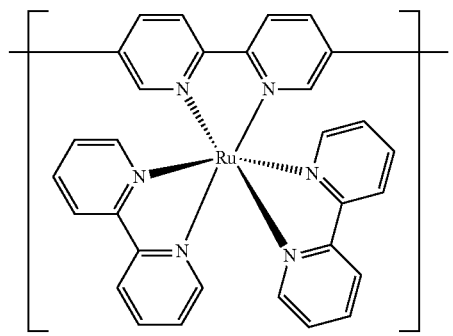

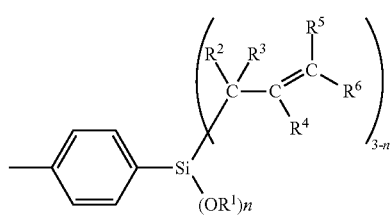

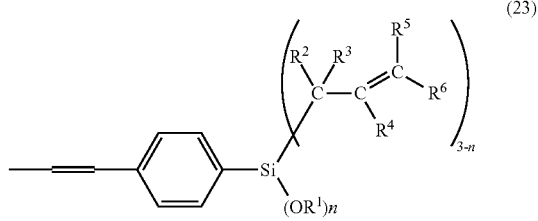

(in formula (21), $A^-$ represents the counter anion; in formulae (22) and (23), $R^1$ to $R^6$, and n are identical to the respective ones in the general formulae (8) to (12)). Note that the counter anion denoted by $A^-$ in the general formula (21) is similar to the counter anion in the case where the aromatic organic group having a valence of k is a complex.

In the general formula (9), Z represents any one of a hydrogen atom, a hydroxy group, an alkyl group, and a univalent aromatic organic group. The alkyl group selectable as Z is not limited to a particular type, but may have either a straight-chain structure or a branched-chain structure. In addition, the alkyl group for z preferably has 1 to 18 carbon atoms, and more preferably has 1 to 12 carbon atoms. When the number of carbon atoms exceeds the above-mentioned upper limit, a compound containing such an alkyl group tends to be difficult to use as a raw material to synthesize an orderly-arranged organosilica. Specific examples of the alkyl group selectable as Z are a methyl group, an ethyl group, a propyl group, an isopropyl group, a butyl group, a sec-butyl group, a tert-butyl group, a pentine group, a hexyl group, a decyl group, a dodecyl group, and the like. What is preferable from the viewpoint of the usage as a raw material to synthesize an organosilica complex is the methyl group, the ethyl group, the propyl group, and the isopropyl group.

Examples of the univalent aromatic organic group selectable as Z are a phenyl group, a biphenyl group, a naphthyl group, an anthryl group, and the like. What is preferable from the viewpoint of the application to the material for charge transfer is the phenyl group and the biphenyl group.

In the general formula (12), W represents a divalent organic group containing either an ether group or a carbonyl group. What is preferable for W from the viewpoint of the chemical stability of the compound is the ether group or a ketone group.

Next, a description will be given of a preferred method of producing the second organosilane compound of the present invention.

Firstly, a description will be given of a preferred method of producing the organosilane compound expressed by the general formula (8). An example of the preferred method of producing the organosilane compound expressed by the general formula (8) is as follows. A raw-material compound expressed by the following general formula (35):

(where: Ar represents any one divalent aromatic organic group selected from the group consisting of a phenylene group, a biphenylylene group, a naphthylene group, and a pyridylene group; and A represents a halogen atom) is caused to react with a silane compound expressed by the following general formula (25):

$$H-Si(OR^1)_3 \quad (25)$$

(where $R^1$ represents either a hydrogen atom or an alkyl group having 1 to 4 carbon atoms). Thus, the substituent denoted by -A in the general formula (35) is substituted for the substituent denoted by $-Si(OR^1)_3$ in the general formula (25) to produce a precursor compound. The precursor compound thus obtained is then allylated to produce the organosilane compound.

Ar and A in the formula (35) are identical to the respective ones described in the general formulae (1) and (24). The way of producing the raw-material compound is not particularly limited, and a known method can be appropriately employed.

Next, a description will be given of a preferred method of producing the organosilane compound expressed by the general formulae (9) to (12). An example of the preferred method of producing the organosilane compound expressed by the general formulae (9) to (12) is as follows. The organosilane compound expressed by the general formulae (2) to (5) is caused to react with a compound expressed by the following general formula (36)

(where: k represents an integer in a range from 1 to 6; Ar' represents an aromatic organic group having a valency of k and containing at least one aromatic ring selected from the group consisting of a benzene ring, a naphthalene ring, an anthracene ring, a pyridine ring, a carbazole ring, and a fluorene ring; A represents a halogen atom) to produce the organosilane compound expressed by the general formulae (9) to (12).

The k and Ar' in the general formula (36) are identical to the respective ones in the general formulae (9) to (12). The A is identical to the one described in the general formula (24). The way of causing the reaction between the organosilane compound expressed in the general formulae (2) to (5) and the compound expressed by the general formula (36) is not particularly limited. A known reaction method can be appropriately employed as long as these compounds can be reacted with each other by the method to be employed. In an example of such a method, the organosilane compound expressed by the general formulae (2) to (5) is mixed with the compound expressed by the general formula (36) in a solvent under a nitrogen atmosphere at room temperature (approximately at 25° C.). The solvent to be used when the organosilane compound expressed by the general formulae (2) to (5) is mixed with the compound expressed by the general formula (36) is not limited to a particular solvent. Examples of such a solvent are toluene, tetrahydrofuran, dimethylformamide, benzene, acetonitrile, diethyl ether, ethanol, and the like. In addition, an example of a preferred method of producing the organosilane compound in the case of the Ar' in the general formulae (8) to (12) being a complex is as follows. Firstly, an organosilane compound is obtained by the method of producing the organosilane compound expressed by the general formulae (9) to (12) except that an aromatic organic group having a valency of k and containing a pyridine ring is selected as the Ar' in the general formula (36). Then, using a metal salt, a coordinate bond is formed between the nitrogen atom on the pyridine ring that exists in the organosilane compound and the metal atom in the metal salt. Thus, an organosilane compound in which Ar' is a complex is produced. The way of forming a coordinate bond between the nitrogen atom on the pyridine ring and the metal atom in the metal salt is not particularly limited, and a known method can be appropriately employed as long as a complex can be formed by the method. In addition, the kind of metal atoms and the kind of metal salts can also be changed so as to meet the needs of the design for the target compound.

The preferred method of producing the organosilane compound expressed by the general formulae (8) to (12) has been described thus far, but a method of producing the organosilane compounds expressed by the general formulae (8) to (12) is not limited to these methods described above. Any method can be appropriately employed as long as the organosilane compound expressed by the general formulae (8) to (12) can be produced by the method.

[Organosilica]

A first organosilica of the present invention is obtained by polymerizing at least one of the first organosilane compounds of the present invention. A second organosilica of the present invention is obtained by polymerizing at least one of the second organosilane compounds of the present invention.

When at least one of the first organosilane compounds or at least one of the second organosilane compounds of the present invention is polymerized (hydrolyzed and polycondensed), the allyl group (including an allyl group having a substituent) and the group denoted by $OR^1$ in the first or in the second organosilane compounds of the present invention are fundamentally detached. Then, in the detachment portion, a siloxane binding (Si—O—Si) is formed through the hydrolysis and the subsequent polycondensation reaction.

As has just been described above, the first or second organosilica of the present invention obtained by polymerizing the first or the second organosilane compound of the present invention has an organic group (Ar, Ar', or an organic group containing a vinylene group or an ethynylene group), a silicon atom (Si), and an oxygen atom (O) as the main components of the skeleton. In addition, the organosilica has a highly-bridged mesh structure.

The way of polymerizing the first or the second organosilane compound of the present invention is not particularly limited. It is, however, preferable that the first or the second organosilane compounds of the present invention be hydrolyzed and polycondensed under the presence of an acidic or basic catalyst upon using water or a mixture solvent of water and an organic solvent as the solvent. Examples of organic solvents that are preferably used are alcohol, acetone, and the like. When a mixture solvent is used, the content of the organic solvent is preferably in a range from approximately 5% by weight to 50% by weight. Examples of acidic catalysts to be used include, among others, a mineral acid, such as hydrochloric acid, nitric acid, and sulfuric acid. When an acidic catalyst is used, the solution is preferably acidic having a pH of 6 or below (more preferably in a range from 2 to 5). In addition, examples of basic catalysts to be used include sodium hydroxide, ammonium hydroxide, potassium hydroxide, and the like. When a basic catalyst is used, the solution is preferably basic having a pH of 8 or higher (more preferably in a range from 9 to 11).

The content, in terms of silica concentration, of the first and/or the second organosilane compounds of the present invention in the polymerization step is preferably in a range from 0.0055 mol/L to 0.33 mol/L, approximately. The reaction conditions (temperature, duration, and the like) in the polymerization step are not limited to particular conditions, and are selected appropriately in accordance with the type of the first and/or the second organosilane compounds to be used or the type of the target organosilica to be obtained. In general, it is preferable that the first and/or the second organosilane compounds of the present invention be hydrolyzed and polycondensed at approximately 0° C. to 100° C. for 1 hour to 48 hours.

Furthermore, the organosilica obtained by polymerizing the first organosilane compound or the second organosilane compound of the present invention generally has an amorphous structure. However, the organosilica thus obtained can have a periodic structure based on an ordered arrangement of the organic groups (an organic group containing Ar, Ar', a vinylene group, or an ethynylene group) in accordance with the synthesis conditions. Such periodicity depends on the molecular length of the first or the second organosilane compound to be used of the present invention. The preferable periodicity for the periodic structure is 5 nm or below. Such a periodic structure is maintained even after the first or the second organosilane compound of the present invention is polymerized. A proof of the formation of the periodic structure can be obtained through an X-ray diffraction (XRD) measurement. Specifically, the proof is a peak that appears in a region where the d value is 5 nm or below in the measurement. Even when such a peak is not observed in the XRD measurement, the periodic structure is partially formed in some cases. Such a periodic structure is formed, generally but not exclusively, with a layered structure to be described later.

To form such a periodic structure based on the ordered arrangement of the organic groups, certain synthesis conditions as follows are preferable.

(i) Since the periodic structure is formed as a result of the interaction among the first or the second organosilane compounds of the present invention, it is preferable that such interaction among the first or the second organosilane compounds of the present invention be increased. What is preferable to this end is the use of an organosilane compound containing organic groups that include Ar and/or Ar'.

(ii) The solution preferably has a pH of 1 to 3 (acidic) or a pH of 10 to 12 (basic), and more preferably has a pH of 10 to 12 (basic).

Moreover, in the method of producing the first or the second organosilica of the present invention, pores can be formed in the obtained organosilica by adding a surfactant to a reaction mixture in polymerization (hydrolysis and polycondensation) of the first or the second organosilane compound of the present invention. In other words, the micelle or liquid crystal structure of the surfactant serves as a template to form a porous material having pores.

It is preferable to use a surfactant together with the first and/or the second organosilane compound of the present invention. This is because the use of the surfactant enables the production of a mesoporous material having mesopores with a central pore diameter of 1 nm to 30 nm in a pore diameter distribution curve. The central pore diameter mentioned here is the pore diameter at the maximum peak of a curve (pore diameter distribution curve) in which values (dV/dD) obtained by differentiating the pore volume (V) by the pore diameter (D) are plotted to corresponding pore diameter (D). The central pore diameter can be obtained by the following method. A nitrogen gas is introduced while the porous material is cooled down to a liquid nitrogen temperature ($-196°$ C.). The amount of the adsorbed nitrogen gas is thus determined with a volumetrical method or a gravimetrical method. Subsequently, while the pressure of the nitrogen gas being introduced is gradually increased, the amount of adsorbed nitrogen gas is plotted to each equilibrium pressure. In this way, an adsorption isotherm is obtained. Using the adsorption isotherm, a pore diameter distribution curve can be calculated by a calculation method, such as a Cranston-Inklay method, a Pollimore-Heal method, and a BJH method.

It is preferable that at least 60% of the total pore volume of the mesoporous material be included within a range of $\pm 40\%$ of the central pore diameter in the pore diameter distribution curve. Such a mesoporous material satisfying this condition has highly uniform diameters of the pores thereof. The specific surface area of the mesoporous material is not limited to a particular value, but is preferably 700 $m^2/g$ or above. The specific surface area can be calculated as a BET specific surface area based on the adsorption isotherm by a BET isothermal adsorption equation.

Furthermore, the mesoporous material preferably has one or more peaks at a diffraction angle corresponding to the d value of 1.5 nm to 30.5 nm in the X-ray diffraction (XRD) pattern. The X-ray diffraction peak indicates that a periodic structure of a specific d value corresponding to the peak angle is present in the sample. Accordingly, the fact that one or more peaks are present at a diffraction angle corresponding to the d value of 1.5 nm to 30.5 nm means that the pores are orderly arranged at intervals in a range from 1.5 nm to 30.5 nm.

The pores in the mesoporous material are formed not only on the surface of the porous material but also in the inside thereof. The pore arrangement state (pore arrangement structure, or, simply, structure) in the porous material is not limited to a particular state, but it is preferable to have a 2d-hexagonal structure, a 3d-hexagonal structure, or a cubic structure. Alternatively, the pore arrangement structure may be a disordered pore arrangement structure.

In this case, the phrase that the porous material has a hexagonal pore arrangement structure means that the arrangement of the pores is of a hexagonal structure (see: S. Inagaki et. al., J. Chem. Soc., Chem. Commun., p. 680 (1993); S. Inagaki et al., Bull. Chem. Soc. Jpn., 69, p. 1449 (1996); Q. Huo et al., Science, 268, p. 1324 (1995)). Moreover, the phrase that the porous material has a cubic pore arrangement structure means that the arrangement of the pores is of a cubic structure (see: J. C. Vartuli et al., Chem. Mater., 6, p. 2317 (1994); Q. Huo et al., Nature, 368, p. 317 (1994)). In addition, the phrase that the porous material has a disordered pore arrangement structure means that the arrangement of the pores is irregular (see: P. T. Tanev et al., Science, 267, p. 865 (1995); S. A. Bagshaw et al., Science, 269, p. 1242 (1995); R. Ryoo et al., J. Phys. Chem., 100, p. 17718 (1996)). Furthermore, the cubic structure preferably has a Pm-3n, Ia-3d, Im-3m, or Fm-3m symmetry. The symmetrical property is to be determined on the basis of the notation of a space group.

In the case where the organosilica of the present invention has pores, the pores allow the porous materials to adsorb (by physical adsorption and/or chemical-bonding) a metal having a catalytic function and a functional element, such as a light-emitting compound and a pigment.

The surfactant used in obtaining the mesoporous material is not limited to a particular surfactant, but any one of cationic, anionic, and non-ionic surfactants can be used for the purpose. To be more specific, some examples of the surfactant are: a chloride, a bromide, an iodide, and a hydroxide of alkyltrimethylammonium, alkyltriethylammonium, dialkyldimethylammonium, benzylammonium, and the like; a fatty acid salt, alkylsulfonate, alkylphosphate, a polyethylene-oxide-based non-ionic surfactant, primary alkylamine, and the like. These surfactants are used alone or in combination of two or more kinds.

Among the above surfactants, the polyethylene oxide-based non-ionic surfactant includes ones having a hydrocarbon group as a hydrophobic component and a polyethylene oxide as a hydrophilic component, for example Such a surfactant that is preferably used is the one expressed by a general formula, for example, $C_nH_{2n+1}(OCH_2CH_2)_mOH$ where n is in a range from 10 to 30 and m is in a range from 1 to 30. Alternatively, esters of sorbitan and a fatty acid, such as oleic acid, lauric acid, stearic acid, and palmitic acid, or compounds formed by adding polyethylene oxide to these esters can also be used as the surfactant.

Furthermore, a triblock copolymer of polyalkylene oxide can also be used as the surfactant. Such a surfactant includes one made of polyethylene oxide (EO) and polypropylene oxide (PO), and expressed by a general formula $(EO)_x(PO)_y(EO)_x$. Here, x and y are the numbers of repetitions of EO and PO, respectively. It is preferable that x be in a range from 5 to 110 and y be in a range from 15 to 70, and more preferable that x be in a range from 13 to 106 and y be in a range from 29 to 70. The triblock copolymer includes $(EO)_{19}(PO)_{29}(EO)_{19}$, $(EO)_{13}(PO)_{70}(EO)_{13}$, $(EO)_5(PO)_{70}(EO)_5$, $(EO)_{13}(PO)_{30}(EO)_{13}$, $(EO)_{20}(PO)_{30}(EO)_{20}$, $(EO)_{26}(PO)_{39}(EO)_{26}$, $(EO)_{17}(PO)_{56}(EO)_{17}$, $(EO)_{17}(PO)_{58}(EO)_{17}$, $(EO)_{20}(PO)_{70}(EO)_{20}$, $(EO)_{80}(PO)_{30}(EO)_{80}$, $(EO)_{106}(PO)_{70}(EO)_{106}$, $(EO)_{100}(PO)_{39}(EO)_{100}$, $(EO)_{19}(PO)_{33}(E)_{19}$, and $(EO)_{26}(PO)_{36}(EO)_{26}$. These triblock copolymers are available from BASF Group, Sigma-Aldrich Corp., and the like. The triblock copolymer having desired x and y values can also be obtained in a small-scale production level.

It is also possible to use a star diblock copolymer formed by binding two chains of a polyethylene oxide (EO) chain-polypropylene oxide (PO) chain to each of two nitrogen atoms of ethylenediamine. Such a star diblock copolymer includes one expressed by a general formula $((EO)_x(PO)_y)_2NCH_2CH_2N((PO)_y(EO)_x)_2$ where x and y represent the numbers of repetitions of EO and PO, respectively. It is preferable that x be in a range from 5 to 110 and y be in a range from 15 to 70, and more preferable that x be in a range from 13 to 106 and y be in a range from 29 to 70.

Among the above surfactants, a salt (preferably a halide salt) of alkyltrimethylammonium $[C_pH_{2p+1}N(CH_3)_3]$ is preferably used because the mesoporous material having a high crystallinity can be obtained with this surfactant. In this case, the alkyltrimethylammonium preferably has an alkyl group having 8 to 22 carbon atoms. Some examples of the alkyltrimethylammoniums are octadecyltrimethylammonium chloride, hexadecyltrimethylammonium chloride, tetradecyltrimethylammonium chloride, dodecyltrimethylammonium bromide, decyltrimethylammonium bromide, octyltrimethylammonium bromide, and docosyltrimethylammonium chloride.

In order to produce the first or the second organosilica of the present invention using the above-described surfactant, the first and/or the second organosilane compound of the present invention is firstly hydrolyzed and polycondensed in the above-described solvent containing the surfactant. Thus obtained is a porous material precursor, which is an organosilica containing the surfactant. In this step, the concentration of the surfactant in the solution is preferably in a range from 0.05 mol/L to 1 mol/L. When the surfactant concentration is less than the lower limit, the formation of the pores tends to be incomplete. On the other hand, when the concentration exceeds the upper limit, the amount of the unreacted surfactant which remains in the solution is increased, and therefore the uniformity of the pores tends to be decreased.

Then, the surfactant contained in the porous material precursor thus obtained is removed to obtain a porous organosilica. In this step, some examples of the method for removing the surfactant are: (i) a method of removing the surfactant in which the porous material precursor is immersed in an organic solvent (for example, ethanol) having a high solubility to the surfactant; (ii) a method of removing the surfactant in which the porous material precursor is calcined at 250° C. to 550° C.; and (iii) an ion-exchange method in which the porous material precursor is immersed in an acidic solution and heated to exchange the surfactant with hydrogen ions.

Furthermore, the first and the second organosilicas of the present invention thus obtained can acquire a function, such as a refractive-index controlling function, a light absorbing function, a light emitting function, and a charge transferring function, when a type of the organosilane compound used is appropriately selected. Therefore, it is possible to suitably utilize the organosilicas of the present invention as a light emitting material, a charge-transfer material, a thin film, and the like.

Moreover, the first and second organosilicas of the present invention may be used in a powder form without any modification, but may be used after being molded as necessary. Any molding means can be employed, and some of the preferable means are extrusion, tablet molding, tumbling granulation, compression molding, and cold isostatic pressing (CIP). The form of the organosilicas can be determined in accordance with where and how the organosilicas are to be used. Some examples of the forms are columnar, granular, spherical, honeycomb, asperity, and corrugated forms.

Furthermore, the first and the second organosilicas of the present invention can be formed into a thin film by a method such as the following one. In order to obtain such a thin-film organosilica, the first and/or second organosilane compounds of the present invention are firstly stirred in an acidic solution (for example, an aqueous solution, such as hydrochloric acid and a nitric acid, or an alcohol solution) for a partial polymerization reaction (partial hydrolysis and partial polycondensation reaction) to obtain a sol solution including the partial polymer. Since the hydrolysis reaction of the first and/or second organosilane compounds of the present invention takes place more easily in a region low in pH, it is possible to accelerate the partial polymerization by reducing the pH of the reaction system. To this end, the pH is preferably 2 or below, and more preferably 1.5 or below. In this case, the reaction temperature can be approximately 15° C. to 25° C., and the reaction duration can be approximately 30 minutes to 90 minutes, for example.

Subsequently, the sol solution thus obtained is coated on a substrate, and thereby a thin-film organosilica is produced. The method of coating a substrate with the sol solution is not limited to a particular method, and various coating methods can be appropriately employed. An example of the coating method is a coating method with a bar coater, roll coater, gravure coater, or the like. Besides, a method utilizing a dip coating, spin coating, spray coating, or the like, may also be employed. Additionally, it is possible to form a patterned organosilica on a substrate by coating the sol solution with an inkjet method.

Thereafter, the obtained thin film is heated to approximately 70° C. to 150° C. and dried to accelerate the polycondensation reaction of the partial polymer. Thereby, a three-dimensional bridged structure is preferably formed. Note that the addition of the above-described surfactant to the sol solution enables the ordered pore structure to be formed in the thin-film organosilica.

EXAMPLES

Hereinafter, the present invention will be more specifically described on the basis of examples and comparative examples. However, the present invention is not limited to the following examples.

Synthesis Example 1

(S)-5,5'-Diethynyl-2,2'-bis(diphenylphosphinyl)-1,1'-binaphthyl was prepared as follows.

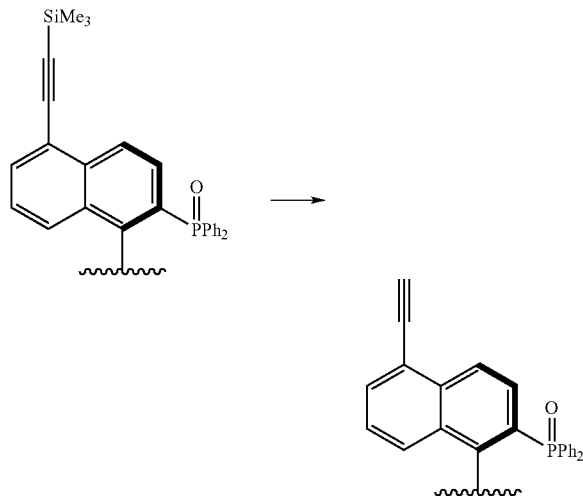

Firstly, 5,5'-trimethylsilylethynyl BINAP dioxide (301 mg, 0.355 mmol) was dissolved in dichloromethane (12 mL), and then tetrahydrofuran (THF) solution of 1.0-M tetrabutylammonium fluoride (0.78 mL, 0.781 mmol) was added dropwise. The resultant solution was then stirred at room temperature for 2 hours. Subsequently, the solvent in the solution was concentrated, a crude product thus obtained was purified by silica gel column chromatography (hexane/ethyl acetate=1/3)) and thus (S)-5,5'-diethynyl-2,2'-bis(diphenylphosphinyl)-1,1'-binaphthyl was obtained (218.4 mg, 88% yield).

The obtained compound was subjected to $^1$H NMR and $^{31}$P NMR measurements. The obtained results are shown below.

$^1$H NMR (CDCl$_3$) 8.43-8.39 (dd, J=8.6, 2.4 Hz, 2H), 7.74-7.66 (m, 4H), 7.60-7.49 (m, 4H), 7.43-7.21 (m, 16H), 6.74-6.66 (m, 4H), 3.46 (s, 2H);

$^{31}$P NMR (CDCl$_3$) 28.48

From the NMR measurement results, it was confirmed that the obtained compound was (S)-5,5'-diethynyl-2,2'-bis(diphenylphosphinyl)-1,1'-binaphthyl.

Example 1

(S)-5,5'-Bis(4-diallylethoxysilylphenylethynyl)-2,2'-bis(diphenylphosphinyl)-1,1'-binaphthyl was prepared as follows.

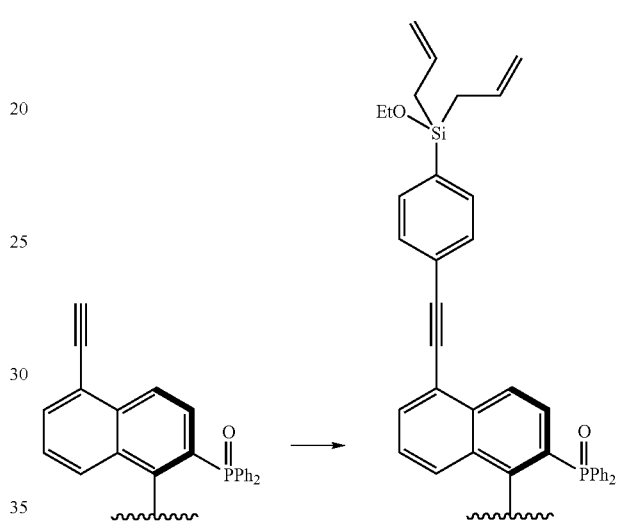

A first solution (8 mL) was prepared by dissolving (S)-5,5'-diethynyl-2,2'-bis(diphenylphosphinyl)-1,1'-binaphthyl (166.8 mg, 0.237 mmol) obtained in Synthesis example 1 in benzene. Then, 4-diallylethoxysilyliodobenzene (211.1 mg, 0.589 mmol), PdCl$_2$(PPh$_3$)$_2$ (17.5 mg, 0.025 mmol; Ph=phenyl), copper (I) iodide (CuI: 4.8 mg, 0.025 mmol) were dissolved in benzene (1 mL), and the resultant solution was added with triethylamine (0.21 ml, 1.50 mmol). After that, the first solution that was cooled down to 0° C. was added, and thus obtained was a second solution. The second solution thus obtained was stirred at 50° C. for 23 hours. Subsequently, the solvent in this second solution was concentrated. Then, a crude product thus obtained was purified by silica gel column chromatography (hexane/ethyl acetate (hexane/EtOAc)=1/1: Et=ethyl), and thus (S)-5,5'-bis(4-diallylethoxysilylphenylethynyl)-2,2'-bis(diphenylphosphinyl)-1,1'-binaphthyl was obtained (201.2 mg, 71% yield).

The obtained compound was subjected to $^1$H NMR and $^{31}$P NMR measurements. The obtained results are shown below.

$^1$H NMR (CDCl$_3$) 8.53-8.49 (dd, J=8.6, 2.4 Hz, 2H), 7.78-7.70 (m, 4H), 7.62-7.52 (m, 12H), 7.45-7.25 (m, 16H), 6.73 (d, J=4.3 Hz, 4H), 5.89-5.76 (m, 4H), 5.01-4.93 (m, 8H), 3.80 (q, J=6.8 Hz, 4H), 1.97 (d, J=8.1 Hz, 8H), 1.24 (t, J=6.8 Hz, 6H);

$^{31}$P NMR (CDCl$_3$) 28.68

From the NMR measurement results, it was confirmed that the obtained compound was (S)-5,5'-bis(4-diallylethoxysilylphenylethynyl)-2,2'-bis(diphenylphosphinyl)-1,1'-binaphthyl.

Example 2

4-(diallylethoxysilyl)aniline was prepared as follows.

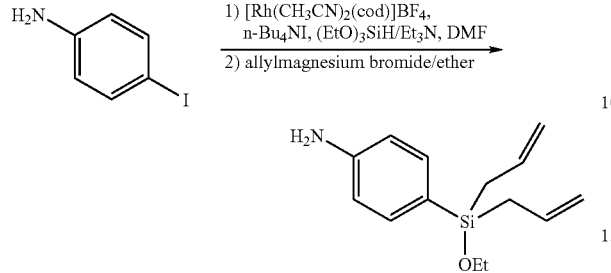

Firstly, distilled dimethylformamide (dist. DMF: 4 mL), distilled triethylamine (dist. Et$_3$N: 190 μL, 1.38 mmol), and triethoxysilane (169 μL, 0.92 mmol) are added dropwise to a mixture of 4-iodoaniline (100 mg, 0.46 mmol), [Rh(CH$_3$CN)$_2$(cod)]BF$_4$ (5.2 mg, 0.014 mmol: cod=1,5-cyclooctadiene), tetrabutylammoniumiodide (n-BU$_4$NI: 169 mg, 0.46 mmol). The resultant mixture was stirred under a nitrogen atmosphere at 80° C. for 1 hour to obtain a reaction mixture. Then, the solvent in the obtained reaction mixture was distilled away with a vacuum pump. A residue was extracted with ether, and then a salt thus formed was removed through a celite-filtration process. After that, an organic layer is collected, and the solvent in the organic layer is distilled away with an evaporator to obtain a crude product (I) (189 mg).

Subsequently, the obtained crude product was added directly with distilled ether (dist. ether: 2 mL) under a nitrogen atmosphere, and then 1-M allylmagnasium bromide (4 mL (solvent: ether), 4 mmol) was added dropwise at 0° C. to obtain a mixture. The mixture thus obtained was stirred under a nitrogen atmosphere, at room temperature for 16 hours, and then was cooled down by using a saturated aqueous solution of sodium acid carbonate (sat. NaHCO$_3$). After that, an organic layer was separated from the mixture while the aqueous layer was extracted with ether. The organic layer thus collected was washed with sodium acid carbonate and sodium chloride, and then the washed organic layer was dried with anhydrous magnesium sulfate (MgSO$_4$). The dried organic layer was then filtered, and concentrated to obtain a crude product (II). Then, the obtained crude product (II) was separated and purified by PTLC (hexane/EtOAc=3/1) to obtain 4-(diallylethoxysilyl)aniline (50.2 mg, 44% yield (in two steps)).

The obtained compound was subjected to $^1$H NMR and $^{13}$C NMR measurements. The obtained results are shown below.

$^1$H NMR (CDCl$_3$) δ7.36 (d, J=8.1 Hz, 2H), 6.68 (d, J=8.1 Hz, 2H), 5.91-5.74 (m, 2H), 4.98-4.86 (m, 4H), 3.75 (br, 2H), 3.73 (q, J=7.0 Hz, 2H), 1.90 (d, J=7.8 Hz, 4H) 1.48 (t, J=7.0 Hz, 3H).

$^{13}$C NMR (CDCl$_3$) δ147.9, 135.5, 133.6, 122.9, 114.44, 114.40, 59.1, 21.4, 18.4.

From the NMR measurement results, it was confirmed that the obtained compound was 4-(diallylethoxysilyl)aniline.

Example 3

1-acryloylamino-4-(diallylethoxysilyl)benzene was prepared as follows.

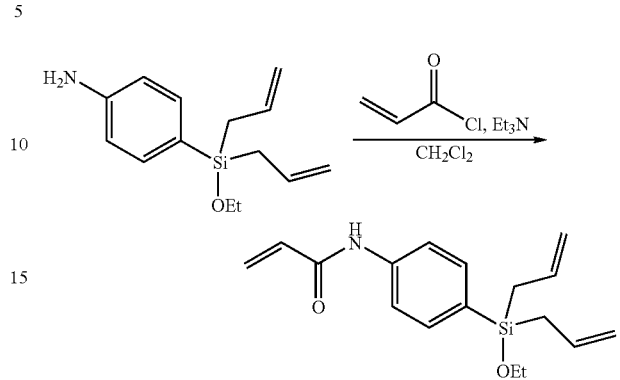

A solution of 4-(diallylethoxysilyl)aniline (153 mg, 0.62 mmol) and distilled dichloromethane (dist. CH$_2$Cl$_2$: 5 mL) was added with dist. Et$_3$N (86 μL, 0.62 mmol), and then acryloyl chloride (50 μL, 0.62 mmol) was added dropwise slowly at 0° C. The mixture thus obtained was stirred under a nitrogen atmosphere at 0° C. for 8 hours. After that, the solvent in the mixture was distilled without being heated to obtain a residue. Subsequently, the residue thus obtained was separated and purified by PTLC (hexane/EtOAc=2/1) to obtain 1-acryloylamino-4-(diallylethoxysilyl)benzene (110 mg, 59% yield).

The obtained compound was subjected to $^1$H NMR and $^{13}$C NMR measurements. The obtained results are shown below.

$^1$H NMR (CDCl$_3$) δ8.10 (br, 1H), 7.64 (d, J=8.4 Hz, 2H), 7.53 (d, J=8.4 Hz, 2H), 6.46-6.26 (m, 2H), 5.89-5.71 (m, 3H), 4.98-4.88 (m, 4H), 3.75 (q, J=7.0 Hz, 2H), 1.92 (d, J=7.8 Hz, 4H), 1.20 (t, J=7.0 Hz, 3H).

$^{13}$C NMR (CDCl$_3$) δ163.9, 139.2, 134.9, 133.0, 131.1, 127.9, 119.2, 114.7, 114.4, 59.2, 21.2, 18.3.

From the NMR measurement results, it was confirmed that the obtained compound was 1-acryloylamino-4-(diallylethoxysilyl)benzene.

Example 4

4-(diallylethoxysilyl)phenol was prepared as follows.

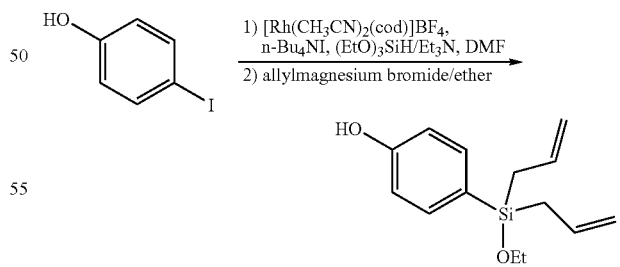

Firstly, dist. DMF (180 mL), dist. Et$_3$N (11.4 mL, 81.8 mmol) and triethoxysilane ((EtO)$_3$SiH: 15.1 mL, 81.8 mmol) were added dropwise to a mixture of 4-iodophenol (6 g, 27.3 mmol), [Rh(CH$_3$CN)$_2$ (cod)]BF$_4$ (104 mg, 0.27 mmol) and n-Bu$_4$NI (10.0 g, 27.3 mmol). The resultant mixture was stirred under a nitrogen atmosphere at 80° C. for 3 hours to obtain a reaction mixture. Subsequently, the solvent in the reaction mixture was distilled away with a vacuum pump to obtain a residue. Then, the obtained residue was extracted with ether, and a salt thus formed was removed through a celite filtration process. The solvent was distilled away from the organic layer with an evaporator to obtain a crude product (I).

Subsequently, 1-M allylmagnesium bromide (136 mL (solvent: ether), 136 mmol) was directly added dropwise to the crude product (I) at 0° C. to obtain a mixture. Then, the obtained mixture was stirred under a nitrogen atmosphere at room temperature for 19 hours. After that, the obtained mixture was cooled down with hydrochloric acid (HCl) of 10% by mass, and was added with HCl of 10% by mass until the salt barely remains. Then, the organic layer was separated from the mixture, and the aqueous layer was extracted with ether. After that, the organic layer thus collected was washed with sat. NaHCO$_3$ and a saturated aqueous solution of sodium chloride (sat. NaCl), and was dried with MgSO$_4$. The dried organic layer was then filtered and concentrated to obtain a crude product (II). Then, the obtained crude product (II) was separated and purified by silica gel column chromatography (hexane/EtOAc=5/1) to obtain 4-(diallylethoxysilyl)phenol (5.30 g, 78% yield (in two steps)).

The obtained compound was subjected to $^1$H NMR and $^{13}$C NMR measurements. The obtained results are shown below.

$^1$H NMR (CDCl$_3$) δ7.46 (d, J=8.6 Hz, 2H), 6.85 (d, J=8.6 Hz, 2H), 5.90-5.74 (m, 2H), 5.57 (br, 1H), 4.99-4.88 (m, 4H), 3.75 (q, J=6.8 Hz, 4H), 1.92 (d, J=8.4 Hz, 4H), 1.20 (t, J=6.8 Hz, 3H).

$^{13}$C NMR (CDCl$_3$) δ157.2, 135.8, 133.2, 125.9, 115.0, 114.7, 59.3, 21.2, 18.3.

From the NMR measurement results, it was confirmed that the obtained compound was 4-(diallylethoxysilyl)phenol.

Example 5

N-phenyl-N-4-(diallylethoxysilylphenyl)amine was prepared as follows.

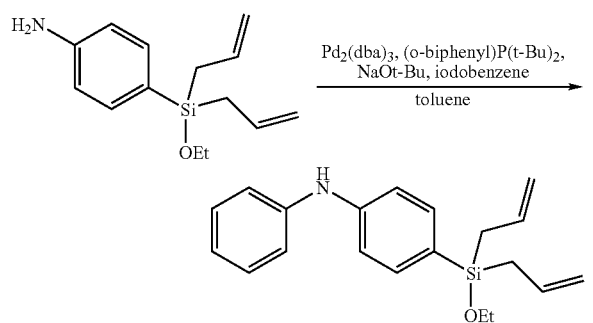

Firstly, distilled toluene (dist. toluene: 3 mL) and iodobenzene (56 μL, 0.5 mmol) were added dropwise to a mixture of 4-(diallylethoxysilyl)aniline (136 mg, 0.55 mmol), Pd$_2$(dba)$_3$ (2.5 mg, 0.0027 mmol: dba=dibenzylideneacetone), o-biphenyl-di-t-butylphosphine ((o-biphenyl)P(t-Bu)$_2$: t-Bu=tertiary butyl: 4.9 mg, 0.016 mmol) and sodium t-butoxide (NaOt-Bu: 79 mg, 0.82 mmol). The resultant mixture was stirred under a nitrogen atmosphere at room temperature for 16 hours to obtain a reaction mixture. Then, the reaction mixture was diluted with ether, and a salt thus formed was removed through a celite filtration process. After that, the solvent was distilled away from an organic layer with an evaporator to obtain a crude product. The crude product was separated and purified by silica gel column chromatography (hexane/EtOAc=3/1) to obtain N-phenyl-N-4-(diallylethoxysilylphenyl)amine (102 mg, 63% yield).

The obtained compound was subjected to $^1$H NMR and $^{13}$C NMR measurements. The obtained results are shown below.

$^1$H NMR (CDCl$_3$) δ7.45 (d, J=7.8 Hz, 2H), 7.29 (t, J=7.8 Hz, 2H), 7.12 (d, J=7.8 Hz, 2H), 7.05 (d, J=7.8 Hz, 2H), 6.97 (t, J=7.8 Hz, 1H), 5.93-5.77 (m, 3H), 4.99-4.88 (m, 4H), 3.75 (q, J=7.8 Hz, 2H), 1.92 (d, J=7.3 Hz, 4H), 1.20 (t, J=7.3 Hz, 3H).

$^{13}$C NMR (CDCl$_3$) δ144.9, 142.1, 135.4, 133.4, 129.3, 125.4, 121.7, 118.9, 115.9, 114.5, 59.1, 21.4, 18.4.

From the NMR measurement results, it was confirmed that the obtained compound was N-phenyl-N-4-(diallylethoxysilylphenyl)amine.

Example 6

N-p-tolyl-N-4-(diallylethoxysilylphenyl)amine was prepared as follows.

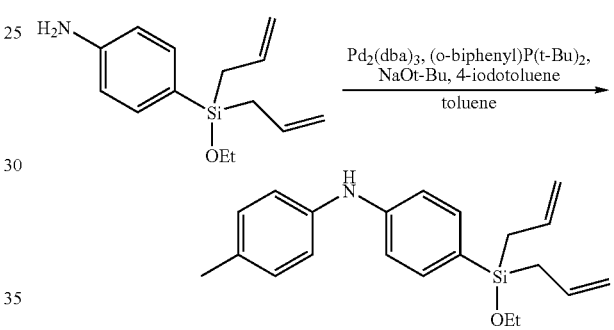

Firstly, dist. toluene (7 mL) was added to a mixture of 4-(diallylethoxysilyl)aniline (254 mg, 1.0 mmol), 4-iodotoluene (204 mg, 0.94 mmol), Pd$_2$(dba)$_3$ (4.3 mg, 0.0047 mmol), (o-biphenyl)P(t-Bu)$_2$ (8.4 mg, 0.028 mmol) and NaOt-Bu (135 mg, 1.4 mmol). The resultant mixture was stirred under a nitrogen atmosphere at room temperature for 18 hours to obtain a reaction mixture. Then, the reaction mixture was diluted with ether, and a salt thus formed was removed through a celite filtration process. The solvent was distilled away from an organic layer with an evaporator to obtain a crude product. The crude product thus obtained was separated and purified by silica gel column chromatography (hexane/EtOAc=3/1) to obtain N-p-tolyl-N-4-(diallylethoxysilylphenyl)amine (242 mg, 77% yield).

The obtained compound was subjected to $^1$H NMR and $^{13}$C NMR measurements. The obtained results are shown below.

$^1$H NMR (CDCl$_3$) δ7.43 (d, J=8.4 Hz, 2H), 7.11 (d, J=8.6 Hz, 2H), 7.04 (d, J=8.6 Hz, 2H), 6.98 (d, J=8.4 Hz, 2H), 5.92-5.75 (m, 2H), 5.70 (br, 1H), 5.00-4.88 (m, 4H), 3.75 (q, J=6.8 Hz, 2H), 2.32 (s, 3H), 1.91 (d, J=7.8 Hz, 4H), 1.20 (t, J=6.8 Hz, 3H).

$^{13}$C NMR (CDCl$_3$) δ145.7, 139.2, 135.4, 133.5, 131.7, 129.8, 124.6, 119.9, 115.1, 114.5, 59.1, 21.4, 20.7, 18.4.

From the NMR measurement results, it was confirmed that the obtained compound was N-p-tolyl-N-4-(diallylethoxysilylphenyl)amine.

Example 7

N,N'-Bis[4-(diallylethoxysilylphenyl)]benzidine was prepared as follows.

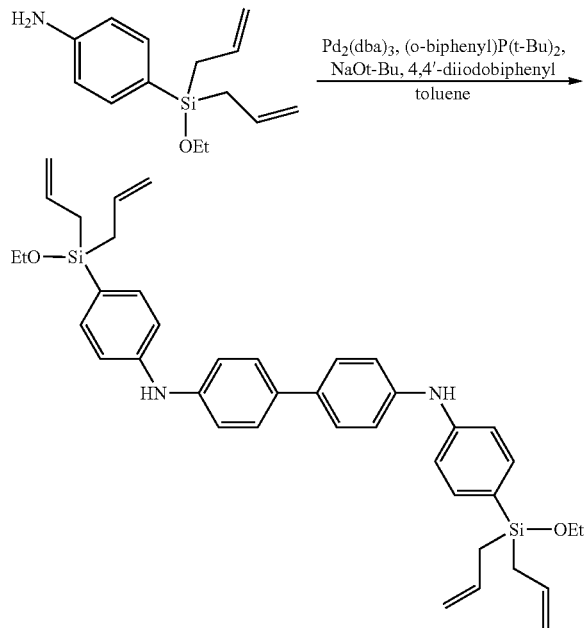

Firstly, dist. toluene (7 mL) was added to a mixture of 4-(diallylethoxysilyl)aniline (167 mg, 0.67 mmol), 4,4'-diiodobiphenyl (125 mg, 0.31 mmol), Pd$_2$(dba)$_3$ (2.8 mg, 0.0031 mmol), (o-biphenyl)P(t-Bu)$_2$ (5.5 mg, 0.018 mmol) and NaOt-Bu (89 mg, 0.93 mmol). The resultant mixture was stirred under a nitrogen atmosphere at room temperature for 18 hours to obtain a reaction mixture. Then, the reaction mixture was diluted with ether, and a salt thus formed was removed through a celite filtration process. The solvent was distilled away from an organic layer with an evaporator to obtain a crude product. Subsequently, the obtained crude product was separated and purified by PTLC (hexane/EtOAc=3/1) to obtain N,N'-bis[4-(diallylethoxysilylphenyl)]benzidine (78.1 mg, 39% yield).

The obtained compound was subjected to $^1$H NMR and $^{13}$C NMR measurements. The obtained results are shown below.

$^1$H NMR (CDCl$_3$) δ7.50 (d, J=8.6 Hz, 4H), 7.48 (d, J=8.6 Hz, 4H), 7.17 (d, J=8.6 Hz, 4H), 7.08 (d, J=8.6 Hz, 4H), 5.94-5.78 (m, 6H), 5.00-4.89 (m, 8H), 3.76 (q, J=7.0 Hz, 4H), 1.93 (d, J=8.1 Hz, 8H), 1.21 (t, J=7.0 Hz, 6H).

$^{13}$C NMR (CDCl$_3$) δ144.8, 140.9, 135.4, 134.2, 133.4, 127.3, 125.5, 119.1, 116.0, 114.6, 59.2, 21.3, 18.4.

From the NMR measurement results, it was confirmed that the obtained compound was N,N'-bis[4-(diallylethoxysilylphenyl)]benzidine.

Synthesis Example 2

Bis(4-iodophenyl)amine was prepared as follows.

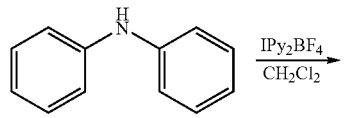

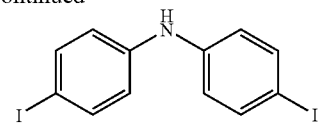

Firstly, dist. CH$_2$Cl$_2$ (10 mL) was added to a mixture of IPy$_2$BF$_4$ (231 mg, 0.62 mmol) and diphenylamine (50 mg, 0.30 mmol) under a nitrogen atmosphere. Then, the resultant mixture was stirred under a nitrogen atmosphere at room temperature for 30 minutes to obtain light-sage-green reaction mixture. Subsequently, a saturated aqueous solution of sodium thiosulfate (sat. Na$_2$S$_2$O$_3$) was added to the reaction mixture, and an aqueous layer was extracted with CH$_2$Cl$_2$. After that, an organic layer thus collected was washed with sat. NaCl, and dried with Na$_2$SO$_4$. The dried organic layer was filtered and concentrated to obtain a crude product. Then, the obtained crude product was separated and purified by silica gel column chromatography (hexane/EtOAc=5/1) to obtain bis(4-iodophenyl)amine (122.1 mg, 98% yield).

The obtained compound was subjected to $^1$H NMR and $^{13}$C NMR measurements. The obtained results are shown below.

$^1$H NMR (CDCl$_3$) δ7.54 (d, J=8.9 Hz, 4H), 6.82 (d, J=8.9 Hz, 4H), 5.66 (s, 1H).

$^{13}$C NMR (CDCl$_3$) δ142.2, 138.2, 119.9, 83.2.

From the NMR measurement results, it was confirmed that the obtained compound was bis(4-iodophenyl)amine.

Synthesis Example 3

Bis(4-triethoxysilylphenyl)amine was prepared as follows.

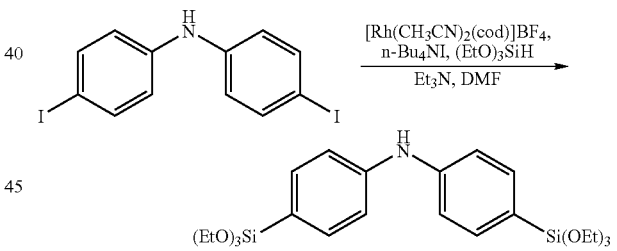

Firstly, dist. DMF (4 mL), dist. Et$_3$N (198 μL, 1.44 mmol) and (EtO)$_3$SiH (175 μL, 0.94 mmol) were added dropwise to a mixture of bis(4-iodophenyl)amine (100 mg, 0.24 mmol) obtained in Synthesis example 2, [Rh (CH$_3$CN)$_2$(cod)]BF$_4$ (4.5 mg, 0.0012 mmol) and n-Bu$_4$NI (175 mg, 0.47 mmol). Then, the resultant mixture was stirred under a nitrogen atmosphere at 80° C. for 2 hours to obtain a reaction mixture. Subsequently, the solvent in the reaction mixture was distilled away with a vacuum pump, and a residue thus obtained was extracted with ether. A salt thus formed was removed through a celite filtration process, and the solvent was distilled away with an evaporator to obtain a crude product. After that, the obtained crude product was purified with an activated carbon (7 mm in a Kiriyama funnel (small) (available from Kiriyama Glass Co., Ltd.), ether: 15 mL) to obtain almost pure bis(4-triethoxysilylphenyl)amine (102 mg, 87% yield).

The obtained compound was subjected to $^1$H NMR and $^{13}$C NMR measurements. The obtained results are shown below.

$^1$H NMR (CDCl$_3$) δ7.56 (d, J=8.6 Hz, 4H), 7.11 (d, J=8.6 Hz, 4H), 5.91 (s, 1H), 3.87 (q, J=7.0 Hz, 12H), 1.25 (t, J=7.0 Hz, 18H).

$^{13}$C NMR (CDCl$_3$) δ144.3, 136.1, 122.1, 116.9, 58.6, 18.2.

From the NMR measurement results, it was confirmed that the obtained compound was bis(4-triethoxysilylphenyl)amine.

Example 8

Bis(4-diallylethoxysilylphenyl)amine was prepared as follows.

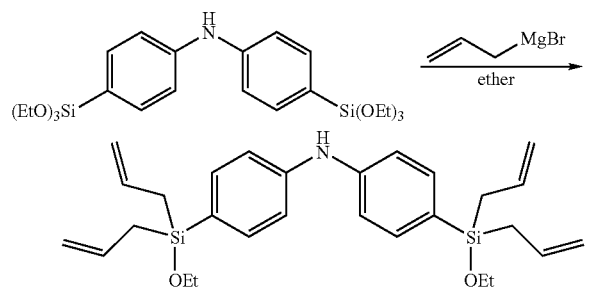

Firstly, bis(4-triethoxysilylphenyl)amine (1.76 g, 3.6 mmol) obtained in Synthesis example 3 was added with dist. ether (5 mL) under a nitrogen atmosphere, and then 1-M allylmagnasium bromide (25 mL (solvent: ether), 25 mmol) was added dropwise at 0° C. The resultant mixture was stirred under a nitrogen atmosphere at room temperature for 18 hours to obtain a mixture. Subsequently, the mixture thus obtained was added with an aqueous solution of HCl of 10% by mass to cease the reaction, and the pH of an aqueous layer was adjusted to 4 by using an aqueous solution of HCl of 10% by mass. After that, an organic layer was separated, and the aqueous layer was extracted with ether. Then, the organic layer thus collected was washed with sat. NaHCO$_3$ and sat. NaCl, and was dried with MgSO$_4$. The organic layer thus dried was filtered and concentrated to obtain a crude product. The obtained crude product was separated and purified by PTLC (hexane/EtOAc=7/1) to obtain bis(4-diallylethoxysilylphenyl)amine (1.49 g, 88% yield).

The obtained compound was subjected to $^1$H NMR and $^{13}$C NMR measurements. The obtained results are shown below.

$^1$H NMR (CDCl$_3$) δ7.48 (d, J=8.4 Hz, 4H), 7.10 (d, J=8.4 Hz, 4H), 5.93-5.77 (m, 5H), 5.00-4.89 (m, 8H), 3.76 (q, J=7.0 Hz, 4H), 1.93 (d, J=8.1 Hz, 8H), 1.21 (t, J=7.0 Hz, 6H).

$^{13}$C NMR (CDCl$_3$) δ143.8, 135.4, 133.4, 126.4, 116.9, 114.6, 59.2, 21.3, 18.4.

From the NMR measurement results, it was confirmed that the obtained compound was bis(4-diallylethoxysilylphenyl)amine.

Synthesis Example 4

Tris(4-iodophenyl)amine was prepared as follows.

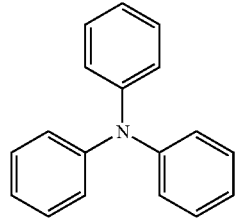

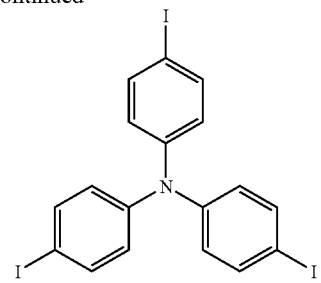

Firstly, a mixture of IPy$_2$BF$_4$ (5.3 g, 14.3 mmol) and triphenylamine (1 g, 4.1 mmol) was added with dist. CH$_2$Cl$_2$ (60 mL) under a nitrogen atmosphere, and then was added dropwise at 0° C. with trifluoromethanesulfonic acid (TfOH: 900 μL, 4.1 mmol). Thereafter, the resultant mixture was stirred under a nitrogen atmosphere at room temperature for 21 hours to obtain a reddish-brown reaction mixture. Subsequently, the obtained reaction mixture was added with sat. Na$_2$S$_2$O$_3$, and an aqueous layer wad extracted with CH$_2$Cl$_2$. After that, an organic layer thus collected was washed with sat. NaCl, and dried with Na$_2$SO$_4$. Subsequently, the dried organic layer was filtered and concentrated to obtain a crude product. Then, the obtained crude product was separated and purified by silica gel column chromatography (hexane/EtOAc=5/1) to obtain tris(4-iodophenyl) amine (2.507 g, 99% yield).

The obtained compound was subjected to $^1$H NMR and $^{13}$C NMR measurements. The obtained results are shown below.

$^1$H NMR (CDCl$_3$) δ7.54 (d, J=8.9 Hz, 6H), 6.81 (d, J=8.9 Hz, 6H).

$^{13}$C NMR (CDCl$_3$) δ146.5, 138.4, 126.0, 86.6.

From the NMR measurement results, it was confirmed that the obtained compound was tris(4-iodophenyl)amine.

Synthesis Example 5

Tris(4-triethoxysilylphenyl)amine was prepared as follows.

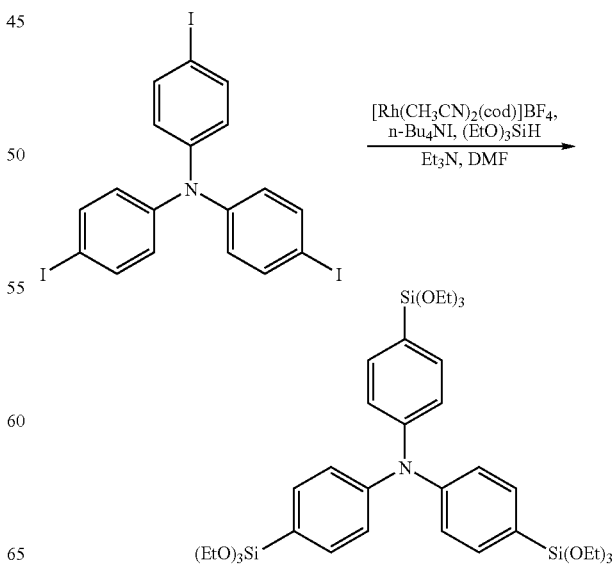

Firstly, dist. DMF (4 mL), dist. Et$_3$N (201 μL, 1.45 mmol) and (EtO)$_3$SiH (178 μL, 0.96 mmol) were added dropwise to a mixture of tris(4-iodophenyl)amine (100 mg, 0.16 mmol) obtained in Synthesis example 4, [Rh(CH$_3$CN)$_2$(cod)]BF$_4$ (5.4 mg, 0.014 mmol) and PPh$_3$MeI (195 mg, 0.48 mmol). The resultant mixture was stirred under a nitrogen atmosphere at 80° C. for 1 hour to obtain a reaction mixture. Then, the solvent in the reaction mixture was distilled away with a vacuum pump, and a residue thus obtained was extracted with ether. A salt thus formed was removed through a celite filtration process, and then the solvent was distilled away from an organic layer with an evaporator to obtain a crude product. Subsequently, the obtained crude product was purified with an activated carbon (7 mm in a Kiriyama funnel (small) (available from Kiriyama Glass Co., Ltd.), ether: 15 mL) to obtain almost pure tris(4-triethoxysilylphenyl)amine (118.4 mg, 100% yield).

The obtained compound was subjected to $^1$H NMR and $^{13}$C NMR measurements. The obtained results are shown below.

$^1$H NMR (CDCl$_3$) δ7.54 (d, J=8.6 Hz, 6H), 7.09 (d, J=8.6 Hz, 6H), 3.89 (q, J=7.0 Hz, 18H), 1.26 (t, J=7.0 Hz, 27H).

$^{13}$C NMR (CDCl$_3$) δ148.9, 135.8, 124.7, 123.5, 58.7, 18.2.

From the NMR measurement results, it was confirmed that the obtained compound was tris(4-triethoxysilylphenyl)amine.

Example 9

Tris(4-diallylethoxysilylphenyl)amine was prepared as follows.

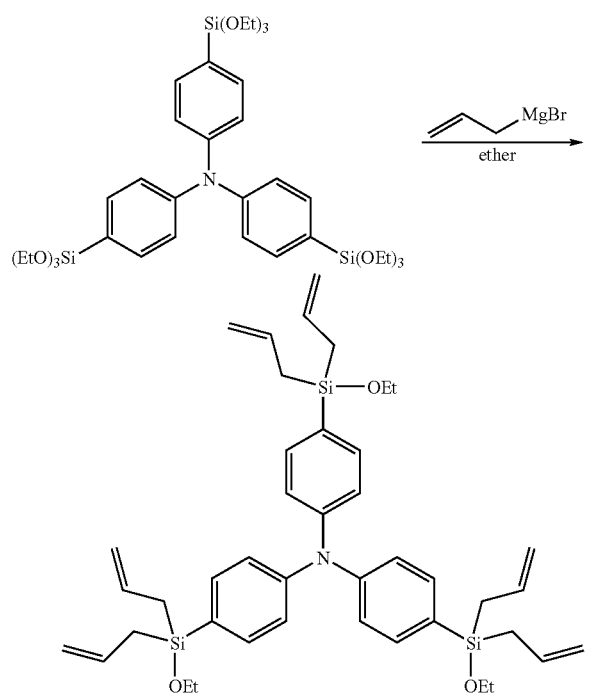

Firstly, dist. ether (5 mL) was added to tris(4-triethoxysilylphenyl)amine (242 mg, 0.33 mmol) under a nitrogen atmosphere. Then, 1-M allylmagnesium bromide (4 mL (solvent: ether), 4 mmoL) was added dropwise at 0° C. The resultant mixture was stirred under a nitrogen atmosphere at room temperature for 20 hours to obtain a mixture. Subsequently, the mixture was added with an aqueous solution of HCl of 10% by mass to cease the reaction, and the pH of an aqueous layer was adjusted to 4 by using an aqueous solution of HCl of 10% by mass. After that, an organic layer was separated, and the aqueous layer was extracted with ether. The organic layer thus collected was washed with sat. NaHCO$_3$ and sat. NaCl, and was dried with MgSO$_4$. The dried organic layer was then filtered and concentrated to obtain a crude product. Subsequently, the crude product was separated and purified by PTLC (hexane/EtOAc=10/1) to obtain tris(4-diallylethoxysilylphenyl)amine (80 mg, 34% yield).

The obtained compound was subjected to $^1$H NMR and $^{13}$C NMR measurements. The obtained results are shown below.

$^1$H NMR (CDCl$_3$) δ7.46 (d, J=8.4 Hz, 6H), 7.09 (d, J=8.4 Hz, 6H), 5.93-5.77 (m, 6H), 5.00-4.90 (m, 12H), 3.79 (q, J=7.0 Hz, 6H), 1.93 (d, J=7.8 Hz, 12H), 1.22 (t, J=7.0 Hz, 9H).

$^{13}$C NMR (CDCl$_3$) δ148.5, 135.1, 133.3, 129.0, 123.4, 114.7, 59.2, 21.3, 18.4.

From the NMR measurement results, it was confirmed that the obtained compound was tris(4-diallylethoxysilylphenyl)amine.

Synthesis Example 6

4-(triethoxysilyl)iodobenzene was prepared as follows.

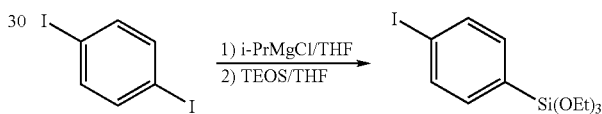

Firstly, 2-M i-PrMgCl (24 mL (solvent: THF, 48 mmol) was added dropwise to a mixture of 1,4-diiodobenzene (15 g, 45.6 mmol) and dist. THF (114 mL) at −30° C. Then the resultant mixture was stirred under a nitrogen atmosphere at −30° C. for 5.5 hours to obtain a reaction solution. Subsequently, the reaction solution was added dropwise (3 drops/second) using a cannular into a mixture of tetraethoxysilane (TEOS: 60.6 mL, 272 mmol) and dist. THF (90 mL), which was cooled to −30° C. The resultant mixture was stirred at −30° C. for 1 hour, and then was stirred at room temperature for 44 hours to obtain a reaction mixed solution. Thereafter, the obtained reaction mixed solution was added with ether (100 mL), and then was washed with distilled water (dist. H$_2$O). After that, an aqueous layer was extracted with ether. Then, an organic layer thus collected was washed with sat. NaCl, and was dried with MgSO$_4$. The dried organic layer was filtered and concentrated to obtain a crude product. Subsequently, the obtained crude product was purified by a reduced-pressure distillation process (1.5 mmHg, 120° C.) to obtain 4-(triethoxysilyl)iodobenzene (10.2 g, 61% yield).

The obtained compound was subjected to $^1$H NMR and $^{13}$C NMR measurements. The obtained results are shown below.

$^1$H NMR (CDCl$_3$) δ7.73 (dd, J=7.8 Hz, 1.4 Hz, 2H), 7.39 (d, J=7.8 Hz, 1.4 Hz, 2H), 3.88 (q, J=7.3 Hz, 6H), 1.24 (t, J=7.3 Hz, 9H).

$^{13}$C NMR (CDCl$_3$) δ137.0, 136.3, 130.4, 97.8, 58.8, 18.1.

From the NMR measurement results, it was confirmed that the obtained compound was 4-(triethoxysilyl)iodobenzene.

Synthesis Example 7

4-(diallylethoxysilyl)iodobenzene was prepared as follows.

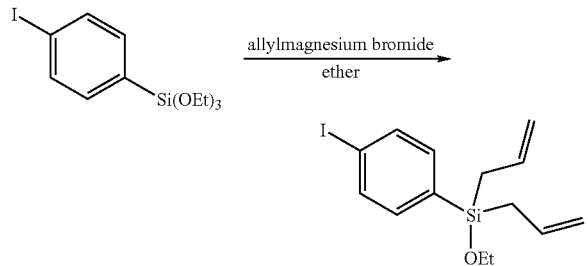

Firstly, 1-M allylmagnesium bromide (77 mL (solvent: ether), 77 mmol) was added dropwise to 4-(triethoxysilyl)iodobenzene (9.4 g, 25.7 mmol) obtained in Synthesis example 6 at 0° C. The resultant mixture was stirred under a nitrogen atmosphere at room temperature for 13 hours to obtain a mixture. Then, the mixture was added with an aqueous solution of HCl of 10% by mass to cease the reaction. The pH of an aqueous layer was adjusted to 4 by using an aqueous solution of HCl of 10% by mass. Thereafter, an organic layer was separated, and the aqueous layer was extracted with ether. The organic layer thus collected was washed with sat. NaHCO$_3$ and sat. NaCl, and was dried with MgSO$_4$. The dried organic layer was filtered and concentrated to obtain a crude product. Subsequently, the obtained crude product was separated and purified by silica gel column chromatography (hexane/EtOAc=20/1) to obtain 4-(diallylethoxysilyl)iodobenzene (9.0 g, 98%).

The obtained compound was subjected to $^1$H NMR and $^{13}$C NMR measurements. The obtained results are shown below.

$^1$H NMR (CDCl$_3$) δ7.72 (d, J=8.1 Hz, 2H), 7.29 (d, J=8.1 Hz, 2H), 5.87-5.71 (m, 2H), 4.98-4.89 (m, 4H), 3.75 (q, J=6.8 Hz, 4H), 1.91 (d, J=8.1 Hz, 4H), 1.20 (t, J=6.8 Hz, 3H).

$^{13}$C NMR (CDCl$_3$) δ136.9, 135.6, 134.5, 132.7, 115.0, 97.1, 59.4, 21.1, 18.4.

From the NMR measurement results, it was confirmed that the obtained compound was 4-(diallylethoxysilyl)iodobenzene.

Example 10

1-[(4-diallylethoxysilyl)phenyl]-4-trimethylsilylethyne was prepared as follows.

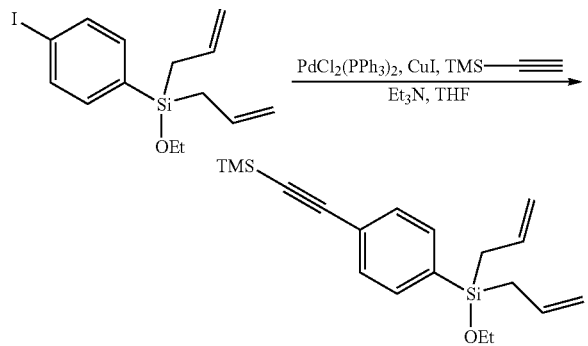

Firstly, a mixture of PdCl$_2$(PPh$_3$)$_2$ (42.7 mg, 0.06 mmol) and CuI (11.5 mg, 0.06 mmol) was added with another mixture of 4-(diallylethoxysilyl)-iodobenzene (547 mg, 1.53 mmol) and dist. THF (17 mL) as well as with dist. Et$_3$N (848 μL, 6.1 mmol) and trimethylsilylacetylene (261 μL, 1.85 mmol). The resultant mixture was stirred under a nitrogen atmosphere at 50° C. for 24 hours to obtain a reaction mixture. Then, the reaction mixture was diluted with ether. After that, an organic layer was washed with dist. H$_2$O and sat. NaCl, and was dried with MgSO$_4$. The dried organic layer was filtered and concentrated to obtain a crude product. The obtained crude product was separated and purified by silica gel column chromatography (hexane/EtOAc=20/1) to obtain 1-[(4-diallylethoxysilyl)phenyl]-4-trimethylsilylethyne (484.8 mg, 97% yield).

The obtained compound was subjected to $^1$H NMR and $^{13}$C NMR measurements. The obtained results are shown below.

$^1$H NMR (CDCl$_3$) δ7.51 (d, J=8.1 Hz, 2H), 7.45 (d, J=8.1 Hz, 2H), 5.88-5.71 (m, 2H), 4.99-4.88 (m, 4H), 3.78 (q, J=6.8 Hz, 2H), 1.92 (d, J=7.8 Hz, 4H), 1.20 (t, J=6.8 Hz, 3H), 0.249 (s, 9H).

$^{13}$C NMR (CDCl$_3$) δ135.8, 133.8, 132.8, 131.0, 124.4, 114.9, 105.0, 95.2, 59.3, 21.1, 18.4, −0.074.

From the NMR measurement results, it was confirmed that the obtained compound was 1-[(4-diallylethoxysilyl)phenyl]-4-trimethylsilylethyne.

Synthesis Example 8

4-bromo-triethoxysilylbenzene was produced as follows.

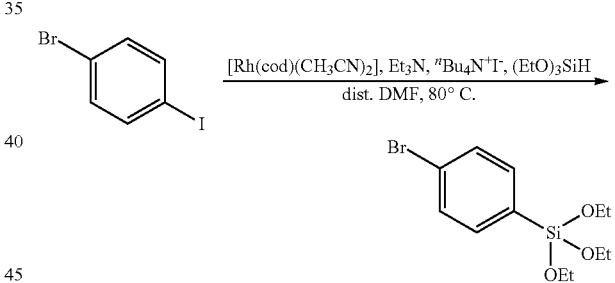

Firstly, a mixture of 4-iodo-bromobenzene (2.60 g, 9.19 mmol), t-butylammoniumiodido (3.39 g, 9.18 mmol) and [Rh(cod) (CH$_3$CN)$_2$] (105 mg, 0.277 mmol) was added with DMF (26 mL) and triethylamine (2.56 mL, 18.4 mmol). Triethoxysilane (1.87 mL, 10.1 mmol) was added dropwise to the resultant mixture at 0° C., and then the mixture thus newly produced was stirred under a nitrogen atmosphere at 80° C. for 1 hour to obtain a reaction mixture. Subsequently, the solvent in the reaction mixture was distilled away with a vacuum pump, and then the resultant mixture was subjected to a celite filtration process with ether and a concentration process under a nitrogen atmosphere to obtain a crude product. The obtained crude product was purified with a Kugelrohr distillation apparatus to obtain 4-bromo-triethoxysilylbenzene (2.38 g, 81% yield).

The obtained compound was subjected to a $^1$H NMR measurement. The obtained NMR graph is shown in FIG. 1. From the NMR measurement result, it was confirmed that the obtained compound was 4-bromo-triethoxysilylbenzene.

Synthesis Example 9

4-bromo-diallylethoxysilylbenzene was prepared as follows.

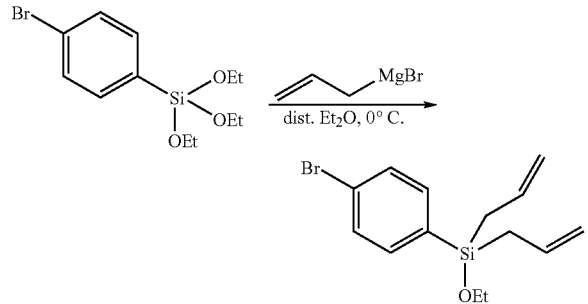

Firstly, a solution of 1-M Allyl Grignard ether (59.4 mmol, 59.4 mL) was added dropwise to 4-bromo-triethoxysilylbenzene (4.74 g, 14.8 mmol) obtained in Synthesis example 8 at 0° C. The resultant mixture was stirred under a nitrogen atmosphere at room temperature overnight to obtain a reaction mixture. Then, the reaction mixture was added with an aqueous solution of HCl of 10% by mass to cease the reaction. After that, an organic layer was extracted with ether, and the organic layer thus collected was washed with sat. NaHCO$_3$ and sat. NaCl. Subsequently, the obtained organic layer was dried with MgSO$_4$, and the dried organic layer was filtered and concentrated to obtain a crude product. The obtained crude product was purified by a Kugelrohr distillation apparatus to obtain 4-bromo-diallylethoxysilylbenzene (4.20 g, 90.7% yield).

Figure 2:
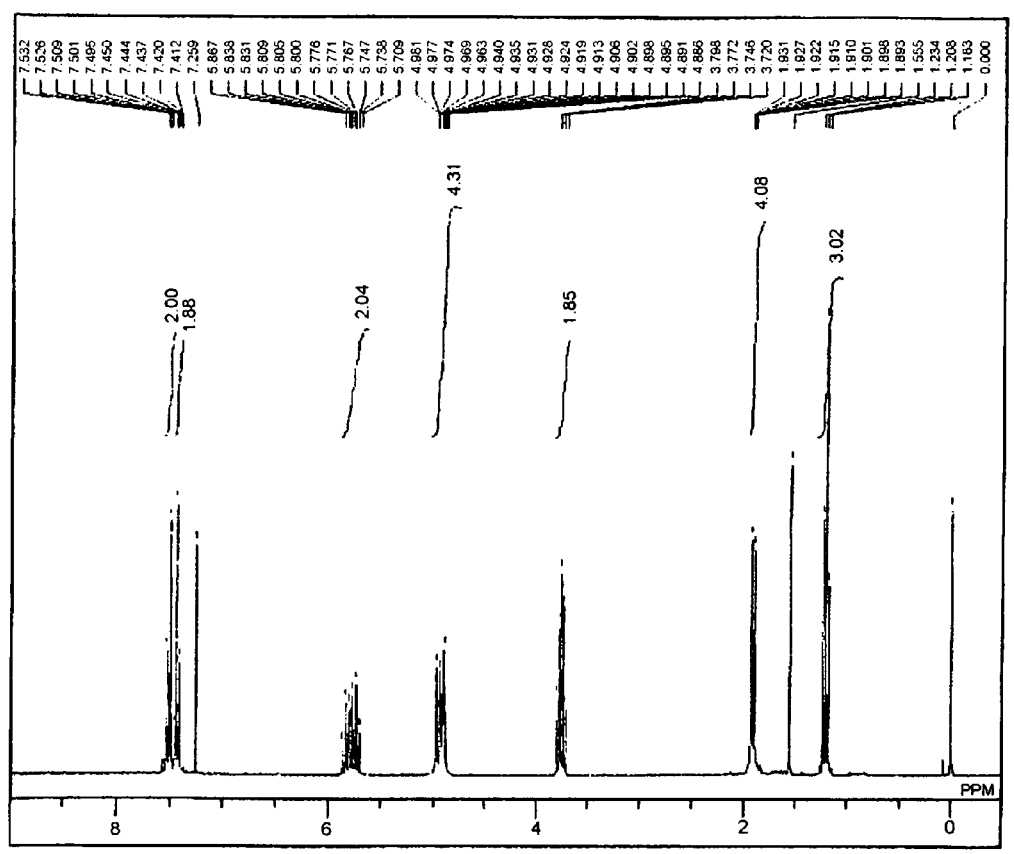
FIG. 2 is a graph showing a ¹H NMR of a compound obtained in Synthesis example 9 (4-bromo-diallylethoxysilylbenzene).
Figure 3:
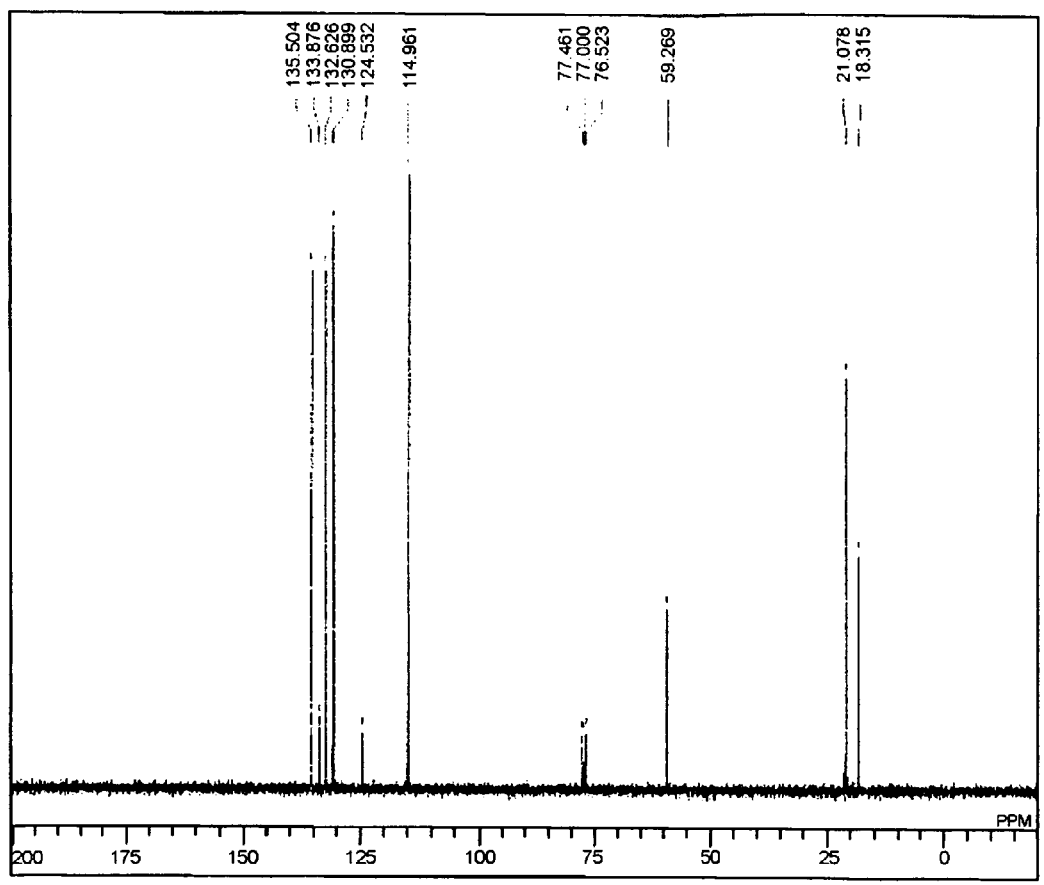
FIG. 3 is a graph showing a ¹³C NMR of the compound obtained in Synthesis example 9 (4-bromo-diallylethoxysilylbenzene).

The obtained compound was subjected to $^1$H NMR and $^{13}$C NMR measurements. The obtained NMR graphs are shown in FIGS. 2 and 3. From the NMR measurement results, it was confirmed that the obtained compound was 4-bromo-diallylethoxysilylbenzene.

Example 11

1-[(4-diallylethoxysilyl)phenyl]-4-trimethylsilylethyne was prepared as follows.

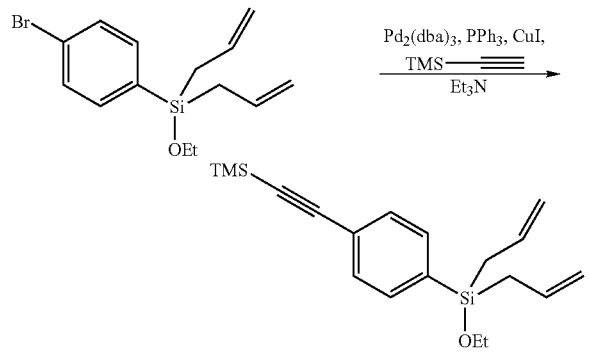

Firstly, a mixture of Pd$_2$(dba)$_3$ (22 mg, 0.04 mmol), PPh$_3$ (40 mg, 0.15 mmol) and CuI (14 mg, 0.07 mmol) was added with a mixture of 4-bromo-diallylethoxysilylbenzene (288 mg, 0.925 mmol) obtained in Synthesis example 9 and Et$_3$N (13 mL) as well as with trimethylsilylacetylene (157 μL, 1.11 mmol). The resultant mixture was stirred under a nitrogen atmosphere at 75° C. for 21 hours to obtain a reaction mixture. Then, the solvent in the reaction mixture was distilled away with a vacuum pump, and an organic layer was diluted with ether. After that, the organic layer thus collected was washed with sat. NaCl. Subsequently, the obtained organic layer was dried with MgSO$_4$, and the dried organic layer was filtered and concentrated to obtain a crude product. The obtained crude product was separated and purified by silica gel column chromatography (hexane/EtOAc=5/1) to obtain 1-[(4-diallylethoxysilyl)phenyl]-4-trimethylsilylethyne (220.1 mg, 72% yield).

The obtained compound was subjected to $^1$H NMR and $^{13}$C NMR measurements. The results obtained here were similar to those obtained by the NMR measurements carried out in Example 10. From the obtained results, it was confirmed that the obtained compound was 1-[(4-diallylethoxysilyl)phenyl]-4-trimethylsilylethyne.

Example 12

4-(diallylethoxysilyl)benzaldehyde was prepared as follows.

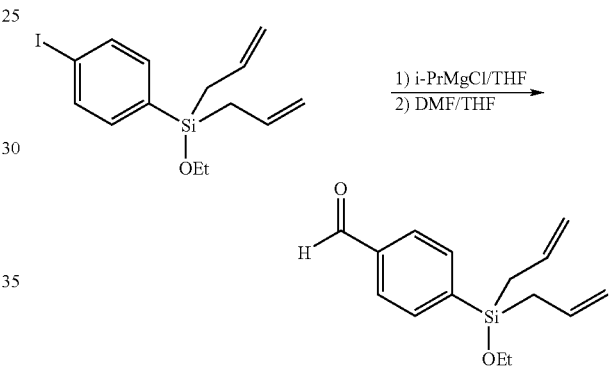

Firstly, i-PrMgCl (0.71 mL, 2 M in THF, 1.42 mmol) was added dropwise to a THF solution (2 mL) of 4-(diallylethoxysilyl)iodobenzene (255 mg, 0.71 mmol) obtained in Synthesis example 7 at −30° C. The resultant mixture was stirred under a nitrogen atmosphere at −30° C. for 1.5 hours to obtain a solution containing 4-(diallylethoxysilyl)phenylmagnesium chloride (Grignard solution). Then, DMF (110 μL, 1.42 mmol) was added dropwise to the obtained solution at −30° C., and the resultant mixture was stirred under a nitrogen atmosphere at room temperature for 13 hours to obtain a reaction mixture. Subsequently, an aqueous solution of HCl of 10% by mass was added to the reaction mixture to cease the reaction. After that, an organic layer was separated from the reaction mixture, and an aqueous layer was extracted with ether. The organic layer thus collected was washed with sat. NaHCO$_3$ and sat. NaCl, and dried with MgSO$_4$. The dried organic layer was filtered and concentrated to obtain a crude product. The crude product was separated and purified by silica gel column chromatography (hexane/EtOAc=20/1) to obtain 4-(diallylethoxysilyl)benzaldehyde (158 mg, 85% yield).

The obtained compound was subjected to $^1$H NMR and $^{13}$C NMR measurements. The obtained results are shown below.

$^1$H NMR (CDCl$_3$) δ10.0 (s, 1H), 7.87 (d, J=8.4 Hz, 2H), 7.75 (d, J=8.4 Hz, 2H), 5.88-5.72 (m, 2H), 4.99-4.91 (m, 4H), 3.81 (q, J=6.8 Hz, 2H), 1.96 (d, J=8.1 Hz, 4H), 1.24 (t, J=6.8 Hz, 3H).

<sup>13</sup>C NMR (CDCl<sub>3</sub>) δ192.5, 143.5, 137.0, 134.5, 132.4, 128.6, 115.2, 59.5, 21.1, 18.3.

From the NMR measurement results, it was confirmed that the obtained compound was 4-(diallylethoxysilyl)benzaldehyde.

Synthesis Example 10

1-(diallylethoxysilyl)-4-(3,5-dimethyl-3-hydroxy-hexynyl)benzene was prepared as follows.

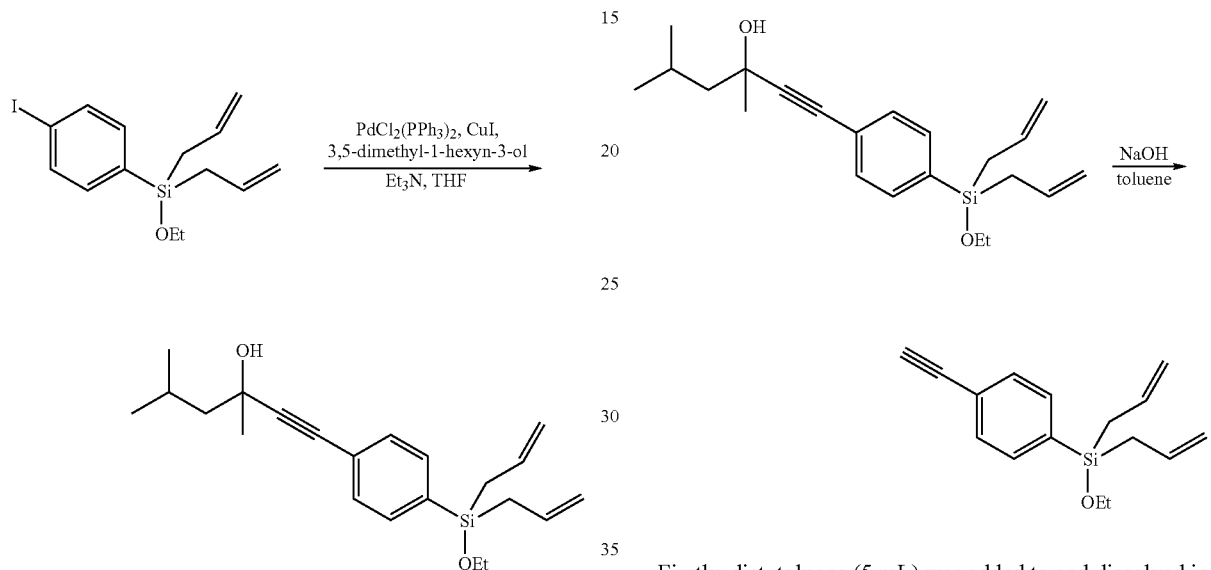

Firstly, a mixture of 4-(diallylethoxysilyl)iodobenzene (147 mg, 0.41 mmol), PdCl<sub>2</sub>(PPh<sub>3</sub>)<sub>2</sub> (11.5 mg, 0.016 mmol) and CuI (3.1 mg, 0.016 mmol) was added with dist. THF (2 mL), dist. Et<sub>3</sub>N (3 mL) and 3,5-dimethyl-1-hexyn-3-ol (79 μL, 0.54 mmol). The resultant mixture was stirred under a nitrogen atmosphere at 50° C. for 3 hours to obtain a reaction mixture. Then, the reaction mixture was diluted with ether, and an organic layer was washed with dist. H<sub>2</sub>O and sat. NaCl. After that, the organic layer was dried with MgSO<sub>4</sub>, and the dried organic layer was then filtered and concentrated to obtain a crude product. The obtained crude product was separated and purified by silica gel column chromatography (hexane/EtOAc=5/1) to obtain 1-(diallylethoxysilyl)-4-(3,5-dimethyl-3-hydroxy-hexynyl)benzene (129.1 mg, 88% yield).

The obtained compound was subjected to <sup>1</sup>H NMR and <sup>13</sup>C NMR measurements. The obtained results are shown below.

<sup>1</sup>H NMR (CDCl<sub>3</sub>) δ7.51 (d, J=8. Hz, 2H), 7.41 (d, J=8.1 Hz, 2H), 5.87-5.72 (m, 2H), 4.98-4.88 (m, 4H), 3.76 (q, J=7.0 Hz, 2H), 2.07-1.97 (m, 1H), 1.99 (s, 1H), 1.92 (d, J=7.0 Hz, 4H), 1.69 (d, J=5.9 Hz, 2H), 1.59 (s, 3H), 1.21 (t, J=7.0 Hz, 3H), 1.06 (dd, J=3.0 Hz, 7.0 Hz, 6H).

<sup>13</sup>C NMR (CDCl<sub>3</sub>) δ135.4, 133.8, 132.8, 130.7, 124.2, 114.9, 94.3, 83.4, 68.4, 59.3, 51.9, 30.9, 25.2, 24.2, 24.1, 21.1, 18.3.

From the NMR measurement results, it was confirmed that the obtained compound was 1-(diallylethoxysilyl)-4-(3,5-dimethyl-3-hydroxy-hexynyl)benzene.

Example 13

1-(diallylethoxysilyl)-4-ethynylbenzene was prepared as follows.

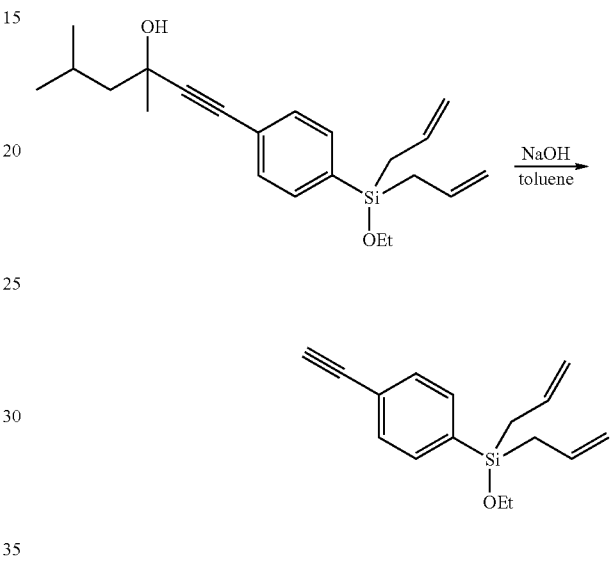

Firstly, dist. toluene (5 mL) was added to and dissolved in 1-(diallylethoxysilyl)-4-(3,5-dimethyl-3-hydroxy-hexynyl)benzene (125 mg, 0.35 mmol) obtained in Synthesis example 10. The resultant mixture was added with NaOH (9.9 mg, 0.25 mmol), and then was stirred under a nitrogen atmosphere at 80° C. for 16 hours to obtain a reaction mixture. Then, the reaction mixture was diluted with CH<sub>2</sub>Cl<sub>2</sub>, and an organic layer was washed with dist. H<sub>2</sub>O and sat. NaCl. The organic layer thus collected was dried with MgSO<sub>4</sub>, and the dried organic layer was filtered and concentrated to obtain a crude product. The obtained crude product was separated and purified by silica gel column chromatography (hexane/EtOAc=5/1) to obtain 1-(diallylethoxysilyl)-4-ethynylbenzene (5 mg, 6% yield).

The obtained compound was subjected to <sup>1</sup>H NMR and <sup>13</sup>C NMR measurements. The obtained results are shown below.

<sup>1</sup>H NMR (CDCl<sub>3</sub>) δ7.54 (d, J=8.4 Hz, 2H), 7.49 (d, J=8.4 Hz, 2H), 5.88-5.72 (m, 2H), 4.99-4.90 (m, 4H), 3.77 (q, J=7.0 Hz, 2H), 3.12 (s, 1H), 1.93 (d, J=7.8 Hz, 4H) 1.21 (t, J=7.0 Hz, 3H).

<sup>13</sup>C NMR (CDCl<sub>3</sub>) δ136.2, 133.9, 132.8, 131.2, 123.4, 115.0, 83.6, 78.0, 59.4, 21.1, 18.4.

From the NMR measurement results, it was confirmed that the obtained compound was 1-(diallylethoxysilyl)-4-ethynylbenzene.

Example 14

N,N-bis(4-(diallylethoxysilyl)phenyl)-4-methoxyaniline was prepared as follows.

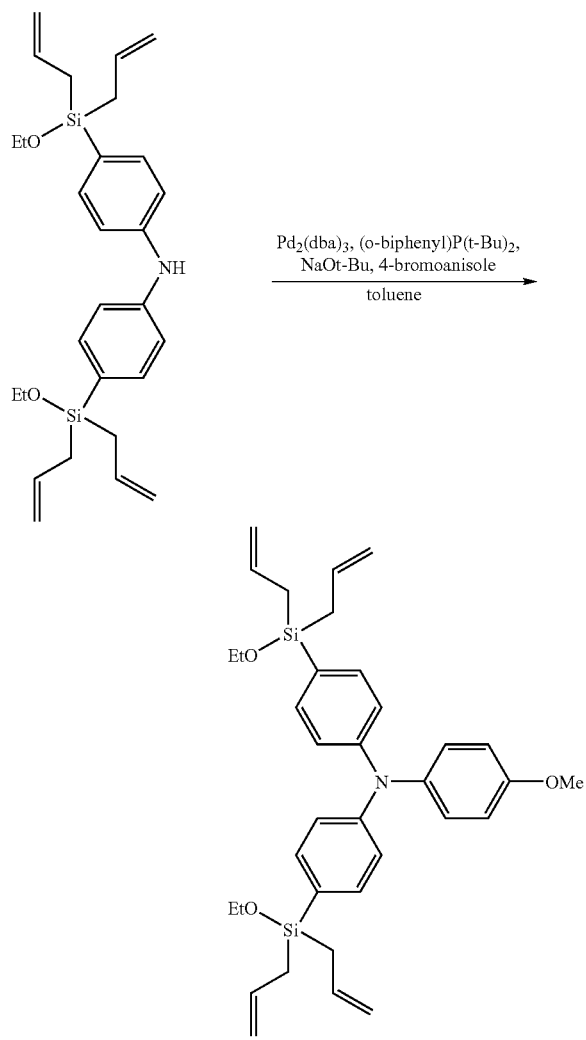

Firstly, dist. toluene (5 mL) and 4-bromoanisole (58 μL, 0.46 mmol) were added dropwise to a mixture of bis[4-(diallylethoxysilyl)phenyl]amine (111 mg, 0.23 mmol), Pd$_2$(dba)$_3$ (1 mg, 0.0011 mmol), (o-biphenyl)P(t-Bu) 2 (2 mg, 0.03 mmol) and NaOt-Bu (33 mg, 0.35 mmol). The resultant mixture was stirred under a nitrogen atmosphere at 80° C. for 24 hours to obtain a reaction mixture. Then, the reaction mixture was diluted with ether. A salt thus formed was removed through a celite filtration process, and the solvent was distilled away from an organic layer with an evaporator to obtain a crude product. The obtained crude product was separated and purified by PTLC (hexane/EtOAc/acetone=20/2/1) to obtain N,N-bis(4-(diallylethoxysilyl)phenyl)-4-methoxyaniline (65.8 mg, 48% yield).

The obtained compound was subjected to $^1$H NMR and $^{13}$C NMR measurements. The obtained results are shown below.

$^1$H NMR (CDCl$_3$) δ7.41 (d, J=7.8 Hz, 4H), 7.10 (d, J=8.4 Hz, 2H), 7.03 (d, J=7.8 Hz, 4H), 6.87 (d, J=8.4 Hz, 2H), 5.93-5.77 (m, 4H), 5.00-4.89 (m, 8H), 3.81 (s, 3H), 3.77 (q, J=6.8 Hz, 4H), 1.92 (d, J=7.8 Hz, 8H), 1.21 (t, J=6.8 Hz, 6H).

$^{13}$C NMR (CDCl$_3$) δ156.8, 149.0, 139.7, 134.9, 133.4, 128.3, 127.3, 121.6, 114.8, 114.6, 59.2, 55.4, 21.3, 18.4.

From the NMR measurement results, it was confirmed that the obtained compound was N,N-bis(4-(diallylethoxysilyl)phenyl)-4-methoxyaniline.

Synthesis example 11

4-(triethoxysilyl)styrene was produced as follows.

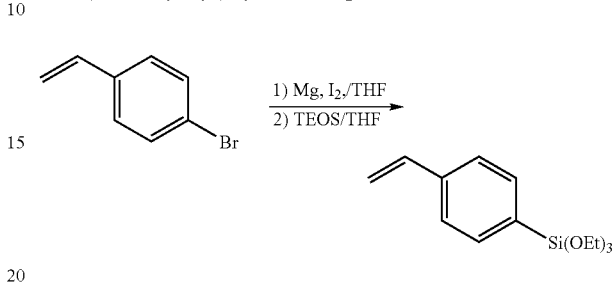

Firstly, dist. THF (1 mL) was added to Mg (2 g, 11 mmol) that has been activated under vacuum, and subsequently a small amount of I$_2$ was added to the resultant mixture to obtain a mixed solution. Then, the activation of the Mg in the mixed solution was checked. Once such activation was confirmed, the mixed solution was added with dist. THF (16 mL). After that, at room temperature, a solution containing 4-bromostyrene (2 g, 11 mmol) and dist. THF (5 mL) was added dropwise to obtain a reaction solution. Then, the obtained reaction solution was stirred under a nitrogen atmosphere and a reflux condition (at 80° C.) for 20 hours to obtain 4-styrenemagnesium bromide. After that, TEOS (2.2 mL, 8.8 mmol)/dist. THF (10 mL) was added dropwise to the obtained 4-styrenemagnesium bromide under a nitrogen atmosphere at room temperature (25° C.) to obtain a reaction mixture. Subsequently, the obtained reaction mixture was stirred under a nitrogen atmosphere and a reflux condition (80° C.) for 15 hours, and then was left standing to cool to room temperature. The cooled reaction mixture was added with distilled hexane (dist. hexane: 50 mL) to make the excess Mg salt be precipitated. The salt thus formed was removed through a celite filtration process, and an organic layer was concentrated under reduced pressure to obtain a residue. Then, the obtained residue was purified through a reduced-pressure distillation process (0.01 mmHg, 80° C.) to obtain 4-(triethoxysilyl)styrene (176 mg, 6% yield).

Example 15

4-(diallylethoxysilyl)styrene was prepared as follows.

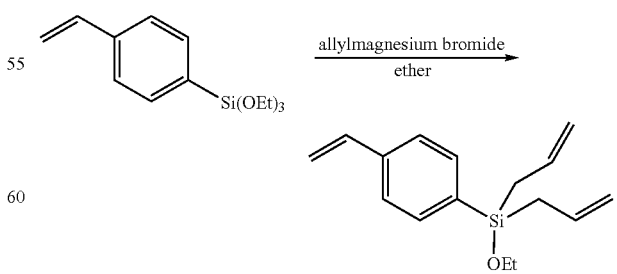

Firstly, 1-M allylmagnesium bromide (3.3 mL (solvent: ether), 3.3 mmol) was added dropwise, at 0° C., to 4-(triethoxysilyl)styrene (176 mg, 0.66 mmol) obtained in Synthesis example 11. The resultant mixture was stirred under a nitrogen atmosphere at room temperature for 13 hours to obtain a reaction mixture. Then, an aqueous solution of HCl of 10% by mass was added to cease the reaction, and thereafter the pH of an aqueous layer was adjusted to 4 with an aqueous solution of HCl of 10% by mass. After that, an organic layer was thus separated, and the aqueous layer was extracted with ether. The organic layer thus collected was washed with sat. NaHCO$_3$ and sat. NaCl, and was dried with MgSO$_4$. The dried-organic layer was then filtered and concentrated to obtain a crude product. The obtained crude product was separated and purified by silica gel column chromatography (hexane/EtOAc=20/1) to obtain 4-(diallylethoxysilyl)styrene (92.6 mg, 53% yield).

The obtained compound was subjected to $^1$H NMR and $^{13}$C NMR measurements. The obtained results are shown below.

$^1$H NMR (CDCl$_3$) δ7.54 (d, J=8.1 Hz, 2H), 7.41 (d, J=8.1 Hz, 2H), 6.74-6.66 (m, 1H), 5.90-5.74 (m, 3H), 5.27 (dd, J=0.8 Hz, 10.8 Hz, 1H), 4.99-4.88 (m, 4H), 3.76 (q, J=7.0 Hz, 2H), 1.93 (d, J=7.8 Hz, 4H), 1.20 (t, J=7.0 Hz, 3H).

$^{13}$C NMR (CDCl$_3$) δ138.8, 136.7, 134.6, 134.3, 133.1, 125.5, 114.7, 114.6, 59.3, 21.2, 18.4.

From the NMR measurement results, it was confirmed that the obtained compound was 4-(diallylethoxysilyl)styrene.

Synthesis Example 12

3,6-bis(trimethylsilylethynyl)-9-methylcarbazole was prepared as follows.

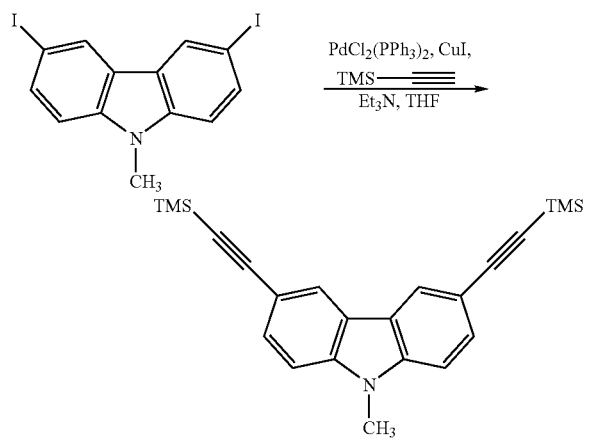

Firstly, a mixture of PdCl$_2$(PPh$_3$)$_2$ (13 mg, 0.018 mmol), CuI (3.5 mg, 0.018 mmol) and 3,6-diiodo-9-methylcarbazole (200 mg, 0.46 mmol) was added with dist. THF (3 mL), dist. Et$_3$N (1.5 mL) and trimethylsilylacetylene (653 μL, 4.6 mmol). The resultant mixture was stirred under a nitrogen atmosphere at room temperature for 3 hours to obtain a reaction mixture. Then, the reaction mixture was diluted with ether. After that, an organic layer was washed with dist. H$_2$O and sat. NaCl, and was dried with MgSO$_4$. The dried organic layer was filtered and concentrated to obtain a crude product. Subsequently, the obtained crude product was separated and purified by silica gel column chromatography (hexane/EtOAc=5/1) to obtain 3,6-bis[(trimethylsilylethynyl)-9-methylcarbazole (173 mg, 100% yield).

The obtained compound was subjected to $^1$H NMR and $^{13}$C NMR measurements. The obtained results are shown below.

$^1$H NMR (CDCl$_3$) δ8.19 (d, J=1.6 Hz, 2H), 7.59 (dd, J=1.6 Hz, 8.4 Hz, 2H), 7.30 (d, J=8.4 Hz, 2H), 3.82 (s, 3H), 0.29 (s, 18H).

$^{13}$C NMR (CDCl$_3$) δ140.9, 130.0, 124.5, 122.1, 113.8, 108.5, 106.4, 92.0, 29.2, 0.16.

From the NMR measurement results, it was confirmed that the obtained compound was 3,6-bis[(trimethylsilylethynyl)-9-methylcarbazole.

Synthesis Example 13

3,6-diethynyl-9-methylcarbazole was prepared as follows.

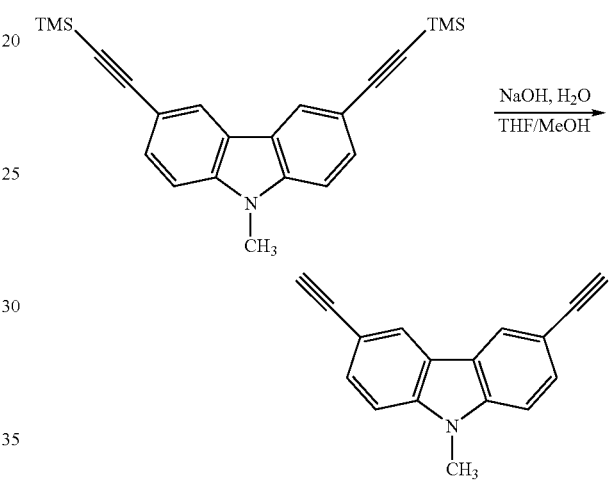

A mixed solution containing dist. THF and dist. MeOH (dist. THF/dist. MeOH=3/1: 4 mL) as well as dist. H$_2$O (0.1 mL) were added to and dissolved into 3,6-bis(trimethylsilylethynyl)-9-methylcarbazole (173 mg, 0.46 mmol) obtained in Synthesis example 12. Then, NaOH (35 mg, 0.88 mmol) was added, and the resultant mixed solution was stirred under a nitrogen atmosphere at room temperature for 4 hours to obtain a reaction mixture. After that, the reaction mixture was diluted with CH$_2$Cl$_2$. Then, an organic layer was washed with dist. H$_2$O and sat. NaCl, and was dried with MgSO$_4$. The dried organic layer was filtered and concentrated to obtain a crude product. Subsequently, the obtained crude product was separated and purified by silica gel column chromatography (hexane/EtOAc=5/1) to obtain 3,6-diethynyl-9-methylcarbazole (86 mg, 81% yield).

The obtained compound was subjected to $^1$H NMR and $^{13}$C NMR measurements. The obtained results are shown below.

$^1$H NMR (CDCl$_3$) δ8.12 (d, J=1.6 Hz, 2H), 7.56 (dd, J=1.6 Hz, 8.9 Hz, 2H), 7.22 (d, J=8.9 Hz, 2H), 3.71 (s, 3H), 3.08 (s, 2H).

$^{13}$C NMR (CDCl$_3$) δ141.0, 130.1, 124.6, 122.0, 112.6, 108.6, 84.7, 75.5, 29.1.

From the NMR measurement results, it was confirmed that the obtained compound was 3,6-diethynyl-9-methylcarbazole.

Example 16

3,6-bis[(4-diallylethoxysilyl)phenylethynyl]-9-methyl-carbazole was prepared as follows.

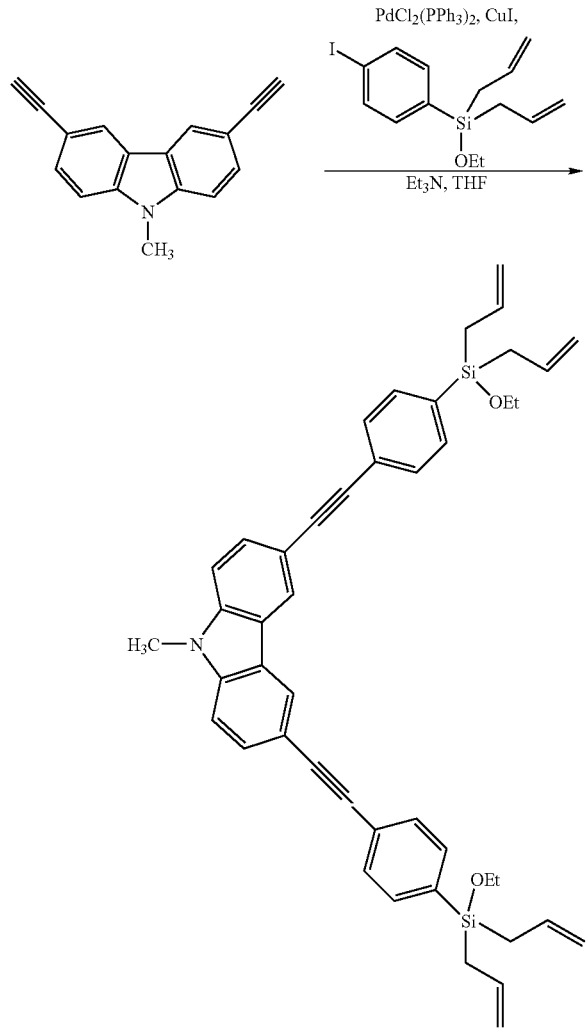

Firstly, a mixture of 3,6-diethynyl-9-methylcarbazole (70 mg, 0.31 mmol) obtained in Synthesis example 13, PdCl$_2$(PPh$_3$)$_2$ (8.6 mg, 0.012 mmol), CuI (2.3 mg, 0.012 mmol) and 4-(diallylethoxysilyl)iodobenzene (219 mg, 0.61 mmol) was added with dist. THF (3 mL) and dist. Et$_3$N (679 μL, 4.9 mmol). The resultant mixture was stirred under a nitrogen atmosphere at 50° C. for 5 hours to obtain a reaction mixture Then, the reaction mixture was diluted with ether. After that, an organic layer was washed with dist. H$_2$O and sat. NaCl, and was dried with MgSO$_4$. Then, the dried organic layer was filtered and concentrated to obtain a crude product. The obtained crude product was separated and purified by silica gel column chromatography (hexane/EtOAc=5/1) to obtain 3,6-bis[(4-diallylethoxysilyl)phenylethynyl]-9-methylcarbazole (162 mg, 77% yield).

The obtained compound was subjected to $^1$H NMR and $^{13}$C NMR measurements. The obtained results are shown below.

$^1$H NMR (CDCl$_3$) δ8.28 (d, J=1.6 Hz, 2H), 7.67 (dd, J=1.6 Hz, 8.6 Hz, 2H), 7.58 (s, 8H), 7.36 (d, J=8.6 Hz), 5.91-5.75 (m, 4H), 5.00-4.91 (m, 8H), 3.85 (s, 3H), 3.79 (q, J=6.8 Hz, 4H), 1.96 (d, J=8.4 Hz, 8H), 1.23 (t, J=6.8 Hz, 6H).

$^{13}$C NMR (CDCl$_3$) δ140.9, 134.9, 133.9, 132.9, 130.6, 129.8, 125.1, 124.1, 122.3, 114.9, 113.8, 108.7, 91.6, 87.9, 59.3, 29.2, 21.1, 18.4.

From the NMR measurement results, it was confirmed that the obtained compound was 3,6-bis[(4-diallylethoxysilyl)phenylethynyl]-9-methylcarbazole.

Synthesis Example 14

1,4-diethynylbenzene was prepared as follows.

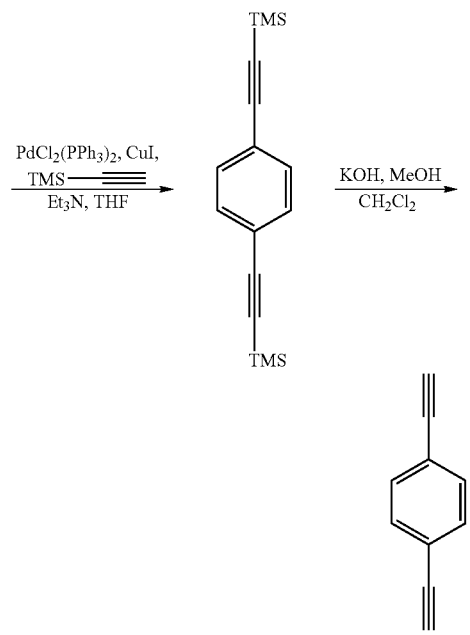

Firstly, a mixture of 1,4-diiodobenzene (4 g, 12.1 mmol), PdCl$_2$(PPh$_3$)$_2$ (340 mg, 0.484 mmol) and CuI (92.4 mg, 0.484 mmol), was added with dist. THF (20 mL), dist. Et$_3$N (60 mL) and trimethylsilylacetylene (3.77 mL, 26.7 mmol). The resultant mixture was stirred under a nitrogen atmosphere at 80° C. for 22 hours to obtain a reaction mixture. Then, the reaction mixture was diluted with CH$_2$Cl$_2$. After that, an organic layer was washed with sat. NaCl, and dried with MgSO$_4$. The dried organic layer was filtered and concentrated to obtain a crude product. The obtained crude product was separated and purified by silica gel column chromatography (hexane/EtOAc=10/1) to obtain 1,4-diethynylbenzene.

Subsequently, the obtained 1,4-bis(trimethylsilylethynyl)benzene (500 mg, 1.85 mmol) was added with dist. CH$_2$Cl$_2$ (15 mL), dist. MeOH (3 mL) and an aqueous solution of potassium hydroxide (KOH) (0.4 mL) of 50% by mass. The resultant mixture was stirred under a nitrogen atmosphere at room temperature for 18 hours to obtain a reaction mixture. Then, the reaction mixture was diluted with CH$_2$Cl$_2$. After that, an organic layer was washed with sat. NaCl, and dried with MgSO$_4$. The dried organic layer was filtered and concentrated to obtain a crude product. Subsequently, the obtained crude product was separated and purified by silica gel column chromatography (hexane/EtOAc=20/1) to obtain 1,4-diethynylbenzene (147 mg, 63% yield (in two steps)).

The obtained compound was subjected to a $^1$H NMR measurement. The obtained result is shown below.

$^1$H NMR (CDCl$_3$) δ7.44 (s, 4H), 3.17 (s, 2H)

From the NMR measurement result, it was confirmed that the obtained compound was 1,4-diethynylbenzene.

Example 17

1,4-bis[4-(diallylethoxysilyl)phenyethynyl]benzene was prepared as follows.

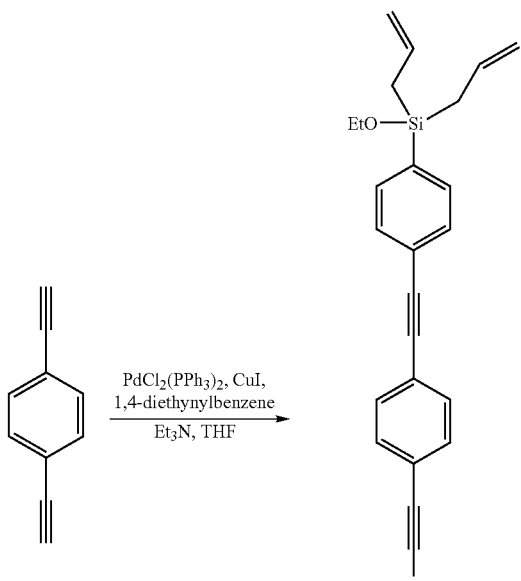

Firstly, a mixture of 1,4-diethynylbenzene (58.5 mg, 0.46 mmol) obtained in Synthesis example 14, 4-(diallylethoxysilyl)iodobenzene (277 mg, 0.77 mmol), PdCl$_2$(PPh$_3$)$_2$ (10.9 mg, 0.0155 mmol) and CuI (2.94 mg, 0.0155 mmol) was added with dist. THF (5 mL) and dist. Et$_3$N (1 mL). The resultant mixture was stirred under a nitrogen atmosphere at 50° C. for 13 hours to obtain a reaction mixture. Then, the reaction mixture was diluted with ether. After that, an organic layer was washed with dist. H$_2$O and sat. NaCl, and was dried with MgSO$_4$. The dried organic layer was filtered and concentrated to obtain a crude product. Then, the obtained crude product was separated and purified by silica gel column chromatography (hexane/EtOAc=10/1) to obtain 1,4-bis[4-(diallylethoxysilyl)phenylethynyl]benzene (215.3 mg, 95% yield).

The obtained compound was subjected to $^1$H NMR and $^{13}$C NMR measurements. The obtained results are shown below.

$^1$H NMR (CDCl$_3$) δ7.57 (d, J=8.1 Hz, 4H), 7.54 (d, J=8.1 Hz, 4H), 7.49 (s, 4H), 5.89-5.73 (m, 4H), 4.99-4.90 (m, 8H), 3.77 (q, J=7.0 Hz, 4H), 1.94 (d, J=8.1 Hz, 8H), 1.22 (t, J=7.0 Hz, 6H).

$^{13}$C NMR (CDCl$_3$) δ135.8, 133.9, 132.8, 131.5, 130.7, 124.3, 123.0, 114.9, 91.3, 90.0, 59.3, 21.1, 18.4.

From the NMR measurement results, it was confirmed that the obtained compound was 1,4-bis[4-(diallylethoxysilyl)phenylethynyl]benzene.

Example 18

9,10-Bis(4-diallylethoxysilylphenylethynyl)anthracene was prepared as follows.

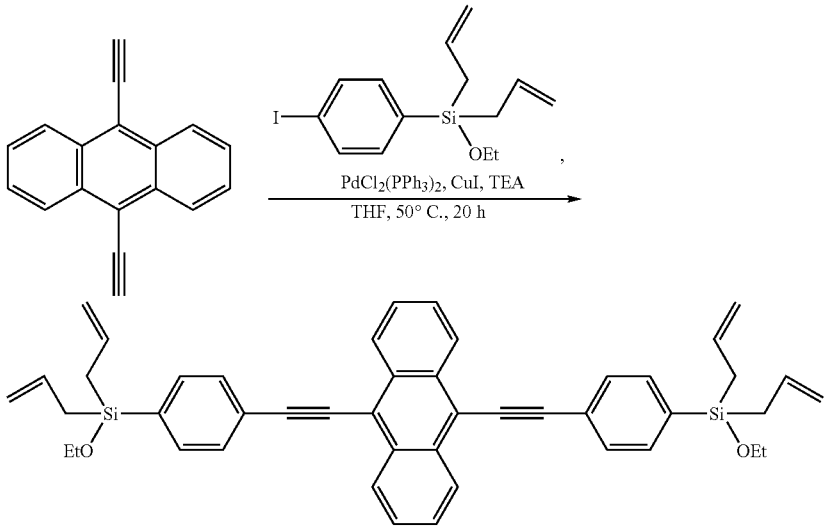

-continued

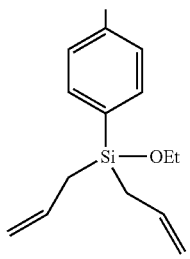

Firstly, 4-(diallylethoxysilyl)iodobenzene (500.0 mg, 1.396 mmol) obtained in Synthesis example 7, PdCl$_2$(PPh$_3$)$_2$ (35.6 mg, 0.05074 mmol) and CuI (9.7 mg, 0.05074 mmol) were put in a three-necked flask. Dehydrated THF (27.6 mL) and triethylamine (707 μL, 5.074 mmol) were added to the mixture in the three-necked flask, and the resultant mixture was stirred at room temperature for 30 minutes to obtain a mixture. Then, the mixture was added dropwise, at 0° C., with a dehydrated THF solution (3.0 mL) of 9,10-diethynylbenzene (143.5 mg, 0.6343 mmol), and then the newly produced mixture was stirred at 50° C. for 20 hours to obtain a reaction solution. The reaction was traced by TLC analysis. Once the reaction was completed, the reaction solution was concentrated under reduced pressure. A residue thus obtained was dissolved in diethyl ether (30.0 mL), and then water (30.0 mL) was added. After that, the pH of an aqueous layer was adjusted to 4 to 5 with an aqueous solution of HCl of 10% by mass, and the aqueous layer was then extracted with diethyl ether to collect an organic layer. The organic layer thus collected was washed with an aqueous solution of ammonium chloride and a saturated saline solution, three times for each solution. Then, the washed organic layer was dried with sodium sulfate. The dried organic layer was then concentrated under reduced pressure to obtain a crude product. The obtained crude product was then purified by PTLC (hexane/EtOAc=10/1 as eluent) to obtain pure 9,10-bis(4-diallylethoxysilylphenylethynyl)anthracene (a yellow-orange oily substance: 244 mg, 56% yield).

The obtained compound was subjected to a $^1$H NMR measurement. The obtained result is shown below.

$^1$H NMR (270 MHz, CDCl$_3$) δ 1.25 (t, J=7.0 Hz, 6H), 1.99 (d, J=8.1 Hz, 8H), 3.82 (q, J=7.0 Hz, 4H), 4.94-5.03 (m, 8H), 5.78-5.94 (m, 4H), 7.64-7.69 (m, 8H), 7.79 (d, 8.1 Hz, 4H), 8.68-8.72 (m, 4H)

From the NMR measurement result, it was confirmed that the obtained compound was 9,10-bis(4-diallylethoxysilylphenylethynyl)anthracene.

Synthesis Example 15

4,4'-diethynyltolan was prepared as follows.

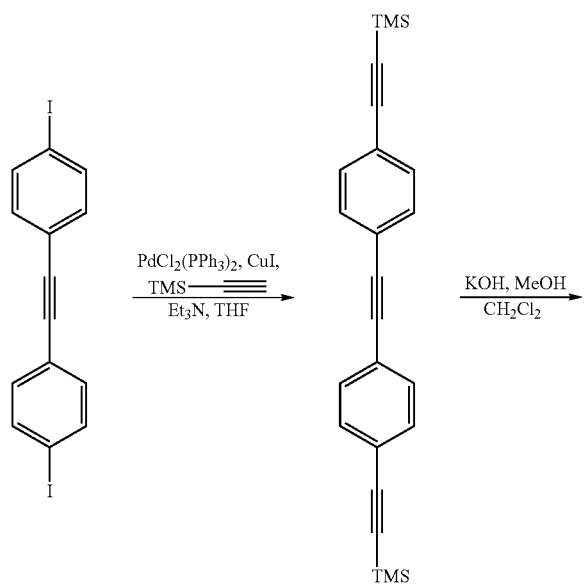

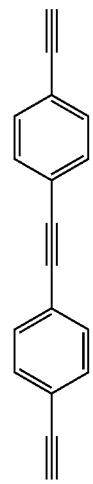

Firstly, a mixture of 4,4'-diiodotolan (171 mg, 0.40 mmol), PdCl$_2$(PPh$_3$)$_2$ (27.9 mg, 0.040 mmol) and CuI (7.6 mg, 0.040 mmol) was added with dist. THF (3 mL), dist. Et$_3$N (3 mL) and trimethylsilylacetylene (140 μL, 0.99 mmol). The resultant mixture was then stirred under a nitrogen atmosphere at 50° C. for 17 hours to obtain a reaction mixture. Subsequently, the reaction mixture was diluted with CH$_2$Cl$_2$. After that, an organic layer was washed with sat. NaCl, and the washed organic layer was then dried with MgSO$_4$. The dried organic layer was filtered and concentrated to obtain a crude product (I). The obtained crude product (I) was separated and purified by silica gel column chromatography (hexane/EtOAc=10/1) to obtain 4,4'-bis(trimethylsilylethynyl)tolan.

Subsequently, the obtained 4,4'-bis(trimethylsilylethynyl)tolan (149 mg, 0.40 mmol) was added with dist. CH$_2$Cl$_2$ (5 mL), dist. MeOH (1 mL) and an aqueous solution of KOH of 50% by mass (0.09 mL). The resultant mixture was then stirred under a nitrogen atmosphere at room temperature for 18 hours to obtain a reaction mixture. After that, the reaction mixture was diluted with CH$_2$Cl$_2$. The organic layer was washed with sat. NaCl, and the washed organic layer was dried with MgSO$_4$. The dried organic layer was filtered and concentrated to obtain a crude product (II). Subsequently, the obtained crude product (II) was separated and purified by silica gel column chromatography (hexane/EtOAc=10/1) to obtain 4,4'-diethynyltolan (60.5 mg, 86% yield (in two steps)).

The obtained compound was subjected to a $^1$H NMR measurement. The obtained result is shown below.

$^1$H NMR (CDCl$_3$) δ7.48 (s, 8H), 3.18 (s, 2H)

From the NMR measurement result, it was confirmed that the obtained compound was 4,4'-diethynyltolan.

Example 19

4,4'-bis[4-(diallylethoxysilyl)phenyethynyl]tolan was prepared as follows.

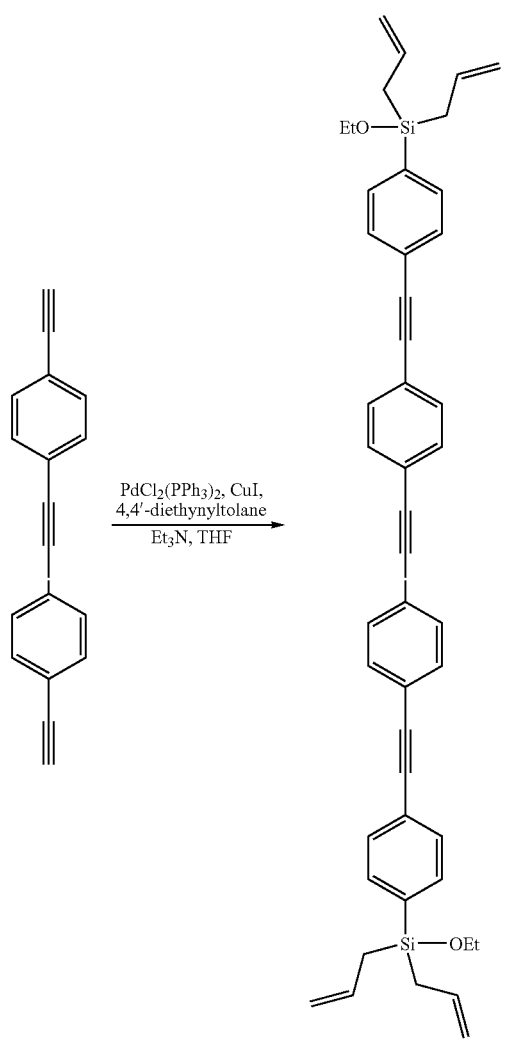

Firstly, a mixture of 4-(diallylethoxysilyl)iodobenzene (75.7 mg, 0.21 mmol) obtained in Synthesis example 7, PdCl$_2$(PPh$_3$)$_2$ (2.97 mg, 0.0042 mmol), CuI (0.8 mg, 0.0042 mmol) and 4,4'-diethynyltolan (34.5 mg, 0.15 mmol) was added with dist. THF (5 mL) and dist. Et$_3$N (1 mL). The resultant mixture was then stirred under a nitrogen atmosphere at 50° C. for 15 hours to obtain a reaction mixture. Subsequently, the reaction mixture was diluted with ether. After that, an organic layer was washed with dist. H$_2$O and sat. NaCl, and the washed organic layer was then dried with MgSO$_4$. The dried organic layer was filtered and concentrated to obtain a crude product. The obtained crude product was separated and purified by silica gel column chromatography (hexane/EtOAc=10/1) to obtain 4,4'-bis[4-(diallylethoxysilyl)phenylethynyl]tolan (68.1 mg, 94% yield).

The obtained compound was subjected to $^1$H NMR and $^{13}$C NMR measurements. The obtained results are shown below.

$^1$H NMR (CDCl$_3$) δ7.58 (d, J=8.1 Hz, 4H), 7.53 (d, J=8.1 Hz, 4H), 7.52 (s, 8H), 5.90-5.74 (m, 4H), 4.99-4.91 (m, 8H), 3.79 (q, J=7.0 Hz, 4H), 1.95 (d, J=7.8 Hz, 8H), 1.23 (t, J=7.0 Hz, 6H).

$^{13}$C NMR (CDCl$_3$) δ135.9, 133.9, 132.8, 131.6, 131.5, 130.7, 124.3, 123.2, 122.9, 115.0, 91.3, 91.0, 90.0, 59.4, 21.1, 18.4.

From the NMR measurement results, it was confirmed that the obtained compound was 4,4'-bis[4-(diallylethoxysilyl)phenylethynyl]tolan.

Synthesis Example 16

5,5'-diethynyl-2,2'-bipyridyl was prepared as follows.

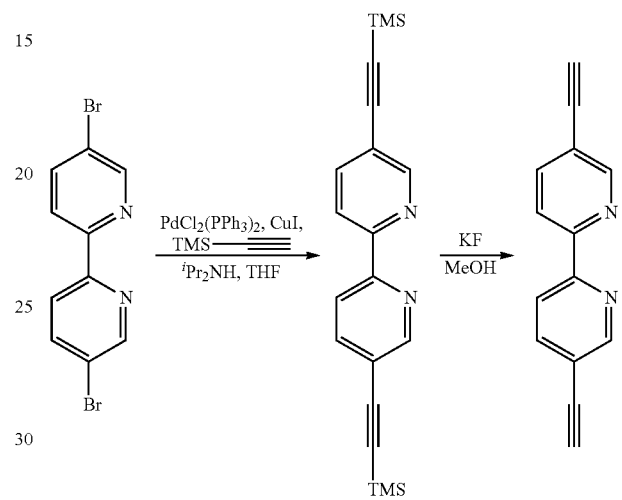

Firstly, a mixture of 5,5'-dibromo-2,2'-bipyridyl (300 mg, 0.96 mmol), PdCl$_2$(PPh$_3$)$_2$ (60 mg, 0.085 mmol) and CuI (30 mg, 0.16 mmol) was added with dist. THF (18 mL), dist. i-Pr$_2$NH (2.4 mL) and trimethylsilylacetylene (467 μL, 3.3 mmol). The resultant mixture was then stirred under a nitrogen atmosphere at room temperature for 29 hours to obtain a reaction mixture. Subsequently, a salt contained in the reaction mixture was removed through a celite filtration process. The organic layer thus obtained was concentrated to obtain a crude product (I) Then, the obtained crude product (I) was separated and purified by silica gel column chromatography (CH$_2$Cl$_2$=100) to obtain 5,5'-bis(trimethylsilylethynyl)-2,2'-bipyridyl.

Subsequently, the obtained 5,5'-bis(trimethylsilylethynyl)-2,2'-bipyridyl (120 mg, 0.34 mmol) and potassium fluoride (KF: 42 mg, 0.72 mmol) were added with dist. methanol (MeOH: 12 mL). The resultant mixture was then stirred under a nitrogen atmosphere at room temperature for 11 hours to obtain a reaction mixture. After that, an organic layer in the reaction mixture was then concentrated to obtain a crude product (II). Subsequently, the obtained crude product (II) was separated and purified by silica gel column chromatography (CH$_2$Cl$_2$=100) to obtain 5,5'-diethynyl-2,2'-bipyridyl (59.5 mg, 85% yield (in two steps)).

The obtained compound was subjected to a $^1$H NMR measurement. The obtained result is shown below.

$^1$H NMR (CDCl$_3$) δ8.77 (dd, J=0.5 Hz, 1.9 Hz, 2H), 8.40 (dd, J=0.5 Hz, 8.1 Hz, 2H), 7.90 (dd, J=1.9 Hz, 8.1 Hz, 2H), 3.31 (s, 2H).

From the NMR measurement result, it was confirmed that the obtained compound was 5,5'-diethynyl-2,2'-bipyridyl.

Example 20

5,5'-bis[4-(diallylethoxysilyl)phenylethynyl]-2,2'-bipyridyl was prepared as follows.

Firstly, a mixture of 5,5'-diethynyl-2,2'-bipyridyl (40 mg, 0.196 mmol) obtained in Synthesis example 16, 4-(diallylethoxysilyl)iodobenzene (140 mg, 0.39 mmol) and Pd(PPh$_3$)$_4$ (45 mg, 0.038 mmol) was added with distilled benzene (dist. benzene: 10 mL) and dist. i-Pr$_2$NH (4 mL) The resultant mixture was then stirred under a nitrogen atmosphere at 75° C. for 39 hours to obtain a reaction mixture. Subsequently, the reaction mixture was diluted with CH$_2$Cl$_2$. After that, an organic layer was washed with dist. H$_2$O and sat. NaCl, and the washed organic layer was then dried with MgSO$_4$. The dried organic layer was filtered and concentrated to obtain a crude product (130 mg, 100% gross yield).

The obtained compound was subjected to a $^1$H NMR measurement. The obtained result is shown below.

$^1$H NMR (CDCl$_3$) δ8.82 (d, J=1.9 Hz, 2H), 8.44 (d, J=8.1 Hz, 2H), 7.95 (d, J=1.9 Hz, 8.1 Hz, 2H), 7.58 (s, 8H), 5.89-5.74 (m, 4H), 5.02-4.91 (m, 8H), 3.79 (q, J=7.0 Hz, 4H), 1.95 (d, J=7.8 Hz, 8H), 1.23 (t, J=7.0 Hz, 6H).

From the NMR measurement result, it was confirmed that the obtained compound was 5,5'-bis[4-(diallylethoxysilyl)phenylethynyl]-2,2'-bipyridyl.

Example 21

N,N-diphenyl-4-(diallylethoxysilyl)aniline was prepared as follows.

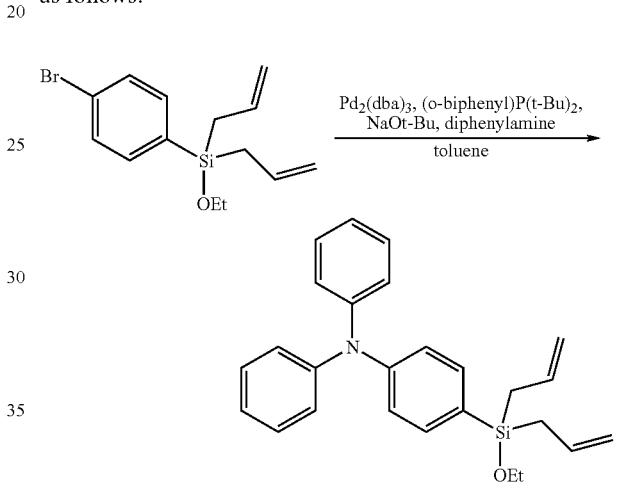

Firstly, a mixture of 4-(diallylethoxysilyl)bromobenzene (486 mg, 1.56 mmol) obtained in Synthesis example 9, Pd$_2$(dba)$_3$ (21.5 mg, 0.023 mmol), (o-biphenyl)P(t-Bu)$_2$ (42.0 mg, 0.14 mmol), NaOt-Bu (225 mg, 2.34 mmol) and diphenylamine (317 mg, 1.87 mmol) was added with dist. toluene (15 mL). The resultant mixture was then stirred under a nitrogen atmosphere at 80° C. for 19 hours to obtain a reaction mixture. Subsequently, the reaction mixture was diluted with ether. A salt thus formed was removed through a celite filtration process. The solvent was distilled away from an organic layer with an evaporator to obtain a crude product. The obtained crude product was separated and purified by silica gel column chromatography (hexane/EtOAc=5/1) to obtain N,N-diphenyl-4-(diallylethoxysilyl)aniline (384 mg, 62% yield).

The obtained compound was subjected to $^1$H NMR and $^{13}$C NMR measurements. The obtained results are shown below.

$^1$H NMR (CDCl$_3$) δ7.41 (d, J=8.1 Hz, 5H), 7.28 (d, J=8.1 Hz, 2H), 7.25 (d, J=8.1 Hz, 2H), 7.13-7.02 (m, 6H), 7.03 (d, J=8.1 Hz, 2H), 5.93-5.77 (m, 2H), 5.00-4.90 (m, 4H), 3.77 (q, J=7.0 Hz, 2H), 1.92 (d, J=8.1 Hz, 4H), 1.20 (t, J=7.0 Hz, 3H).

$^{13}$C NMR (CDCl$_3$) δ149.2, 147.3, 134.9, 133.4, 129.3, 127.3, 124.9, 123.3, 121.7, 114.6, 59.2, 21.3, 18.4.

From the NMR measurement results, it was confirmed that the obtained compound was N,N-diphenyl-4-(diallylethoxysilyl)aniline.

Example 22

4-(diallylethoxysilyl)styrene was prepared as follows.

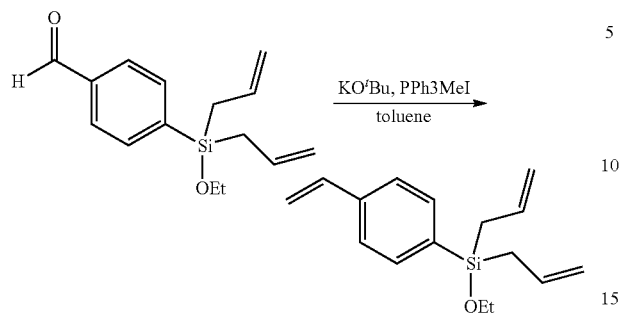

Firstly, PPh₃MeI (317 mg, 0.78 mmol: Me=methyl) was added with dist. toluene (4 mL). The resultant mixture was then added with KOt-Bu (88 mg, 0.78 mmol) at 0° C., and then was stirred under a nitrogen atmosphere at 0° C. for 30 minutes to obtain a mixture. Subsequently, the obtained mixture was added dropwise with a mixed solution (2 mL) of 4-(diallylethoxysilyl)benzaldehyde (204.2 mg, 0.78 mmol) obtained in Example 12 and dist. toluene under a nitrogen atmosphere at 0° C. The resultant mixture was stirred under a nitrogen atmosphere at 0° C. for 1.5 hours, and then was stirred at room temperature for 17 hours to obtain a reaction mixture. After that, a salt contained in the reaction mixture was removed through a celite filtration process. The organic layer thus obtained was then concentrated under reduced pressure to obtain a crude product. The obtained crude product was separated and purified by silica gel column chromatography (hexane/EtOAc=20/1) to obtain 4-(diallylethoxysilyl)styrene (134.3 mg, 66% yield).

The obtained compound was subjected to $^1$H NMR and $^{13}$C NMR measurements. The obtained results are shown below.

$^1$H NMR (CDCl₃) δ7.54 (d, J=8.1 Hz, 2H), 7.41 (d, J=8.1 Hz, 2H), 6.74-6.66 (m, 1H), 5.90-5.74 (m, 3H), 5.27 (dd, J=0.8 Hz, 10.8 Hz, 1H), 4.99-4.88 (m, 4H), 3.76 (q, J=7.0 Hz, 2H), 1.93 (d, J=7.8 Hz, 4H), 1.20 (t, J=7.0 Hz, 3H).

$^{13}$C NMR (CDCl₃) δ138.8, 136.7, 134.6, 134.3, 133.1, 125.5, 114.7, 114.6, 59.3, 21.2, 18.4.

From the NMR measurement results, it was confirmed that the obtained compound was 4-(diallylethoxysilyl)styrene.

Example 23

5,5'-bis[4-(diallylhydroxysilyl)phenylethynyl]-2,2'-bipyridyl was prepared as follows.

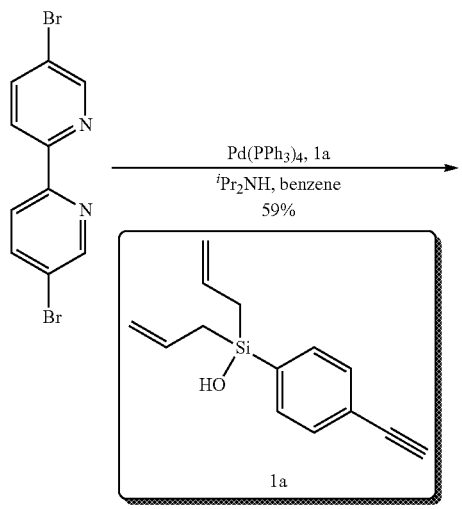

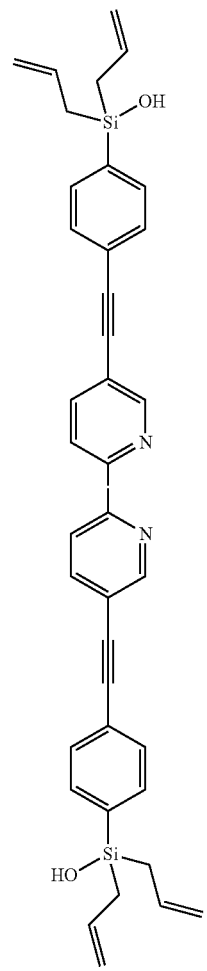

A mixture of 4-(diallylhydroxysilyl)ethynylbenzene (157 mg, 0.69 mmol), Pd(PPh₃)₄ (66 mg, 0.057 mmol) and 5,5'-dibromo-2,2'-bipyridyl (90 mg, 0.29 mmol) was added with dist. benzene (12 mL) and dist. i-Pr₂NH (4 mL). The resultant mixture was then stirred under a nitrogen atmosphere at 80° C. for 30 hours to obtain a reaction mixture. Subsequently, the reaction mixture was diluted with CH₂Cl₂. After that, an organic layer was washed with dist. H₂O and sat. NaCl, and then the organic layer was dried with MgSO₄. The dried organic layer was filtered and concentrated to obtain a crude product. After that, the obtained crude product was separated and purified by silica gel column chromatography (from CH₂Cl₂=100 to CH₂Cl₂/Acetone=30/1) to obtain 5,5'-bis[4-(diallylhydroxysilyl)phenylethynyl]-2,2'-bipyridyl (103.5 mg, 59% yield).

The obtained compound was subjected to a $^1$H NMR measurement. The obtained result is shown below.

$^1$H NMR (CDCl₃) δ1.93 (ddd, J=8.1 Hz, 1.1 Hz, 0.8 Hz, 8H), 2.17 (s, 2H), 4.95 (ddt, J=10.3 Hz, 1.6 Hz, 0.8 Hz, 4H) 4.98 (ddt, J=16.2 Hz, 1.6 Hz, 1.1 Hz, 4H), 5.81 (ddt, J=16.2 Hz, 10.3 Hz, 8.1 Hz, 4H), 7.55 (d, J=8.4 Hz, 4H), 7.60 (d, J=8.4 Hz, 4H), 7.90 (dd, J=8.4 Hz, 1.9 Hz, 2H), 8.39 (dd, J=8.4 Hz, 0.5 Hz, 2H), 8.77 (dd, J=1.9 Hz, 0.5 Hz, 2H).

From the NMR measurement result, it was confirmed that the obtained compound was 5,5'-bis[4-(diallylhydroxysilyl) phenylethynyl]-2,2'-bipyridyl.

Example 24

4,4'-bis[4-(diallylethoxysilyl)phenyl]acetylene was prepared as follows.

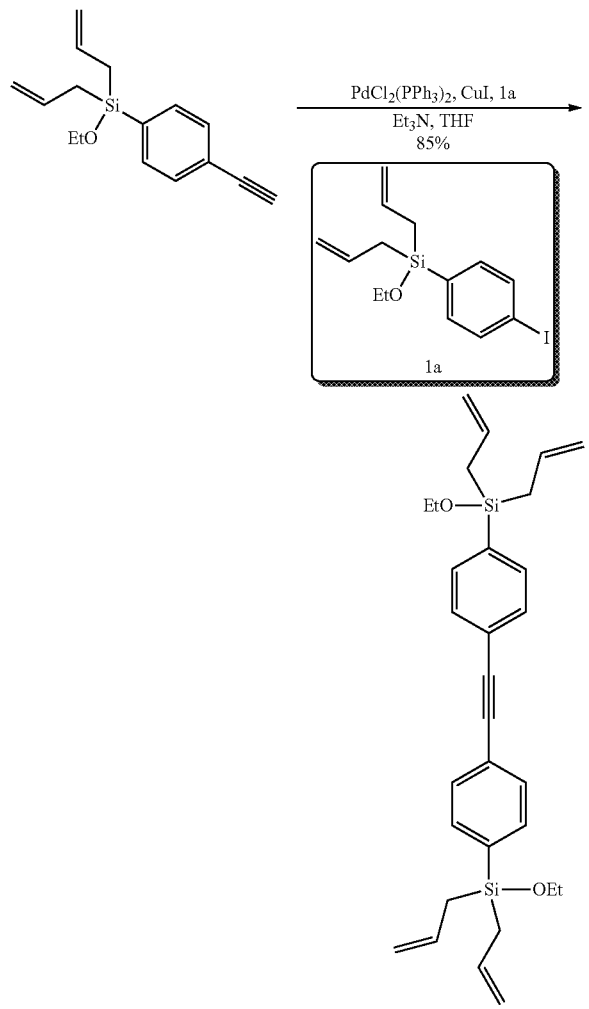

A mixture of 4-(diallylethoxysilyl)iodobenzene (335.3 mg, 0.936 mmol), PdCl$_2$(PPh$_3$)$_2$ (19.7 mg, 0.028 mmol), CuI (5.4 mg, 0.028 mmol) and 4-(diallylethoxysilyl)-1-ethynylbenzene (240 mg, 0.936 mmol) was added with dist. THF (4 mL) and dist. Et$_3$N (4 mL). The resultant mixture was stirred under a nitrogen atmosphere at 50° C. for 20 hours to obtain a reaction mixture. Then, the obtained reaction mixture was diluted with ether. After that, an organic layer was washed with dist. H$_2$O and sat. NaCl, and the organic layer was then dried with MgSO$_4$. The dried organic layer was filtered and concentrated to obtain a crude product. Subsequently, the obtained crude product was separated and purified by silica gel column chromatography (hexane/EtOAc=5/1) to obtain 4,4'-bis[4-(diallylethoxysilyl)phenyl]acetylene (385 mg, 85% yield).

The obtained compound was subjected to a $^1$H NMR measurement. The obtained result is shown below.

$^1$H NMR (CDCl$_3$) δ1.22 (t, J=6.8 Hz, 6H), 1.89-1.96 (m, 8H), 3.78 (q, J=6.8 Hz, 4H), 4.50-4.90 (m, 8H), 5.73-5.89 (m, 4H), 7.52 (d, J=5.4 Hz, 4H), 7.56 (d, J=5.4 Hz, 4H).

From the NMR measurement result, it was confirmed that the obtained compound was 4,4'-bis[4-(diallylethoxysilyl)phenyl]acetylene.

Example 25

4-(2-bromoethenyl)-1-diallylethoxysilylbenzene was prepared as follows.

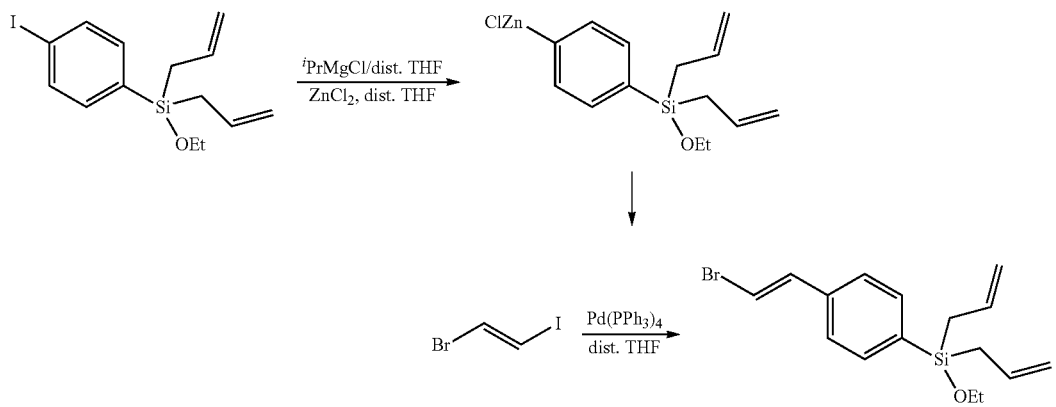

Firstly, 4-diallylethoxysilyliodobenzene (157 mg, 0.438 mmol) was added with distilled tetrahydrofuran (dist. THF: 1.5 mL) under a nitrogen atmosphere, and iso-propylmagnesium chloride (i-PrMgCl: 420 μL, 2 M in THF, 0.840 mmol) was added dropwise at −30° C. The mixture thus produced

Example 26

(Z,Z)-1,4-bis[(4-diallylethoxysilyl)phenylethenyl]benzene was prepared as follows.

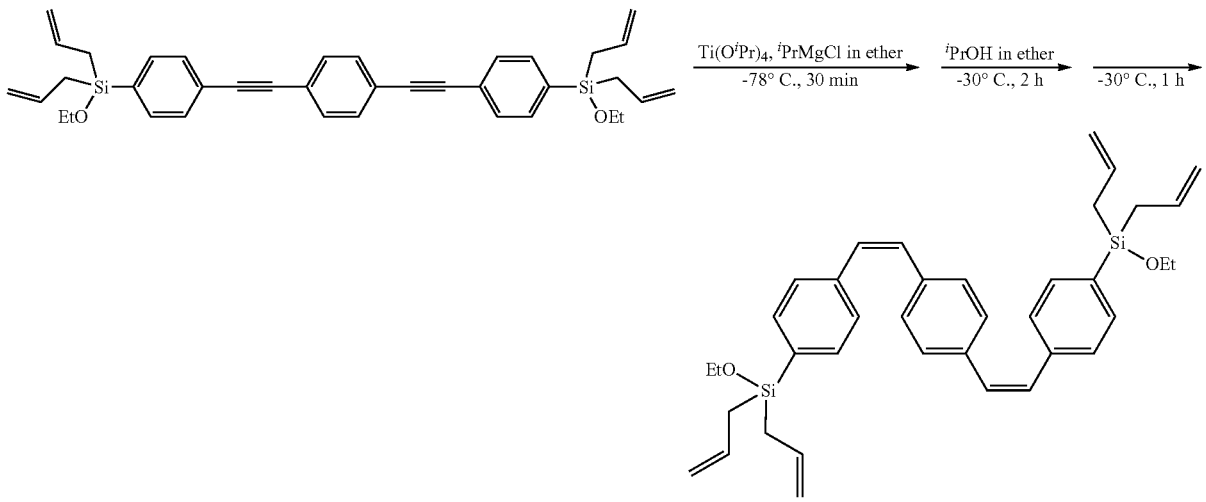

was then stirred at −30° C. for 1.5 hours to obtain a solution (A). Subsequently, the solution (A) was added dropwise, at −30° C., with a solution (B) obtained by adding, under a nitrogen atmosphere, dist. THF (2.5 mL) to a solution of $ZnCl_2$ (91 mg, 0.670 mmol) that had been vacuum-dried and dissolved in dist. THF (2.0 mL). The resultant mixture was then stirred for 30 minutes to obtain a solution (C).

Subsequently, the solution (C) was added dropwise, at −30° C., into a solution (D) prepared under a nitrogen atmosphere and containing $Pd(PPh_3)_4$ (24 mg, 0.021 mmol), dist. THF (1.5 mL), and 1-bromo-2-iodoethene (195 mg, 0.837 mmol). The resultant mixture was stirred for 40 minutes, and then was further stirred at room temperature for 11.5 hours to obtain a reaction mixture. Then, the reaction mixture was added with ether, and the reaction was then ceased by a saturated solution of sodium chloride. Thereafter, an organic layer extracted with ether and the collected organic layer was washed with a saturated solution of sodium chloride. After that, the organic layer was dried with anhydrous $MgSO_4$. The dried organic layer was filtered and concentrated to obtain a crude product. Then, the obtained crude product was passed through a silica gel column (hexane/ethyl acetate=5/1), and purified by liquid chromatography to obtain 4-(2-bromoethenyl)-1-diallylethoxysilylbenzene (48 mg, 33% yield).

The obtained compound was subjected to $^1H$ NMR and $^{13}C$ NMR measurements. The obtained results are shown below.

$^1H$ NMR (CDCl$_3$) δ1.22 (t, J=6.8 Hz, 3H), 1.94 (ddd, J=8.1 Hz, 1.4 Hz, 1.1 Hz, 4H), 3.77 (q, J=6.8 Hz, 2H), 4.92 (ddt, J=10.3 Hz, 1.6 Hz, 1.1 Hz, 2H), 4.96 (ddt, J=17.3 Hz, 1.6 Hz, 1.4 Hz, 2H), 5.82 (ddt, J=17.3 Hz, 10.3 Hz, 8.1 Hz, 2H), 6.83 (d, J=13.8 Hz, 1H), 7.11 (d, J=13.8 Hz, 1H), 7.31 (d, J=7.8 Hz, 2H), 7.54 (d, J=7.8 Hz, 2H).

$^{13}C$ NMR (CDCl$_3$) δ18.36, 21.16, 59.32, 107.38, 114.88, 125.37, 132.91, 134.49, 135.42, 137.05, 137.08.

From the NMR measurement results, it was confirmed that the obtained compound was 4-(2-bromoethenyl)-1-diallylethoxysilylbenzene.

Firstly, 1,4-bis[(4-diallylethoxysilyl)phenylethynyl]benzene (385 mg, 0.657 mmol) was added with distilled diethyl ether (11.6 mL) and distilled titanium isopropoxide (dist. Ti(Oi-Pr)$_4$: 480 μL, 1.65 mmol) under a nitrogen atmosphere and a light-shielding condition. The resultant mixture was further added dropwise with i-PrMgCl (1.65 mL, 2 M in ether, 3.30 mmol) at −78° C. The mixture newly produced was stirred at −78° C. for 30 minutes, and then was further stirred at −30° C. for 2 hours to obtain a solution. Then, iso-propanol (i-PrOH: 1.45 mL, 1 M in ether, 1.45 mmol) was added dropwise to the obtained solution. The resultant solution was stirred at −30° C. for 1 hour to obtain a reaction mixture. Thereafter, the reaction mixture was added with ether, and the reaction was ceased by a saturated aqueous solution of ammonium chloride. Then, an aqueous layer was extracted with ether, and the collected organic layer was washed with a saturated aqueous solution of sodium acid carbonate and a saturated aqueous solution of sodium chloride. After that, the organic layer was dried with anhydrous MgSO$_4$. The dried organic layer was filtered and concentrated to obtain a crude product. Then, the obtained crude product was passed through silica gel column (hexane/ethyl acetate=10/1), and was purified by liquid chromatography to obtain (Z,Z)-1,4-bis[(4-diallylethoxysilyl)phenylethenyl]benzene (146 mg, 38% yield).

The obtained compound was subjected to $^1H$ NMR and $^{13}C$ NMR measurements. The obtained results are shown below.

$^1H$ NMR (CDCl$_3$) δ1.20 (t, J=7.3 Hz, 6H), 1.96 (ddd, J=7.8 Hz, 1.4 Hz, 1.4 Hz, 8H), 3.77 (q, J=7.3 Hz, 4H), 4.89 (ddt, J=9.7 Hz, 1.9 Hz, 1.4 Hz, 8H), 4.94 (ddt, J=15.7 Hz, 1.9 Hz, 1.4 Hz, 4H), 5.82 (ddt, J=15.7 Hz, 9.7 Hz, 7.8 Hz, 4H), 6.56 (s, 4H), 7.12 (s, 4H), 7.29 (d, J=7.8 Hz, 2H), 7.44 (d, J=7.8 Hz, 2H).

$^{13}C$ NMR (CDCl$_3$) δ18.38, 21.23, 59.30, 114.73, 128.12, 128.73, 130.08, 130.42, 133.12, 133.94, 133.99, 136.05, 138.70.

From the NMR measurement results, it was confirmed that the obtained compound was (Z,Z)-1,4-bis[(4-diallylethoxysilyl)phenylethenyl]benzene.

Example 27

1,4-bis[4-(diallylethoxysilyl)phenyl]-(Z)-1-butene-3-yne was prepared as follows.

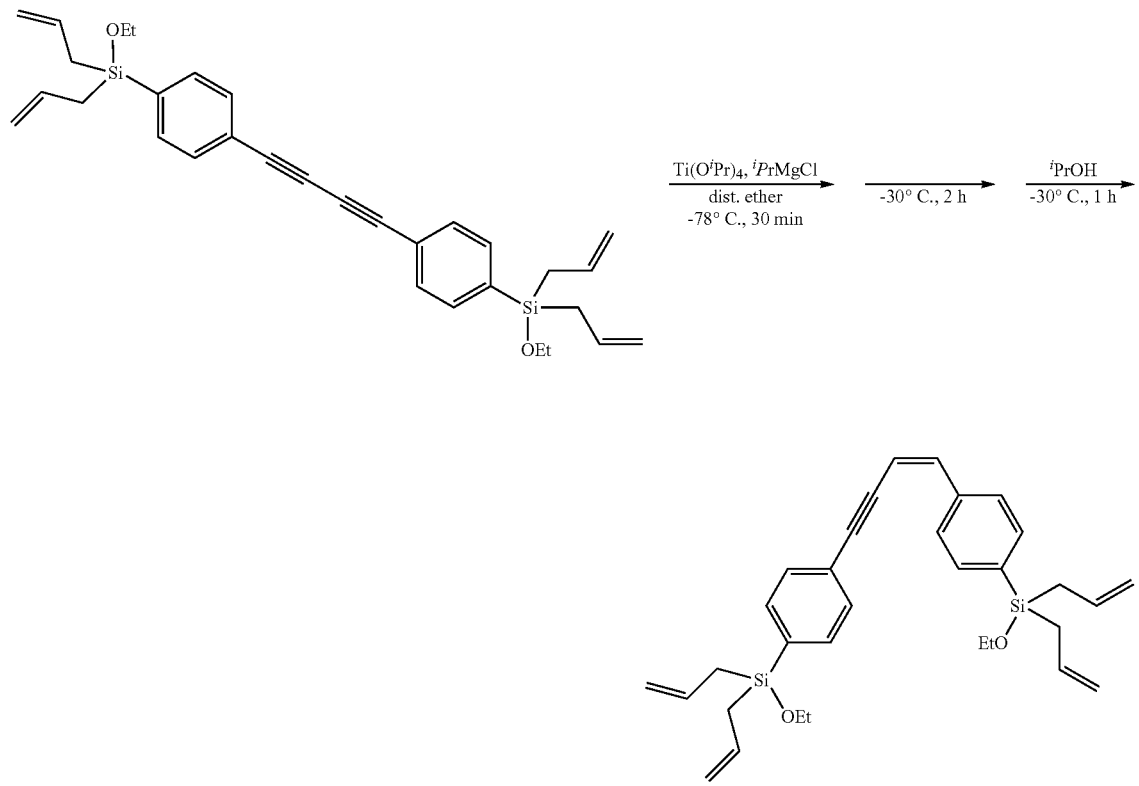

Firstly, distilled diethyl ether (6 mL) and dist. Ti(Oi-Pr)$_4$ (136 μL, 0.469 mmol) was added to 1,4-bis[4-(diallylethoxysilyl)phenyl]butydiyne (200 mg, 0.391 mmol) under a nitrogen atmosphere and a light-shielding condition. The resultant solution was added dropwise with i-PrMgCl (470 μL, 2M in ether, 0.938 mmol) at −78° C. The mixture newly produced was stirred at −78° C. for 30 minutes, and then was further stirred at −30° C. for 2 hours to obtain a solution. Then, i-PrOH (430 μL, 1 M in ether, 0.430 mmol) was added dropwise to the obtained solution. The resultant solution was then stirred at −30° C. for 1 hour to obtain a reaction mixture. Subsequently, the reaction mixture was added with ether, and the reaction was ceased by a saturated aqueous solution of ammonium chloride. After that, an aqueous layer was extracted with ether, and an organic layer thus collected was washed with a saturated aqueous solution of sodium acid carbonate and a saturated aqueous solution of sodium chloride. Then, the organic layer was dried with anhydrous MgSO$_4$. The dried organic layer was filtered and concentrated to obtain a crude product. Thereafter, the obtained crude product was passed through silica gel column (hexane/ethyl acetate=10/1), and was purified by liquid chromatography to obtain 1,4-bis[4-(diallylethoxysilyl)phenyl]-(Z)-1-butene-3-yne (21 mg, 11% yield).

The obtained compound was subjected to $^1$H NMR and $^{13}$C NMR measurements. The obtained results are shown below.

$^1$H NMR (CDCl$_3$) δ1.23 (t, J=6.8 Hz, 6H), 1.96 (d, J=7.8 Hz, 8H), 3.79 (q, J=6.8 Hz, 4H), 4.91-4.95 (m, 8H), 5.74-5.92 (m, 4H), 5.96 (d, J=11.9 Hz, 1H), 6.71 (d, J=12.2 Hz, 1H), 7.48 (m, 6H), 7.93 (d, 2H).

$^{13}$C NMR (CDCl$_3$) δ18.38, 21.13, 21.19, 59.34, 59.39, 89.12, 96.34, 108.07, 114.85, 114.98, 124.65, 127.96, 130.57, 130.75, 132.82, 133.00, 133.98, 134.04, 135.833, 137.69, 138.68.

From the NMR measurement results, it was confirmed that the obtained compound was 1,4-bis[4-(diallylethoxysilyl)phenyl]-(Z)-1-butene-3-yne.

Example 28

An organosilane compound essentially containing a ruthenium complex was prepared as follows.

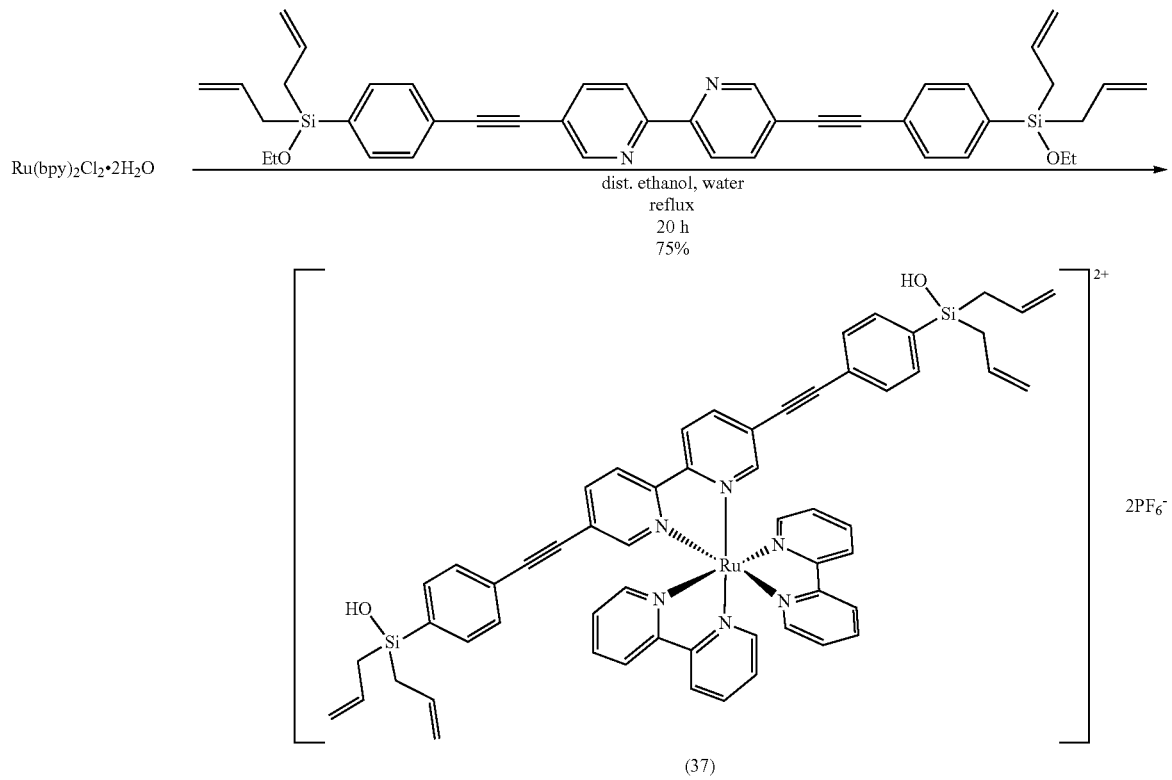

Ru(bpy)$_2$Cl$_2$·2H$_2$O (179.6 mg, 1 equivalent (eq)) and 5,5'-bis[(4-diallylethoxysilyl)phenylethynyl]-2,2'-bipyridine (270 mg, 1.2 eq) obtained in a method that was similar to the method employed in Example 20 were put in a nitrogen-flushed reaction vessel, and were dissolved in distilled ethanol (18 ml) to obtain a solution. Then, water (6 ml) was calmly added to the solution by a syringe while the solution was stirred. Then, the resultant solution was refluxed in an oil bath. After refluxed and stirred for 20 hours, the solution was cooled down to room temperature. Then, the solution was reduced in its quantity by half approximately using an evaporator. After that, an aqueous solution of NH$_4$PF$_6$ was added dropwise to the obtained solution, and a precipitated solid was suctioned and filtered. The solid thus obtained was washed with water, and was dried thereby to obtain a ruthenium complex expressed by the general formula (37) in the above-mentioned reaction formula (a solid in a terra-cotta color, 334 mg, 75% yield).

The obtained compound was subjected to $^1$H NMR measurements. The obtained results are shown below.

$^1$H NMR (DMSO-d$_6$) δ1.77 (d, J=7.81 Hz, 8H), 4.81 (m, 8H), 5.72 (m, 4H), 7.46 (d, J=8.09 Hz, 4H), 7.54 (m, 2H), 7.58 (d, J=8.09 Hz, 4H), 7.70 (m, 2H), 7.76 (m, 2H), 7.86 (m, 2H), 8.18 (m, 4H), 8.36 (m, 2H), 8.83 (m, 6H), 8.91 (d, J=8.09 Hz, 2H).

Figure 4:
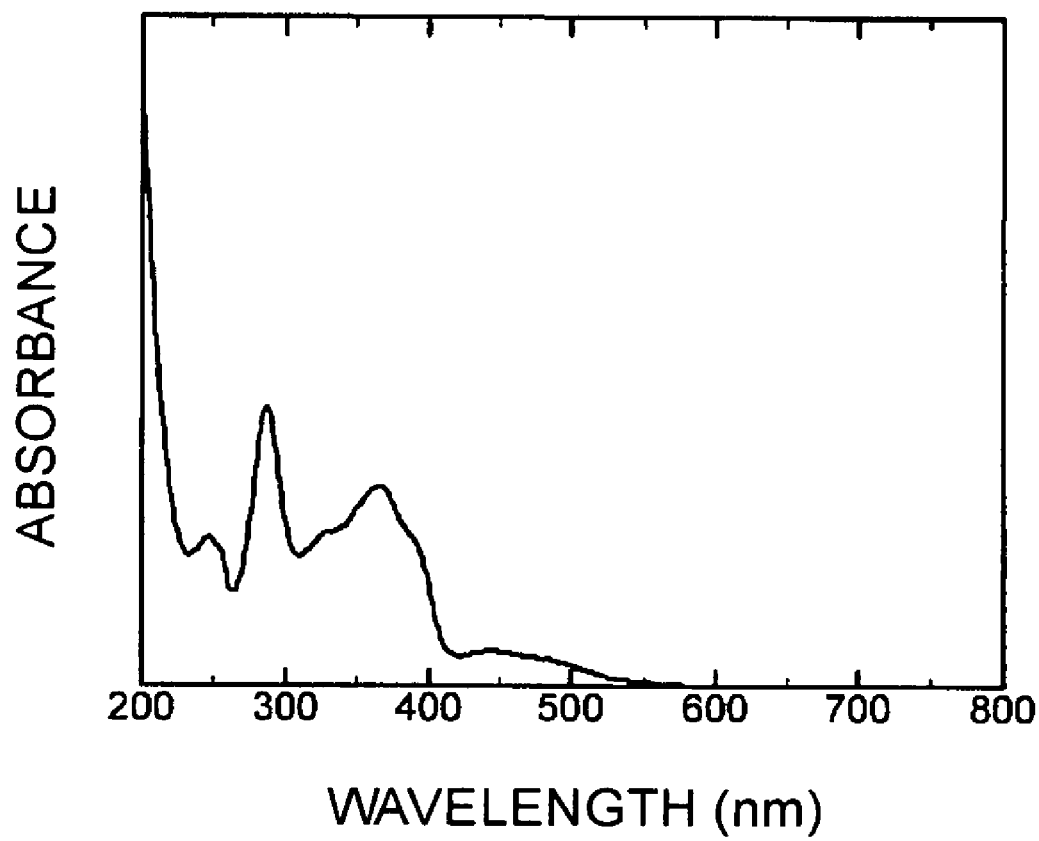
FIG. 4 is a graph showing an ultraviolet-visible absorption spectrum of a ruthenium complex obtained in Example 28.

The solid thus obtained was dissolved in acetonitrile, and the ultraviolet-visible absorption spectrum was measured. The obtained graph of the ultraviolet-visible absorption spectrum is shown in FIG. 4. The result shown in FIG. 4 clearly indicates that the spectrum of the obtained ruthenium complex had absorption maximums at 287 nm, 369 nm, and 441 nm.

[Synthesis of Organosilica Thin Film]

Example 29

An organosilica thin film was synthesized as follows.

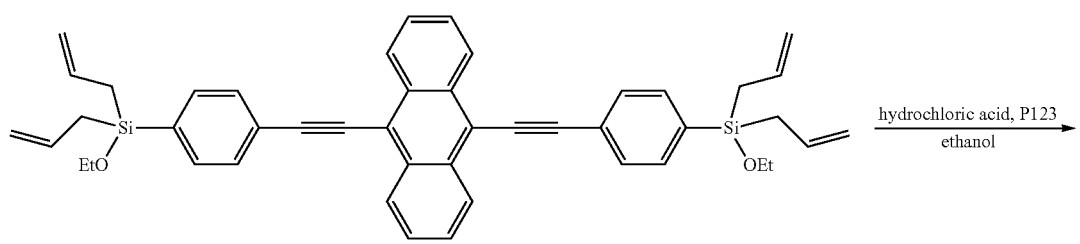

-continued

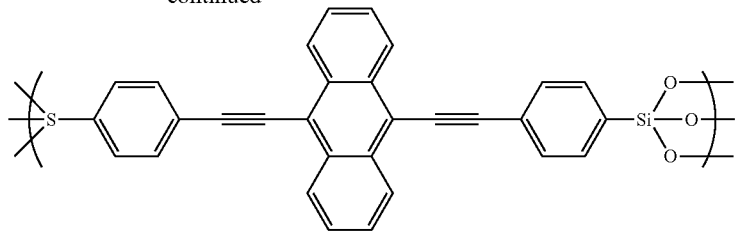

Figure 5:
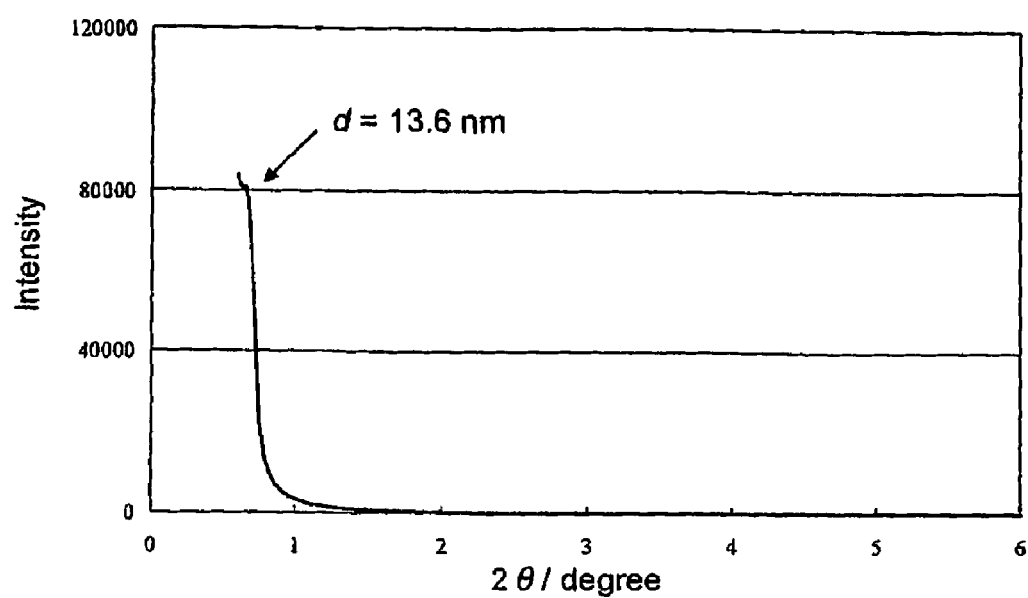
FIG. 5 is a graph showing an X-ray diffraction pattern of an organosilica thin film obtained in Example 29.

Firstly, a mixture of 9,10-bis(4-diallylethoxysilylphenyl-ethynyl)anthracene (50 mg) obtained in Example 18, a surfactant P123 (($EO)_{20}(PO)_{70}(EO)_{20}$: 20 mg), ethanol (5 g), 2-M aqueous solution of hydrochloric acid (10 µL) and water (40 µL) was heated and stirred at 100° C. for 19 hours to obtain a solution. Then, the obtained solution was spin-casted on a quartz substrate, and then was dried at 25° C. for 24 hours to obtain an organosilica thin film. A X-ray diffraction measurement was carried out on the thin film thus obtained. FIG. 5 shows the measurement result. The result shown in FIG. 5 indicates that a mesostructure with a 13.6-nm period was formed in the obtained thin film.

Example 30

Figure 6:
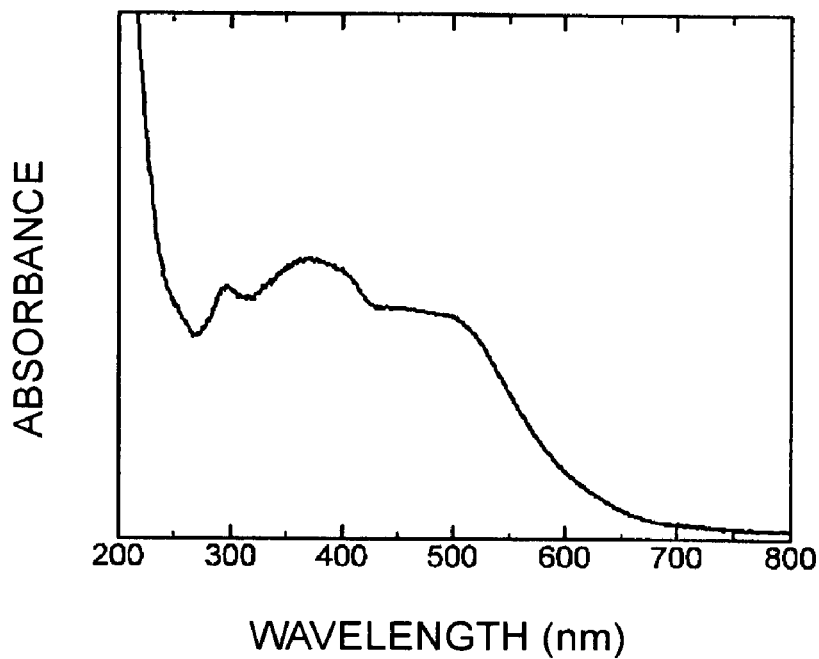
FIG. 6 is a graph showing a diffuse reflectance absorption spectrum of an organosilica powder obtained in Example 30.

An organosilica powder was synthesized by using the ruthenium complex obtained in Example 28. Firstly, the ruthenium complex (100 mg) obtained in Example 28 was dissolved in distilled tetrahydrofuran (4.6 ml) in a nitrogen-flushed reaction vessel, and then an aqueous solution of 2-M hydrochloric acid (404 µl) was added. The resultant solution was stirred at room temperature for 24 hours, and then was further stirred at 60° C. for another 24 hours to obtain a solution. Subsequently, the obtained solution was added with an aqueous solution of 2-M hydrochloric acid (3.6 ml). The resultant solution was stirred at 60° C. for 24 hours, and then was cooled down to room temperature (25° C.). The solution was then washed with acetone, and was dried. Thus obtained was a organosilica powder (81 mg) of a terra-cotta color. The organosilica powder thus obtained was mixed with barium sulfate, and then the diffuse reflectance absorption spectrum was measured for the mixed organosilica powder. FIG. 6 shows the measurement result. The result shown in FIG. 6 clearly indicates that the obtained organosilica powder absorbed the light at wavelengths around the range from 280 nm to 620 nm.

Example 31

Figure 7:
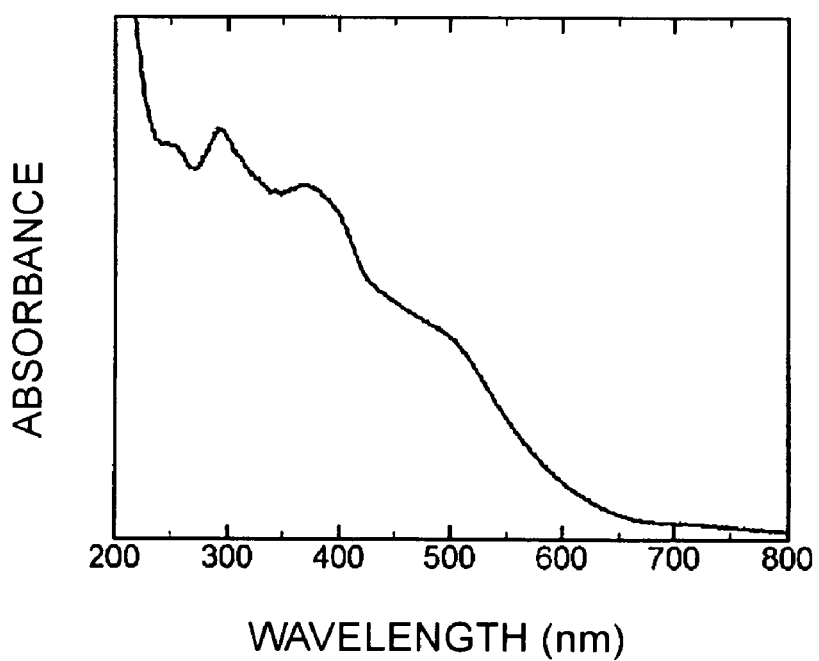
FIG. 7 is a graph showing a diffuse reflectance absorption spectrum of an organosilica powder obtained in Example 31.

An organosilica powder was synthesized by using the ruthenium complex obtained in Example 28. Firstly, the ruthenium complex (25 mg, 0.01905 mmol) obtained in Example 28, tetrahydrofuran (1.15 ml) and 2-M nitric acid (101 µl) were put in a nitrogen-flushed reaction vessel, and the mixture was stirred at room temperature for 24 hours. The mixture was further stirred at 60° C. for another 0.24 hours to obtain a solution. Then, the solution was added with 2-M nitric acid (101 µl), and stirred at 60° C. for 1 hour. After that, the resultant solution was added further with 2-M nitric acid (808 µl), and then stirred at 60° C. for 24 hours. The solution thus obtained was cooled down to room temperature (25° C.), and washed with acetone. The washed solution was then dried to obtain an organosilica powder (11.6 mg). The organosilica powder thus obtained was then mixed with barium sulfate, and then the diffuse reflectance absorption spectrum was measured for the mixed organosilica powder. FIG. 7 shows the measurement result. The result shown in FIG. 7 clearly indicates that the obtained organosilica powder absorbed the light at wavelengths around the range from 280 nm to 620 nm.

Example 32

Figure 8:
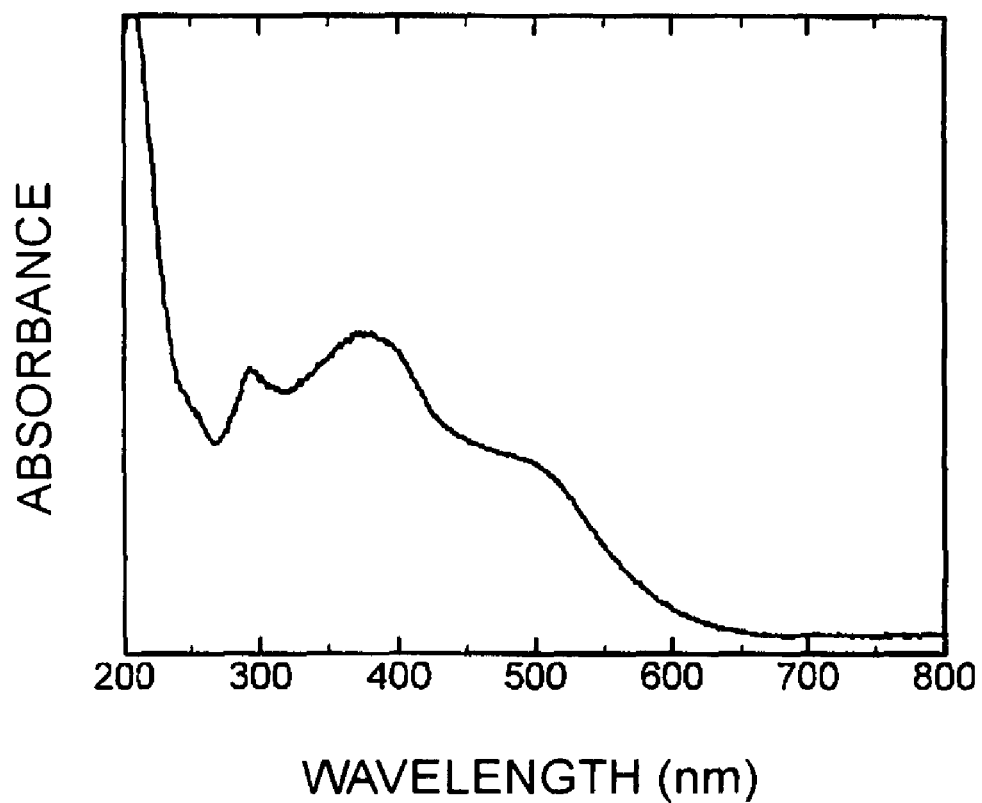
FIG. 8 is a graph showing a diffuse reflectance absorption spectrum of an organosilica powder obtained in Example 32.

An organosilica powder was synthesized by using the ruthenium complex obtained in Example 28. Firstly, the ruthenium complex (25 mg, 0.01905 mmol) obtained in Example 28, tetrahydrofuran (1.15 ml) and 2-M sulfuric acid (101 µl) were put in a nitrogen-flushed reaction vessel, and the mixture was stirred at room temperature for 24 hours. The mixture was further stirred at 60° C. for another 24 hours to obtain a solution. Then, the solution was added with 2-M sulfuric acid (909 µl), and then stirred at 60° C. for 24 hours. The resultant solution was added further with 2-M sulfuric acid (1 ml), and then stirred at 60° C. for 18 hours. The solution thus obtained was cooled down to room temperature (25° C.), and washed with acetone. The washed solution was then dried to obtain an organosilica powder (11.6 mg). The organosilica powder thus obtained was then mixed with barium sulfate, and then the diffuse reflectance absorption spectrum was measured for the mixed organosilica powder. FIG. 8 shows the measurement result. The result shown in FIG. 8 clearly indicates that the obtained organosilica powder absorbed the light at wavelengths around the range from 280 nm to 620 nm.

As has been described thus far, what is made possible by the present invention is the provision of an organosilane compound that is useful in synthesizing an organosilica having various functions, such as a refractive-index controlling function, a light absorbing function, a light emitting function, and a charge transferring function. Also made possible is the provision of an organosilica obtained by using the organosilane compound thus provided.

That is why the organosilane compound of the present invention is particularly useful as a material for producing an organosilica having various functions, such as a refractive-index controlling function, a light absorbing function, a light emitting function, and a charge transferring function.

What is claimed is:

1. An organosilane compound, expressed by any one of the following general formulae (1) to (7):

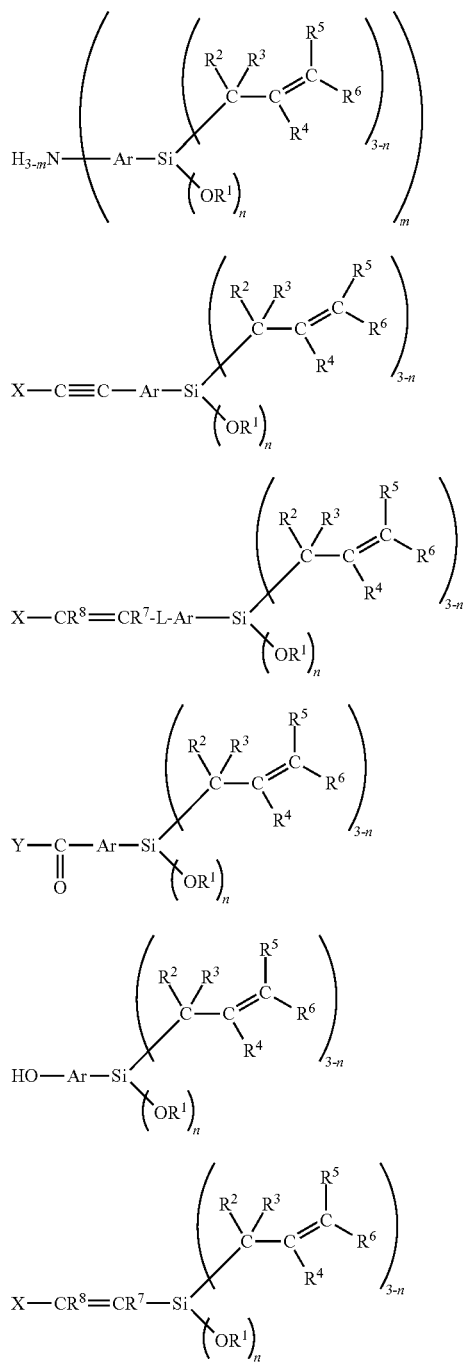

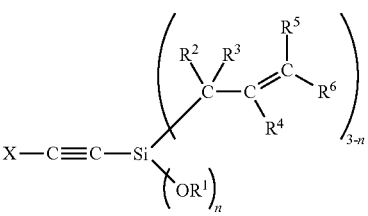

(wherein:

Ar represents any one divalent aromatic organic group selected from the group consisting of a phenylene group, a biphenylylene group, a naphthylene group, and a pyridylene group; $R^1$ represents any one of a hydrogen atom and alkyl groups having 1 to 4 carbon atoms; $R^2$ to $R^8$, which may be either identical to or different from each other, each represent any one of a hydrogen atom, a methyl group, an ethyl group, a propyl group, a butyl group, an isopropyl group, a pentyl group, a hexyl group, and a cyclohexyl group; n represents an integer in a range from 0 to 2; m represents an integer in a range from 1 to 2; L represents any one of a single bond and a divalent organic group selected from the group consisting of an ether group, an ester group, and an amide group; X represents any one of a hydrogen atom, a halogen atom, and a trialkylsilyl group; and Y represents any one of a hydrogen atom, a hydroxy group, an alkyl group having 1 to 10 carbon atoms, and a univalent aromatic organic group).

2. The organosilane compound according to claim 1, wherein $R^1$ in the general formulae (1) to (7) represents any one of a methyl group and an ethyl group.

3. The organosilane compound according to claim 1, wherein each of $R^7$ and $R^8$ in the general formulae (3) and (6) represents any one of the hydrogen atom and the methyl group.

4. The organosilane compound according to claim 1, wherein L in the general formula (3) represents any one of the single bond and the amide group.

5. The organosilane compound according to claim 1, wherein X in the general formulae (2), (3), (6), and (7) represents any one of the hydrogen atom and the halogen atom.

6. The organosilane compound according to claim 1, wherein Y in the general formula (4) represents any one of the hydrogen atom, the hydroxy group, and a pyridyl group.

7. An organosilica, obtained by polymerizing at least one kind of the organosilane compounds according to claim 1.

* * * * *